(12) United States Patent
Gershoni

(10) Patent No.: US 11,854,680 B1
(45) Date of Patent: Dec. 26, 2023

(54) NARCOTICS AND OPIOIDS SECURE STORAGE AND DISPENSING APPARATUS AND METHOD OF USE

(71) Applicant: Telemedicine Health, Inc., Weston, FL (US)

(72) Inventor: Daniel Gershoni, Weston, FL (US)

( * ) Notice: Subject to any disclaimer, the term of this patent is extended or adjusted under 35 U.S.C. 154(b) by 0 days.

(21) Appl. No.: 17/726,455

(22) Filed: Apr. 21, 2022

Related U.S. Application Data

(63) Continuation-in-part of application No. 16/530,022, filed on Aug. 2, 2019, now Pat. No. 11,311,460.

(60) Provisional application No. 62/715,930, filed on Aug. 8, 2018.

(51) Int. Cl.
| | | |
|---|---|---|
| *A61J 7/04* | (2006.01) | |
| *A61J 7/00* | (2006.01) | |
| *A61J 1/03* | (2023.01) | |
| *G16H 20/13* | (2018.01) | |

(52) U.S. Cl.
CPC .............. *G16H 20/13* (2018.01); *A61J 1/035* (2013.01); *A61J 7/0069* (2013.01); *A61J 7/0084* (2013.01); *A61J 7/0418* (2015.05); *A61J 7/0427* (2015.05); *A61J 7/0454* (2015.05); *A61J 7/0481* (2013.01);
(Continued)

(58) Field of Classification Search
CPC ......... G16H 20/13; A61J 1/035; A61J 7/0069; A61J 7/0084; A61J 7/0418; A61J 7/0427; A61J 7/0454; A61J 7/0481; A61J 2200/30; A61J 2200/70; A61J 2205/60
See application file for complete search history.

(56) References Cited

U.S. PATENT DOCUMENTS

| | | | |
|---|---|---|---|
| 4,953,745 A | | 9/1990 | Rowlett, Jr. |
| 5,047,948 A | * | 9/1991 | Turner .................. A61J 7/0436 221/9 |
| 5,507,277 A | | 4/1996 | Rubsamen et al. |
| | | (Continued) | |

FOREIGN PATENT DOCUMENTS

| | | |
|---|---|---|
| WO | WO2002011778 A1 | 2/2002 |
| WO | WO2002094234 A1 | 11/2002 |

*Primary Examiner* — Michael Collins
(74) *Attorney, Agent, or Firm* — Allen D. Hertz, P.A.; Allen D. Hertz

(57) ABSTRACT

A multi-tray medication dispensing apparatus and a method of use provides secure storage and dispensing of controlled substances and supplemental/alternative medication while providing remote assistance and monitoring. The apparatus includes at least two motorized medication trays for automatic dispensing of medication. Medication tray compartments can be filled manually or filled by inserting a prefilled blister pack containing sealed medication. The apparatus further comprises a secure tamper resistant housing, plurality of sensors, an optional reclamation safe, and a wireless communication module to notify remote operators of suspected illegal/unauthorized access. The apparatus can be configured in different form factors including, a portable desktop configuration, a wearable configuration designed for attaching to a person's wrist, arm, foot, etc. The apparatus can dispense a controlled substance or supplemental/alternative medication based upon a dispensing schedule and/or inputs from the user, wherein the supplemental/alternative medication is alternatively dispensed to control addition and/or proper use.

21 Claims, 54 Drawing Sheets

(52) U.S. Cl.
CPC ........ *A61J 2200/30* (2013.01); *A61J 2200/70* (2013.01); *A61J 2205/60* (2013.01)

(56) References Cited

U.S. PATENT DOCUMENTS

| | | | |
|---|---|---|---|
| 5,522,525 A | 6/1996 | Mclaughlin | |
| 6,439,422 B1 | 8/2002 | Papp et al. | |
| 6,848,593 B2 | 2/2005 | Papp | |
| 7,080,755 B2 | 7/2006 | Handfield | |
| 7,735,680 B2 | 6/2010 | Godlewski | |
| 7,844,362 B2 | 11/2010 | Handfield | |
| 7,952,315 B2 | 5/2011 | Park, IV | |
| 8,019,471 B2 * | 9/2011 | Bogash | G16H 20/13 700/242 |
| 8,060,249 B2 | 11/2011 | Bear et al. | |
| 8,548,623 B2 | 10/2013 | Poutiatine et al. | |
| 8,600,548 B2 * | 12/2013 | Bossi | A61J 7/0084 700/231 |
| 9,361,431 B2 | 6/2016 | Fauci | |
| 9,542,534 B1 * | 1/2017 | Ducatt | G07F 9/002 |
| 9,953,140 B2 | 4/2018 | McLean et al. | |
| 10,181,013 B2 | 1/2019 | Portney et al. | |
| 10,182,970 B1 | 1/2019 | Hassani et al. | |
| 10,296,719 B2 | 5/2019 | Ekin | |
| 11,311,460 B1 * | 4/2022 | Gershoni | A61J 1/035 |
| 2003/0052787 A1 | 3/2003 | Zerhusen | |
| 2006/0058724 A1 * | 3/2006 | Handfield | G07F 9/026 221/9 |
| 2006/0157491 A1 | 7/2006 | Whittle et al. | |
| 2007/0260491 A1 | 11/2007 | Palmer et al. | |
| 2008/0059228 A1 * | 3/2008 | Bossi | G16H 30/20 705/2 |
| 2008/0283542 A1 | 11/2008 | Lanka | |
| 2010/0305749 A1 | 12/2010 | Coe | |
| 2013/0284755 A1 | 10/2013 | Yuyama | |
| 2014/0244033 A1 * | 8/2014 | Ucer | A61J 7/0084 700/237 |
| 2015/0209237 A1 * | 7/2015 | Kim | G07F 17/0092 220/500 |
| 2017/0231870 A1 | 8/2017 | Stachler et al. | |
| 2018/0028408 A1 | 2/2018 | Li et al. | |
| 2018/0110939 A1 | 4/2018 | Lanzkowsky | |
| 2019/0080790 A1 * | 3/2019 | Patel | B65B 35/32 |
| 2019/0228850 A1 * | 7/2019 | Ramaci | G07F 9/002 |

* cited by examiner

NARCOTICS AND OPIOIDS SECURE STORAGE AND DISPENSING APPARATUS AND METHOD OF USE

CROSS-REFERENCE TO RELATED APPLICATIONS

This application is a Continuation-In-Part which claims the benefit of U.S. patent application Ser. No. 16/530,022, filed on Aug. 8, 2019, wherein U.S. patent application Ser. No. 16/530,022 claims priority to U.S. Provisional Patent Application Ser. No. 62/715,930, filed on Aug. 8, 2018, both of which are incorporated herein in their entireties.

BACKGROUND OF INVENTION

Field of the Invention

The invention is related to a device and its methods of use for a remote monitored, software assisted automated device providing secured storage, monitoring and delivering narcotics, Opioids, and/or other drugs. The narcotics and Opioids secure storage and dispensing apparatus provides a storage and dispensing mechanism which is tamper resistant in order to protect against illegal access to the contents. Plurality of motorized medication trays are being utilized in a synchronized motion in order to deliver the controlled medication and supplement medicine from a manually loaded medication tray as well as a sealed blister pack containing the controlled medication and other drugs.

Description of Prior Art

Each year, roughly 30,000 people die from Opioid overdose. In 2014, there were more Opioid overdose deaths compared to any other year. Until recently, the administration of this medication was reserved for use by only highly and qualified professionals such as doctors, nurses and other emergency personnel. However, in the last decade, there has been a significant push to having nonmedical individuals administer it to Opioid users in need and with good results.

Presently, there are various delivery methods available to patients to aid in decreasing the risk of Opioid overdose. The medication is administered by the conventional route which includes oral, intravenous, sublingual, etc. while audio instructions are provided on appropriate technique.

For instance, International Patent Application WO 2002011778 A1 to Wermeling describes an invention which relates to pharmaceutical drug compositions and preparations that are narcotic antagonists and analgesics, specifically Opioids. This invention also relates to pharmaceutical drug delivery devices, specifically to devices for the intranasal administration of drugs classified as controlled substances. Further, US Pre-Grant Publication 2018/0110939 A1 to Lanzkowsky also describes a method, system and apparatus for administering various medicaments including those for treating pain and substance dependency. The apparatus is a unit for heat activation of a morphine opiate liquid concentrate mixed with a carrier substance to produce inhaled gas. The method includes inhaling the heat activated gaseous vapor concentrate for pain relief, to treat substance dependency or administration of other medicaments.

Furthermore, International Patent Application WO 2002094234 A1 to Rabinowitz also describes an invention which relates to the delivery of Opioids through an inhalation route. Specifically, it relates to aerosols containing Opioids that are used in inhalation therapy. Moreover, US Pre-Grant Publication 2006/0157491 A1 to Whittle also describes an invention which relates to novel formulations, dosage forms and modes of delivery for treating patients addicted to a group of drugs which can result in dependencies and misuse.

Meanwhile, monitoring and control of the storage and dispensing device for Opioids and other drugs were also presented in various inventions.

For instance, U.S. Pat. No. 10,182,970 B1 to Hassani describes a secured and programmable medical dispenser which is configured to distribute medicine according to a schedule. The secured and programmable medical dispenser has a dispenser body mechanically coupled to a dispenser lid with a locking solenoid. A pill tube is arranged within the dispenser body and further has an open pill tube proximal end and a pill tube distal end. A microcontroller is attached to the dispenser lid, communicatively coupled to the pill release rotary solenoid and the liquid release rotary solenoid.

Another invention, described in U.S. Pat. No. 10,296,719 B2 to Ekin also describes an invention related to a smart pill dispenser which is used in a household, on a desktop, by keeping the different types of medication along with different dosages inside the container, which provides information to the user in order for the user to take his/her medication in time and in correct doses and which can inform the user interactively thru the use of smart devices such as cell phones, and smart watches.

U.S. Pat. No. 10,181,013 B2 to Portney also describes a pill dispensing system which includes an electronic mobile communication device with a wireless transmitter and receiver. A pill cartridge has a cartridge body storing a plurality of pills, where the cartridge body includes an electronic tag storing data. A pill cartridge dispenser is configured to receive at least one of the pill cartridges and configured to electromechanically control dispensing of the plurality of pills from the cartridge body, where the pill cartridge dispenser is configured to be in wireless communication with the electronic mobile communication device.

US Pre-Grant Publication 2018/0028408 A1 to Li describes in one embodiment, a medication dispensing device of a system for controlling and monitoring medicine dispensation includes means for securely containing a medication to be dispensed to a specific patient, confirm the identity of the patient, and to determine whether or not the patient is eligible to receive a dose of the medication at the time the dose is requested, only if the patient's identity is confirmed and the patient is eligible to receive the dose.

Further, U.S. Pat. No. 8,060,249 B2 to Bear also describes devices, systems, and methods for remote visualization of the storage compartments in a medication dispenser device, to monitor a patient's compliance with a medication dosage schedule and for verifying the proper loading of medication into the patient's medication dispenser device. The device may include a plurality of storage compartments, each having an interior space for storing at least one medication or medication reminder marker; an image capturing device (e.g., a camera) which can be positioned to capture an image of the interior space of each storage compartment; and a communications module for electronically transmitting the captured image to a central monitoring station.

Furthermore, U.S. Pat. No. 5,507,277 A to Rubsamen also describes a method of controlling access to a drug in an aerosol drug delivery device by an electronic lock and key means is disclosed. Access is limited to the intended user by providing the intended user with a uniquely coded, machine readable key means that matches the unique code of the lock means. Contacting matching lock and key means signals a controlling means to allow use of the device.

Additionally, US Pre-Grant Publication 2007/0260491 A1 to Palmer also describes a system for delivery and monitoring the administration of controlled substances which includes one or more databases including a national database of controlled substance users, a database including physician/pharmacy information, a controlled substance delivery device and a docking station for use together with a network and software for communication between the various components of the system.

In other important aspect in this field of invention, there are also patents which presented secure storage and dispensing drug device.

An example is U.S. Pat. No. 9,361,431 B2 to Fauci describes embodiments of the invention to provide safe, secure and accurate point-to-point delivery of prescription and non-prescription drugs in the long-term home care or ambulatory care environment. More specifically, embodiments of the present invention provide for a low-cost, easy-to-use system comprised of a secure drug dispensing unit and medication enclosure combined with wireless connectivity and software based on smart mobile phone technology. Such systems and methods, referred to herein as a Secure, Control, and Enhance Medication Adherence (SCEMA) system, can mitigate the aforementioned risks associated with the use of prescription and non-prescription drugs.

Another patent, U.S. Pat. No. 9,953,140 B2 to McLean, also describes a system, method, and apparatus for securely dispensing one or more prescribed substances at a given time and/or date. In certain embodiments, a pill dispensing device may include a generally tamper-proof portable housing. A replaceable cartridge may be configured to be disposed within the portable housing. The replaceable cartridge also may be generally tamper-proof. The portable housing and/or the replaceable cartridge may be operable to dispense a predefined amount of a prescribed substance at a given time and/or date.

Another example is disclosed in US Pre-Grant Publication 2017/0231870 A1 to Stachler, which discloses a medication storage and dispensing device having a biometric sensor to restrict access to the medication stored within. The device is locked to prevent access and includes tamper resistance features to prevent unauthorized access to the medication stored within. The device has wireless connection features that allow monitoring by medical professionals.

Also, U.S. Pat. No. 8,548,623 B2 to Poutiatine describes a dispensing devices and systems for oral transmucosal administration of small volume drug dosage forms to the oral mucosa. The dispensing device may be a single dose applicator (SDA), or an electromechanical device comprising a means for patient identification such as a wrist worn RFID tag and annular bidirectional antenna together with a lock-out feature.

Treatments of Opioids drugs are effective and needed continuous monitoring of the patient and their dosing time. Upon review of available patents presented earlier, there is no device providing continuous/intermittent administering, storage as well as monitoring of the patient. Further, the traditional method needs the presence of a conscious and caring bystander and physician. Continuous or near-continuous monitoring is necessary as it would allow the incidence of overdose or for remembering the dosing time, thereby increasing the odds of successful intervention. Unfortunately, these important features were not presented in currently available patents.

To solve the complex problem of prescription Opioid and heroin abuse in this country, one can recognize a need to control the prescribed Opioids from the moment of dispensing by the pharmacy to monitoring the use by the patient in real-time, to the reclamation and proper disposal of the unused pills by the dispensing pharmacy. It will also be advantageous to manage the safety of the Opioids while in the position of the users in such a way that unauthorized use, theft and inability to account for the prescribed Opioid will always be eliminated. It would be beneficial to provide a device and a method of use that impacts the Opioid problem that could be measured clinically, socially and environmentally in a way never done before.

It would also be beneficial to provide a device and a method of using the device which will be specially designed for people who are regularly on prescribed narcotics. It would be preferred that the device include a tamper-resistant casing with advanced software and video reporting technology, whereby the device will proactively monitor, record, and report narcotic usage. Further, it would be beneficial to provide a device that is wearable with an easy module, software assisted, automated with monitoring with audio and video facility for assistance by caregiver and physician.

BRIEF SUMMARY OF THE INVENTION

It is one object of the present invention to provide a remote monitored, software assisted narcotic dispensing device and methods of use for delivering and monitoring the Opioids and/or other drugs. Throughout the specification, the term Opioids is synonymous with the term Narcotics.

The narcotic dispensing device further includes a tamper resistant medication storage and dispensing mechanism to protect against illegal access to the Opioids contents.

The narcotic dispensing device additionally includes dual motorized medication trays that are synchronized in order to simultaneously deliver Opioids and other drugs including supplement medicine from the plurality of medication trays.

In one configuration of the narcotic dispensing device, Opioids and other drugs as well as supplemental medicine can be loaded into both medication trays manually and dispensed simultaneously.

In yet another configuration of the narcotic dispensing device, Opioids and other drugs and supplemental medicine can be loaded into both medication trays manually and dispensed with a time-offset from each other.

In yet another configuration of narcotic dispensing device, a sealed blister pack can be pre-loaded with Opioids and placed into one of the motorized trays, while other drugs and supplement medicine can be manually loaded into the second motorized medication tray. The two motorized medication trays can then be programmed to dispense medicine simultaneously or at a time-offset from each other.

Another feature of the narcotic dispensing device includes one or more sensors placed at a push out passage opening that can detect when an object such as human hand is placed under an exit compartment. When the object is placed under the exit compartment, the at least one sensor would trigger a motorized mechanism to rotate one or both of the motorized medication trays containing the Opioids and other drugs to position the next dosage of pills at the passage opening to be dispensed.

The narcotic dispensing device may further include at least one biometric sensor to detect and authenticate a presence of an authorized user before allowing for the medications to be dispensed. The at least one biometric sensor provided may include, but is not limited to, a fingerprint scanner, a retina scanner, a facial recognition system, and a voice recognition system.

The narcotic dispensing device may further include a wireless Near Field Communication (NFC) circuit to detect and authenticate a presence of the authorized user before allowing dispensing of the medications.

The narcotic dispensing device may further include a display unit that provides information related to the medications to be taken, including but not limited to: reminder messages, instructions on the medications and how to take them, as well as actual images of the medications related to each dose of medication.

The locking mechanism of the narcotic dispensing device may be additionally equipped with series of electronic sensors that detect tampering with the device. In case tampering occurs, the narcotic dispensing device will enter into a special, restricted alert mode and notify the user via audible alarms as well as notifying the remote operators and caregivers utilizing the built-in Wireless module.

The narcotic dispensing device may further include a camera, a microphone and speaker set to allow live audio and video communication with caregivers, physicians, and remote call-center operators, as well as for audio and video communication to operate the dispenser of the present invention.

The narcotic dispensing device further provides a unique and novel approach for monitoring and dispensing methods including a multi-layer authentication and validation of the authorized user prior to dispensing the Opioids.

The narcotic dispensing device additionally provides a novel punching mechanism that utilizes a dual punching process consisting of a linear motion followed by a rotational movement of an armature shaft to puncture the sealed blister pack and release the containing medicine.

The narcotic dispensing device may further include a weight scale for measuring and validating the amount of Opioids present in each compartment of the two medication trays.

In yet another configuration, the narcotic dispensing device can be made waterproof.

The narcotic dispensing device may further include a separate portable dispensing unit including but not limited to a wristband as well as an ankle bracelet to be used to dispense Opioids and other drugs when away from main dispensing device.

The portable dispensing unit of the present invention may further include one or more compartments for securely storing and dispensing Opioids.

Each of the portable dispenser device compartments can be remotely monitored and programmed to unlock and release medicine.

In one configuration, the portable dispensing unit can take the form of a wristband.

In one configuration, the portable dispensing unit can take the form of a bracelet.

In yet another configuration, the portable dispensing unit can take the form of an ankle bracelet.

The narcotic dispensing device may further include a docking compartment for the portable dispensing unit to mate with it and securely transfer one or more Opioid dosages from the main dispensing unit to the portable unit. The main, secure narcotic dispensing device, utilizes a series of wireless and wired sensors to authenticate the portable dispense unit mating with it and securely release Opioids and other drugs form one or both of the dispense trays into the portable dispense unit compartments.

The narcotic dispensing device addresses the problems in the art and advances the state of the relevant technology with a variety of new features and capabilities that innovate over and significantly enhance prior devices in new and novel ways. In one of the many preferable configurations, the present invention contemplates medication compliance, monitoring, and protection of device with illegal or unauthorized use that includes, among other features and elements a blister pack formed with unit dose compartments in device, which can be formed like the blister packs well-known to those skilled in the relevant arts. Several aspects of the present invention described herein reference Opioid drugs; however the present invention may also be used for drugs other than Opioid drugs and should not be limited to only Opioid drugs.

In the main aspect, a device is provided for administering, storing and monitoring of Narcotics, Opioids and other drugs includes a microprocessor, a memory, a wireless transceiver, an interface display, a microphone, a speaker, multiple sensor mechanism, a motorized mechanism, a dispensing mechanism, a monitoring protocol, an accommodation for a blister-pack, a punching armature.

In one configuration, the device will further comprise a mobile device such as a smart phone or tablet computer to provide interactive assistance to the user while wirelessly notifying the remote operators of the status of the device and Opioid dispenses.

In the main aspect, the present invention relates to a self-programmable wireless device for administering, storage and monitoring system, including but not limited to a form of a bracelet for Narcotics, Opioids and other drugs. More specifically, the present invention relates to secure storage and dispensing of Opioids and other medications with a built-in intelligence and its capabilities to meet an individual patient's needs and monitoring.

In main aspect, a method for dispensing an Opioid or another drug comprises:
   a. In one configuration, the device is a stand-alone unit.
   b. In yet another configuration, the device is placed on the wrist, ankle or other parts of a human body.
   c. In yet another configuration the device includes a compartment for blister packs for Opioids and other drugs and capable of dispensing a plurality of pills from a pre-sealed container such as a blister pack to a collector at pre-programmed dispense time, a capability to record a date and time of each dispensed dosage and provide a system for tracking medication compliance.

In the main aspect, the device dispenses the Narcotics, Opioids and other drugs from a motorized tray contain manually inserted medication.

In yet another aspect, the device dispenses the Narcotics, Opioids and other drugs from a sealed container such as a Blister-Pack unit placed in the secondary motorized medication tray.

In yet another aspect, the device dispenses the Narcotics, Opioids and other drugs from both manual tray and a sealed blister-pack container simultaneously.

In yet another aspect, the device dispenses the Narcotics, Opioids and other drugs from both manual tray and a sealed blister-pack container with a pre-programmed time delay between the two medication dispensing. This novel concept allows users to have multiple medications at one or more intervals during each day.

In one aspect motorized mechanism is used for rotatable positioning of the blister pack stepwise relative to the part of the device including the push-out means. The optical sensor detects the presence of an object such as a person's hand at the passage opening and allows the Narcotics, Opioids and other drugs pills to be dispensed automatically.

In another aspect, the present device has an alarm with the ability to alert the prescriber, medical care providers, caregivers or other persons, to whom notification is desired of unauthorized access, dispensing of drugs, or security breach, Narcotics, Opioids and other drugs.

In another aspect, the device may further include a camera, a microphone, and a speaker set to allow live audio and video communication with caregivers, physicians and remote call-center operators, and for audio and video communication to operate the dispenser of the present invention.

In one aspect, the device comprises of a tamper proof casing with plurality of sensors as well as wireless communication module to notify if the device has unauthorized access or has been forced open. The communication module includes but are not limited to Wi-Fi, Cellular (such as 3G, 4G, 5G, or any other cellular technology), and Bluetooth.

In one aspect, the tamper proof casing comprised of dual motorized locking mechanisms to ensure secure access to the plurality of medication tray access covers. A centralized locking mechanism is utilized to anchor the top housing cover for the inner medication tray containing the manually loaded medication, while a plurality of sliding shafts placed in the inner medication tray's access cover extend out into the matching openings in the outer medication tray access cover to securely lock the two rotary medication tray covers together.

In another aspect, the device has the capability for transmitting an alarm signal in case of unauthorized access, illegal dispensing of drugs, or security breach of the device to communicate, including but not limited to audio and or visual communication with a monitoring center, the user, caregiver, physician, and/or others via cellular communication.

In another aspect, the device communicates data, utilizing communication modules, including but not limited to Wi-Fi, Cellular (such as 3G, 4G, 5G, or any other cellular technology), Bluetooth, Radio Frequency (RF technology), wired communication, and other available means. Due to the subject matter of the communications, it is preferred that the communications are encoded to maintain privacy.

In another aspect, the present invention uses a biometric system for verifying the prescribed user, caregiver, physician, and other authorized users. The biometrics sensors used in the device including but are not limited to a fingerprint scanner, a facial recognition video acquisition system, a retina scanner, and the like, for secure access to the device.

In another aspect, the device includes a Global Positioning System (GPS) locating capability allowing the location of the device to be sent out to remote monitoring centers as well as to the Emergency Medical Technician (EMT) service in case of emergency. In other embodiment, the device is also enabled with "Location Lock" e.g., a feature which identifies weather the device in a designated location has been moved and "Track Me" e.g., a feature which enables an interested party or person to locate the device and to notify if the device has been moved illegally without authorization.

In another aspect, the device also has built-in motion detection feature to notify caregiver and user if the device is moved, fallen, and damaged due to sudden movement or drops. The motion detection feature is utilized through use an accelerometer as well as other means.

In another aspect, the device has connectivity to a social networking support group for assistance, information access, and notification.

In another aspect, the device includes a display, a microphone, a speaker, and a camera for verification and remote care by a medical care provider, prior to administration of a urine test for taking the Opioid pills or other drugs. Remote caregivers or physician can interactively engage the user utilizing the display, microphone, speaker, and camera to ensure proper steps are taken prior to dispensing the Opioids or other drugs and to conduct proper diagnostics testing such as urine, electrocardiogram (ECG), blood pressure, etc.

In another aspect, the device is also utilized for real-time communication to provide assistance with caregiver, supervisor, and as well as rehabilitation personnel, mental health personnel, family support providers, and others.

In another aspect, the device may further include a built-in thermometer with user contact points for measuring body temperature. The display unit provides the temperature reading locally while the communication module transmits that information to remote operators, caregivers, physicians and family members. The means of communications includes but is not limited to Wi-Fi, Cellular (such as 3G, 4G, 5G, or any other cellular technology), Bluetooth, wired communication, and other available means.

In another aspect, the device may further include a built-in electrocardiogram (ECG) sensor with user contact points for measuring the user's pulse and or other cardiovascular activities. The storage unit provides local storage for recorded electrocardiogram (ECG) waveforms. The electrocardiogram (ECG) recordings are shown on the display unit, while the communication module transmits that information to remote operators, caregivers, or others. The means of communications include but are not limited to Wi-Fi, Cellular (such as 3G, 4G, 5G, or any other suitable cellular protocol), Bluetooth, wired communication, and other available means.

In another aspect, the present invention may further include the feature of a code scanner, including but not limited to barcodes, for scanning medication labels to assist with the verification and adherence process. The code scanning process can also be achieved by connecting the device to an external code scanner via one of the available communication means, including but not limited to a Universal Serial Bus (USB) circuit, Bluetooth, or Wi-Fi.

In another aspect, the present invention utilizes a scale to monitor Opioids being dispensed. This may also be used to assure the return of all unused Opioids to the prescribing pharmacy for proper dispensing. This will further help against unused Opioids finding their way to the illegal Opioid market.

In another aspect, the device includes a unique "Check-On-Me" feature, that comprises a button that when pressed, will communicate wirelessly with outside computers, mobile devices and remote caregivers and operators by sending various electronic signals and messages to alert them of status of the user.

In another aspect, the present invention may include and employ a cabinet/docking station made up of tamper resistant materials including but not limited to heavy duty plastics and/or metal, a communication module, a battery backup alarm, a biometric sensors, a cabinet alarm, and a cabinet utilization logs. For improved connectivity the present invention may also include a cellular booster antenna. This embodiment is particularly useful for the identification, dispensing and storage of Narcotics, Opioids and other drugs in a rehabilitation centers, or other medical facilities with more than one patient. Further, the camera is useful for visual verification of the caregiver or other person assisting in the dispensing of the Opioids or other drugs, and for monitoring the user's ingestion of the Opioids and or other drugs.

In another aspect, the present invention includes a capability for validation and authentication of user ingesting Opioids and/or other drugs by utilizing an infrared camera as well as other comparable means, including but not limited to biometric sensors.

In another aspect, the present invention includes a capability for validating and monitoring whether Opioids and or other drugs were ingested by an authenticated user. This may be performed through the use of an infrared camera and wireless sensors placed on an edible housing for the "Opioid and/or other drugs".

In another aspect, the removable dispensing tray is automated to drop the Opioids and/or other drugs into the removable dispensing tray after biometric verification of the intended authorized users. The removable dispensing tray may further include a biometric sensor to release the Opioids and/or other drugs to the users.

In another aspect, one or more secure Opioid dispensers are stored in a storage cart with trays, shelves, and other storage compartments to house each Opioid dispenser. The trays, shelves, and/or other storage compartments of the Opioid dispensers may be identified by barcode scanning, RFID, Bluetooth, Wi-Fi, Wireless cellular technology, wired connection, such as USB connection, or other means.

In another aspect, one or more secure Opioid dispensers are stored in a storage docking station with one or more docking platforms for narcotics and Opioids secure storage and dispensing apparatus placement. The narcotics and Opioids secure storage and dispensing apparatuses placed in the docking station may be identified by barcode scanning, RFID, Bluetooth, Wi-Fi, Wireless cellular technology, wired connection, such as USB connection, or other means.

In another aspect, the present invention includes a weight scale, wherein the weight scale is utilized for monitoring Opioids dispensing from the blister pack by constantly or periodically monitoring the weight of the blister pack and/or its contents placed inside the dispenser.

In another aspect, the present invention includes Optical Sensors, wherein the optical sensors are used for detecting the presence of Opioids in the blister pack. The narcotics and Opioids secure storage and dispensing apparatus will utilize sensors including but not limited to optical sensors and photo sensors to detect a presence of Opioids in each compartment of the blister pack. The blister pack is made up of transparent to partially transparent material with a reflective material used as a seal, wherein the reflective material may be, but is not limited to, aluminum foil. Sensors will be placed under one or more sealed storage compartments of the blister pack as placed in the narcotics and Opioids secure storage and dispensing apparatus. Once the Opioids are removed from one or more compartments of the Blister Pack, The sensors will detect and report that to an intended recipient, such as remote operators, caregivers, or others.

In another aspect, the present invention utilizes optical sensors to detect the presence of Opioids from a revolving medication storage tray inside the narcotics and Opioids secure storage and dispensing apparatus. The narcotics and Opioids secure storage and dispensing apparatus will utilize sensors including but not limited to optical sensors and photo sensors to detect the presence of Opioids in each compartment of the storage medication tray. Once the Opioids are removed from one or more compartment of the storage tray, the sensors will detect and report that to an intended recipient, such as a remote operator, a caregiver, or another intended party.

The following further describes the novel features of the invention:

The present invention, a narcotics and Opioids secure storage and dispensing apparatus, provides for secure storage and dispensing of Opioids and other medications. The narcotics and Opioids secure storage and dispensing apparatus also utilizes an access cover, which is tamper resistant, and uses one or more sensors to notify if the device has unauthorized access or has been forced open. The device is capable of verifying that medication is taken by the prescribed user via utilizing biometrics, including but not limited to, a retina scan process, a facial recognition process, and/or a fingerprint scanning process of the authenticate user.

Moreover, when a urine test is required prior to taking the Opioid, the narcotics and Opioids secure storage and dispensing apparatus can provide verification by a care provider prior to the user's ability to ingest the Opioid. Remote caregivers can also interactively engage with the user utilizing the display, the microphone, the speaker, and/or the camera to ensure proper steps are taken prior to dispensing the Opioids. Also, the narcotics and Opioids secure storage and dispensing apparatus can further provide verification that the Opioids are securely stored and are only accessible to the user via multiple authentication means including providing video images as well as various biometric methods, including but not limited to facial recognition, a fingerprint scan and/or a retina scan.

Also, the narcotics and Opioids secure storage and dispensing apparatus can further provide information on the location of the medication in relation to the prescribed user for further security and validation of use by the prescribed user. The narcotics and Opioids secure storage and dispensing apparatus can further provide ability for local and remote operators to be alerted, when unauthorized dispensing is attempted. The narcotics and Opioids secure storage and dispensing apparatus has wireless communication modules including not limited to Wi-Fi, Cellular (3G, 4G, 5G), Bluetooth, and other available means, to alert remote operators, caregivers, law enforcements, and other intended recipients.

Furthermore, the narcotics and Opioids secure storage and dispensing apparatus additionally includes an alarm system notifying of an attempt to extract the Opioids and or other drugs forcefully from the secure dispensing device. Various sensors are used to indicate any tampering with the device. It also provides the ability to alert the care providers or other intended parties of a security breach.

Meanwhile, the narcotics and Opioids secure storage and dispensing apparatus further provides an ability to notify law enforcement of an attempt to steal Opioids and/or other drugs from the device. The narcotics and Opioids secure storage and dispensing apparatus further provides the ability to provide care providers, law enforcement, an/or other persons a GPS location of the prescribed user and the dispensing device, so that an assumption can be made as to who is attempting to extract the Opioids and/or other drugs without authorization.

The narcotics and Opioids secure storage and dispensing apparatus further provides an ability to transmit an alarm signal using various wireless communication methods. The means of communications includes but not limited to Wi-Fi, Cellular (3G, 4G and 5G), Bluetooth, wired communication, and other available means. Also, it provides the ability to sound an alarm on the device and/or remotely. The narcotics and Opioids secure storage and dispensing apparatus further provides the ability to communicate with the user via cellular communication. The narcotics and Opioids secure storage and dispensing apparatus can also communicate with the user via video.

Additionally, the narcotics and Opioids secure storage and dispensing apparatus also provides the ability to use a video camera to verify that the user has taken the dispensed Opioids and or other drugs. The narcotics and Opioids secure storage and dispensing apparatus also provides an ability to verify the return of all unused Opioids and/or other drugs to the prescribing pharmacy for proper dispensing (eliminating those unused Opioids from finding their way to the illegal Opioid market). The narcotics and Opioids secure storage and dispensing apparatus can include multiple cameras to record activity associated with the apparatus. One or more cameras can be located about a peripheral edge and/or upper surface of the narcotics and Opioids secure storage and dispensing apparatus to acquire images recording access and ingestion of the dispensed medication, any interaction with the narcotics and Opioids secure storage and dispensing apparatus, and any other movements occurring in a proximity of the narcotics and Opioids secure storage and dispensing apparatus. One or more cameras can be located on a bottom of the narcotics and Opioids secure storage and dispensing apparatus, preferably at a location proximate the medication dispensing location of the narcotics and Opioids secure storage and dispensing apparatus. The bottom located camera(s) can record video of the process dispensing the medication to the user. The video cameras can also be used for bio-recognition of the user. This can include facial recognition, iris recognition, or any other suitable application. Also, the narcotics and Opioids secure storage and dispensing apparatus provides for secure access to the dispensing device by an authorized pharmacy only.

The narcotics and Opioids secure storage and dispensing apparatus also provides support for sealed blister pack storage, dispensing, and reclamation. It also provides support for remote release of the Opioids and/or other drugs by an approved party or person, including but not limited to a healthcare provider. The narcotics and Opioids secure storage and dispensing apparatus further provides support for real-time supervision utilizing cameras, two-way audio, and wireless technology. The narcotics and Opioids secure storage and dispensing apparatus further provides support for real-time remote diagnostics testing such as urine, electrocardiogram (ECG), blood pressure etc. It also provides support for real-time communication through "Sally's Help Button" (panic button/PERS), in case the user needs safety and/or support assistance, with rehabilitation center, mental health providers, family support providers, and or other support systems, including but not limited to an emergency contact.

Moreover, SDDO also provides support for secure Biometric access to ensure proper identification, including but not limited to retina, fingerprint, facial, voice recognition, and/or other means. It further provides support for authentication for secondary access. The authentication maybe performed through use of an RFID and/or other means. It also utilizes a scale and/or other sensor for monitoring the stored contents, including but not limited to an optical sensor. This can help to ensure that the proper medication amount was stored and dispensed. This also guards against unauthorized tampering and removal of contents.

The present invention further utilizes a touchpad for the electrocardiogram (ECG) and/or Thermometer sensors. It also utilizes GPS tracking for location monitoring.
  a. On the wearable model, said GPS tracker will provide monitoring of the user and the device.

Furthermore, narcotics and Opioids secure storage and dispensing apparatus provides "Location Lock" and "Track Me" features to notify if device has moved. It utilizes motion sensors including but not limited to an accelerometer to detect movement falls, and damages due to sudden movement or drops. It further provides Connectivity to social networking support group.

In another embodiment, Mobile narcotics and Opioids secure storage and dispensing device can be configured as a wearable device to store and dispense Opioids and or other drugs. The Mobile narcotics and Opioids secure storage and dispensing device may be configured to attach to a person's wrist, arm, foot, or other body parts. The Mobile narcotics and Opioids secure storage and dispensing device may further be configured as a Personal Opioids Emergency Response System (POERS) Mobile version of the narcotics and Opioids secure storage and dispensing apparatus. The Mobile narcotics and Opioids secure storage and dispensing device may utilize a pulse and/or electrocardiogram (ECG) sensor. The Mobile narcotics and Opioids secure storage and dispensing device may further utilize a thermometer, motion sensor, panic button, and/or a biometric sensor, including but not limited to a fingerprint scanner.

The narcotics and Opioids secure storage and dispensing apparatus can include a storage location that contains a suspected overdose counteracting drug. The storage location can be accessed via a remotely operated access mechanism, such as a remotely operated door. In a suspected overdose, the user can activate a panic button. Upon activation, the intelligence in the narcotics and Opioids secure storage and dispensing apparatus can operate the access mechanism. Alternatively, the narcotics and Opioids secure storage and dispensing apparatus can contact a remote monitoring party, where the remote monitoring party can access the situation and determine whether dispensing of the suspected overdose counteracting drug is appropriate. In a condition where the remote monitoring party determines that the condition warrants, the remote monitoring party proceeds with sending a direction to the narcotics and Opioids secure storage and dispensing apparatus to dispense the suspected overdose counteracting drug from the cavity.

In another aspect, the narcotics and Opioids secure storage and dispensing apparatus can include a medication staging station and a dispensing mechanism. In operation, the narcotics and Opioids secure storage and dispensing apparatus can prestage the medication for dispensing within the staging station, The medication would remain in the staging area until one of two conditions:
  (a) dispensing of the medication is appropriate. This can be based on a scheduled time for dispensing, a request by the user for dispensing of the medication, a request by the user for dispensing of the medication that is approved by an authorizing process (either the system or a decision by an authorized person), or any other acceptable condition,
  (b) dispensing of the medication is determined to be inappropriate. In this condition, the staged medication can be forwarded to a medication reclamation safe. Conditions can include when a time window for dispensing has lapsed without a request for dispensing of the medication, the user fails to meet criteria suitable for prescribing taking of the medication, or any other scenario where it would be determined inappropriate for the user to take the medication. In one scenario of this condition, it could be determined to reclaim the primary medication and dispense the supplemental medication, wherein the primary medication would be transferred to the medication reclamation safe and the supplemental medication would be staged for dispensing.

These and other aspects, features, and advantages of the present invention will become more readily apparent from the attached drawings and the detailed description of the present invention, which follow.

BRIEF DESCRIPTION OF THE DRAWINGS

A clear understanding of the key features of the invention summarized above may be had by reference to the appended diagrams/flow charts, which illustrate the method and system of the invention, although it will be understood that such diagrams/flow charts depict preferred embodiments of the invention and, therefore, are not to be considered as limiting its scope with regard to other embodiments which the invention is capable of contemplating. Accordingly.

DETAILED DESCRIPTION OF THE PREFERRED EMBODIMENTS

Figure 1:
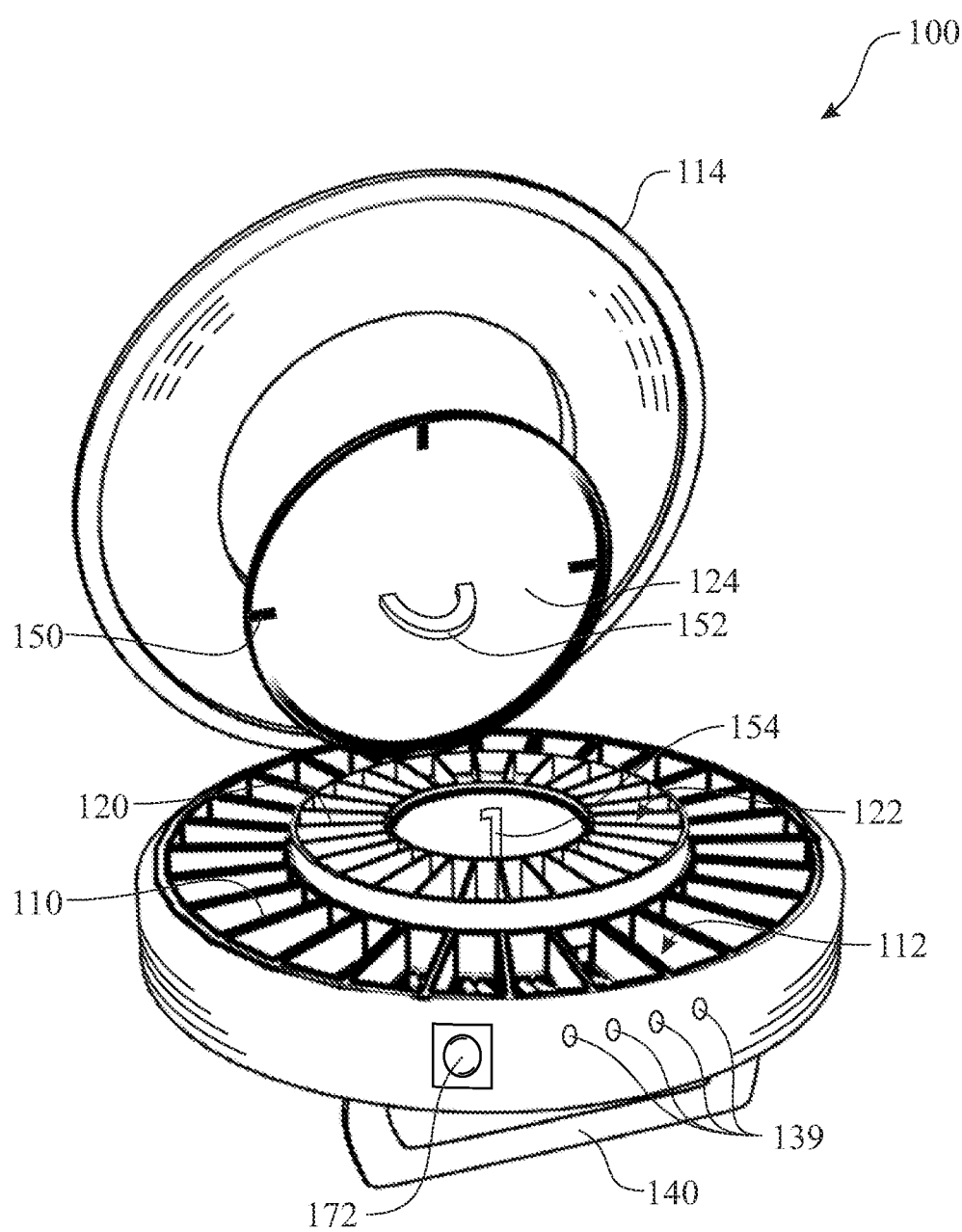
FIG. 1 presents a top, front right side, isometric view of an exemplary narcotics and Opioids secure storage and dispensing apparatus comprising two trays, the illustration presenting each of both trays open.

Detailed embodiments of the present invention are disclosed herein. It will be understood that the disclosed embodiments are merely exemplary of the invention that may be embodied in various and alternative forms. The figures are not necessarily to scale, and some features may be exaggerated or minimized to show details of particular embodiments, features, or elements. Specific structural and functional details, dimensions, or shapes disclosed herein are not limiting but serve as a basis for the claims and for teaching a person of ordinary skill in the art the described and claimed features of embodiments of the present invention. The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

It should be noted that references to "an," "one," or "various" embodiments in this disclosure are not necessarily to the same embodiment, and such references contemplate more than one embodiment.

The present invention disclosed herein is a contactless automatic pill dispenser configured to remind a user and to dispense medication to the user, and to provide a system for tracking medication compliance.

Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized current good manufacturing practice guidelines.

As used herein the term "computing device"" includes a desktop, laptop or tablet computer, as well as a mobile device or any other functionally similar device.

As used herein, the terms "patient," "care giver," "user," and the like all refer to the person who is using the present invention and are meant to be interchangeable and non-limiting.

"Telemetry" refers to any wireless transmission and reception of measured quantities for the purpose of remotely monitoring environmental conditions or equipment parameters.

"Software Application" refers to all computer software that causes a computer to perform useful tasks beyond the running of the computer itself.

Disclosed herein and illustrated in FIGS. 1 through 43 is a narcotics and Opioids secure storage and dispensing apparatus 100 (alternatively referred to as a multi-tray medication dispensing apparatus), a method of using the narcotics and Opioids secure storage and dispensing apparatus 100, ancillary devices associated with the narcotics and Opioids secure storage and dispensing apparatus 100, and methods of using the ancillary devices associated with the narcotics and Opioids secure storage and dispensing apparatus 100 in accordance with the present invention.

Figure 2:
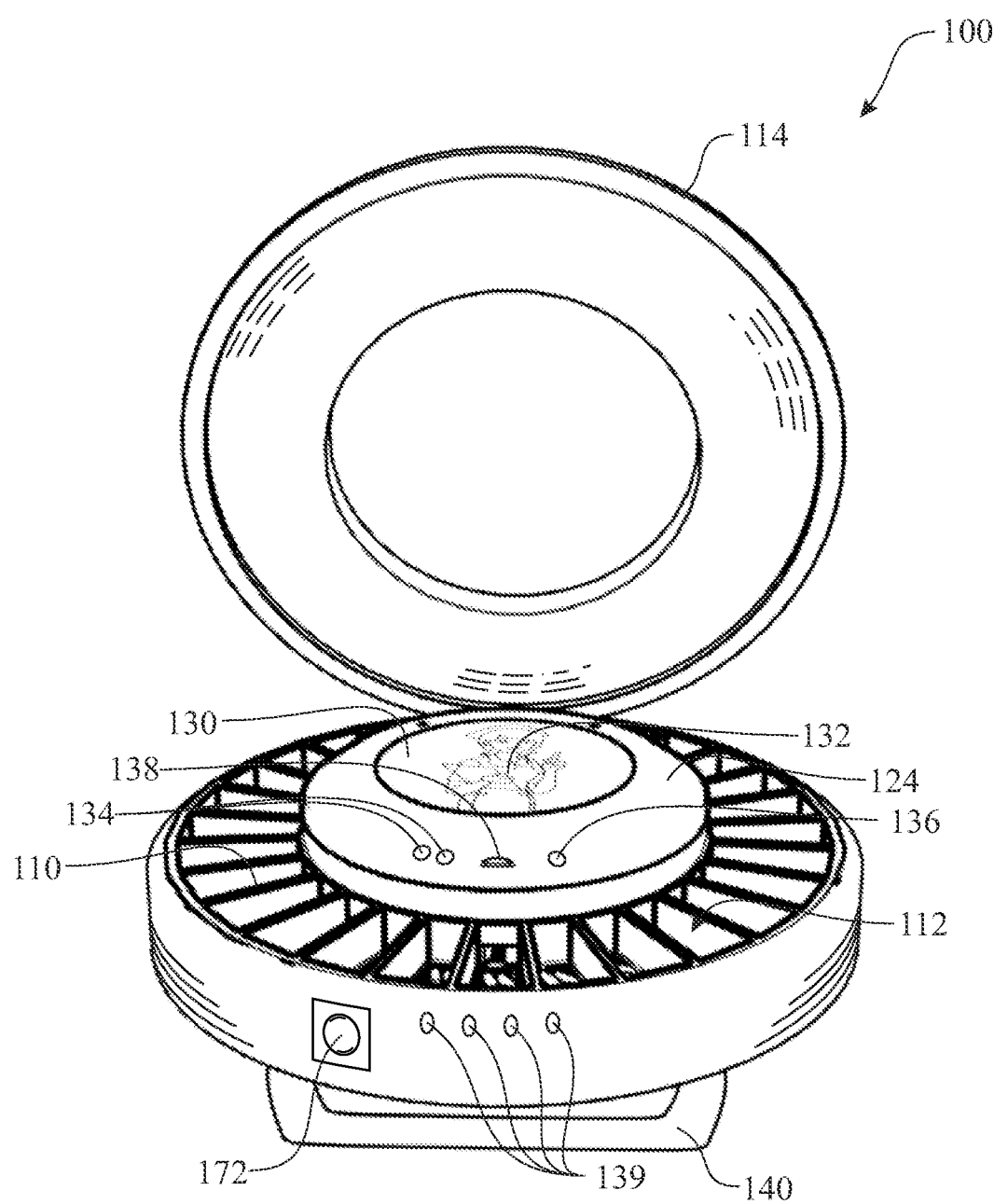
FIG. 2 presents a top, front isometric view of the narcotics and Opioids secure storage and dispensing apparatus as originally introduced in FIG. 1, the illustration presenting the primary tray being the only open tray.
Figure 3:
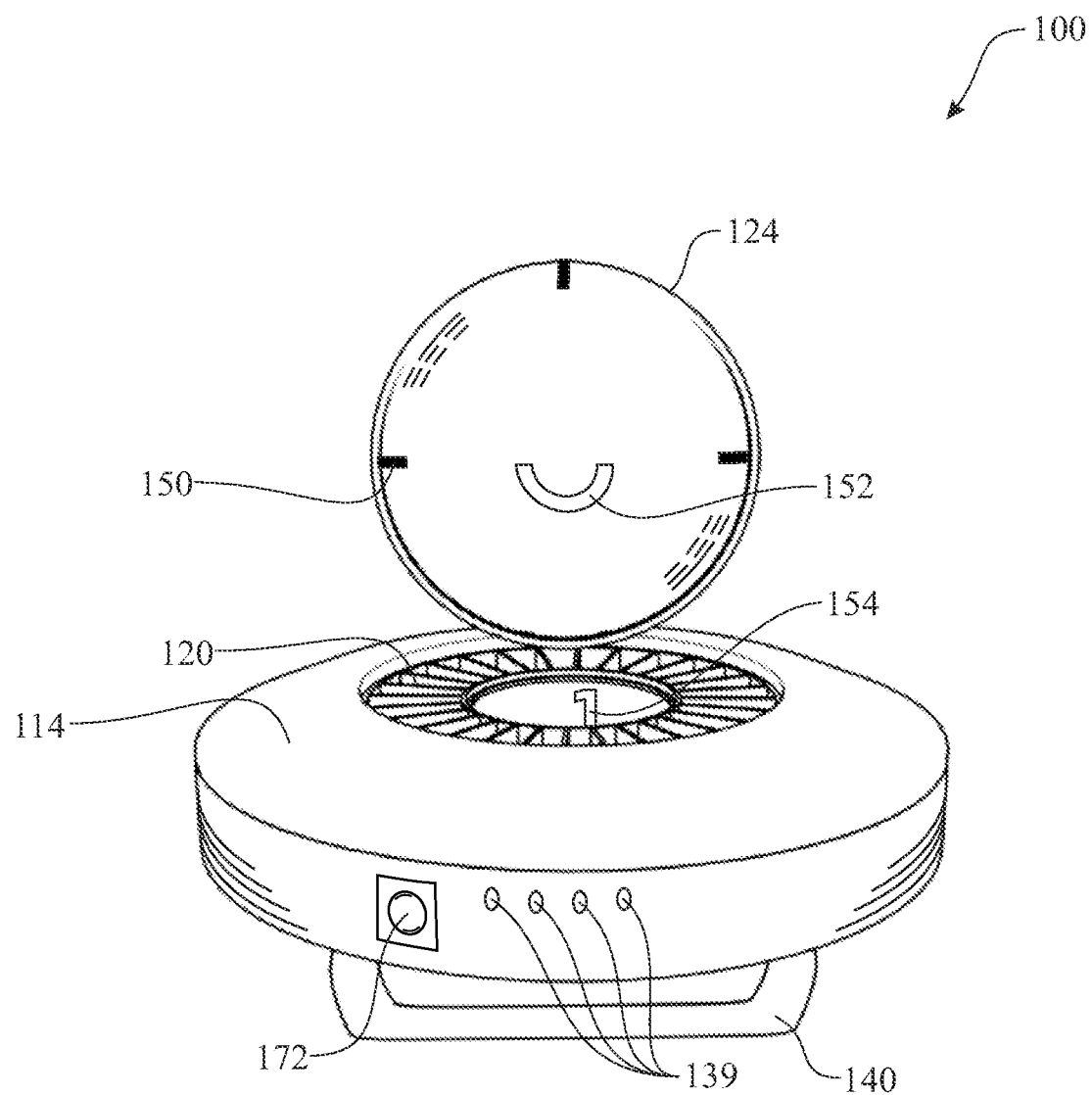
FIG. 3 presents a top, front isometric view of the narcotics and Opioids secure storage and dispensing apparatus as originally introduced in FIG. 1, the illustration presenting the secondary tray being the only open tray, the illustration also presenting legs in an extended configuration.
Figure 4:
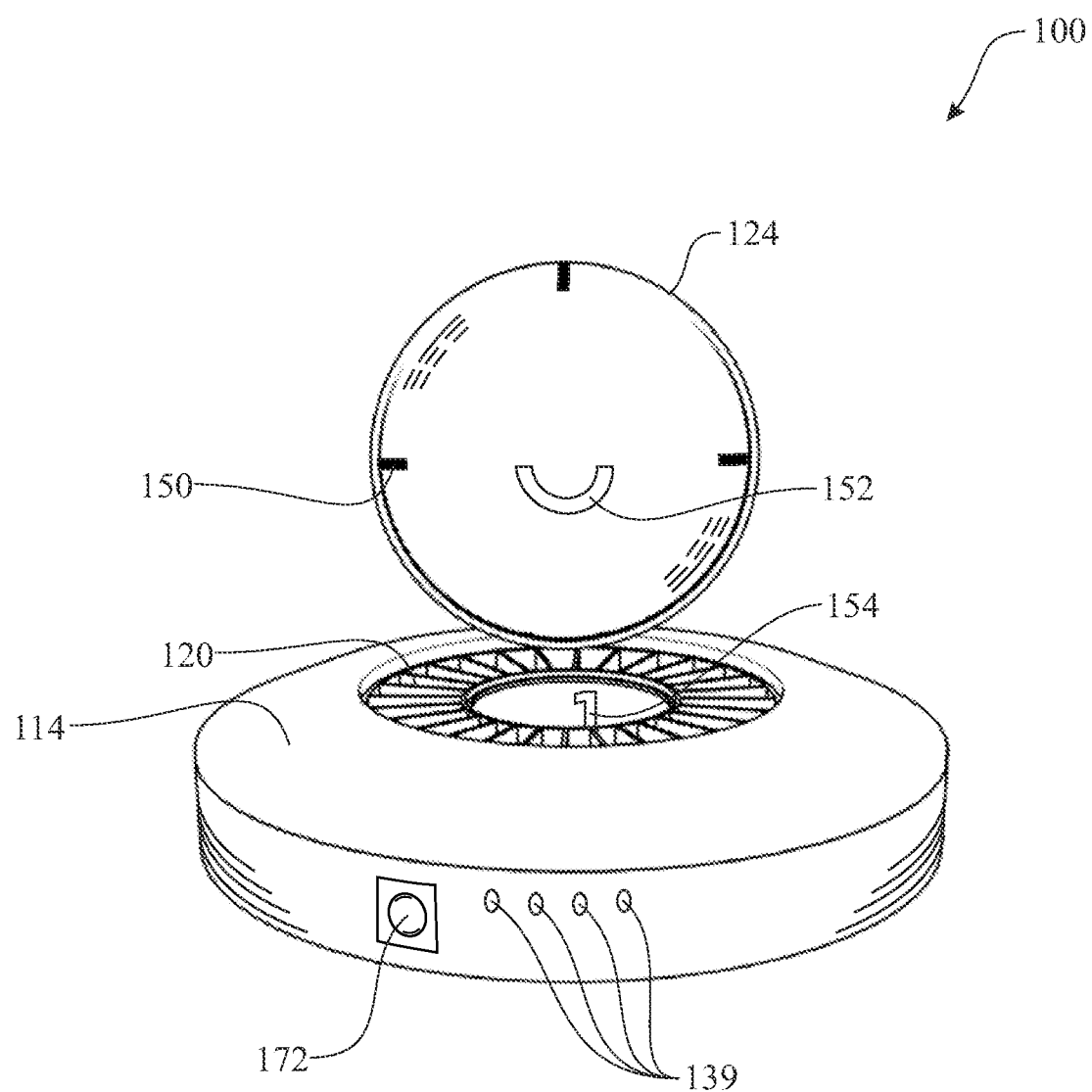
FIG. 4 presents a top, front isometric view of the narcotics and Opioids secure storage and dispensing apparatus as originally introduced in FIG. 1, the illustration presenting the secondary tray being the only open tray, the illustration also presenting the legs in a closed configuration.
Figure 5:
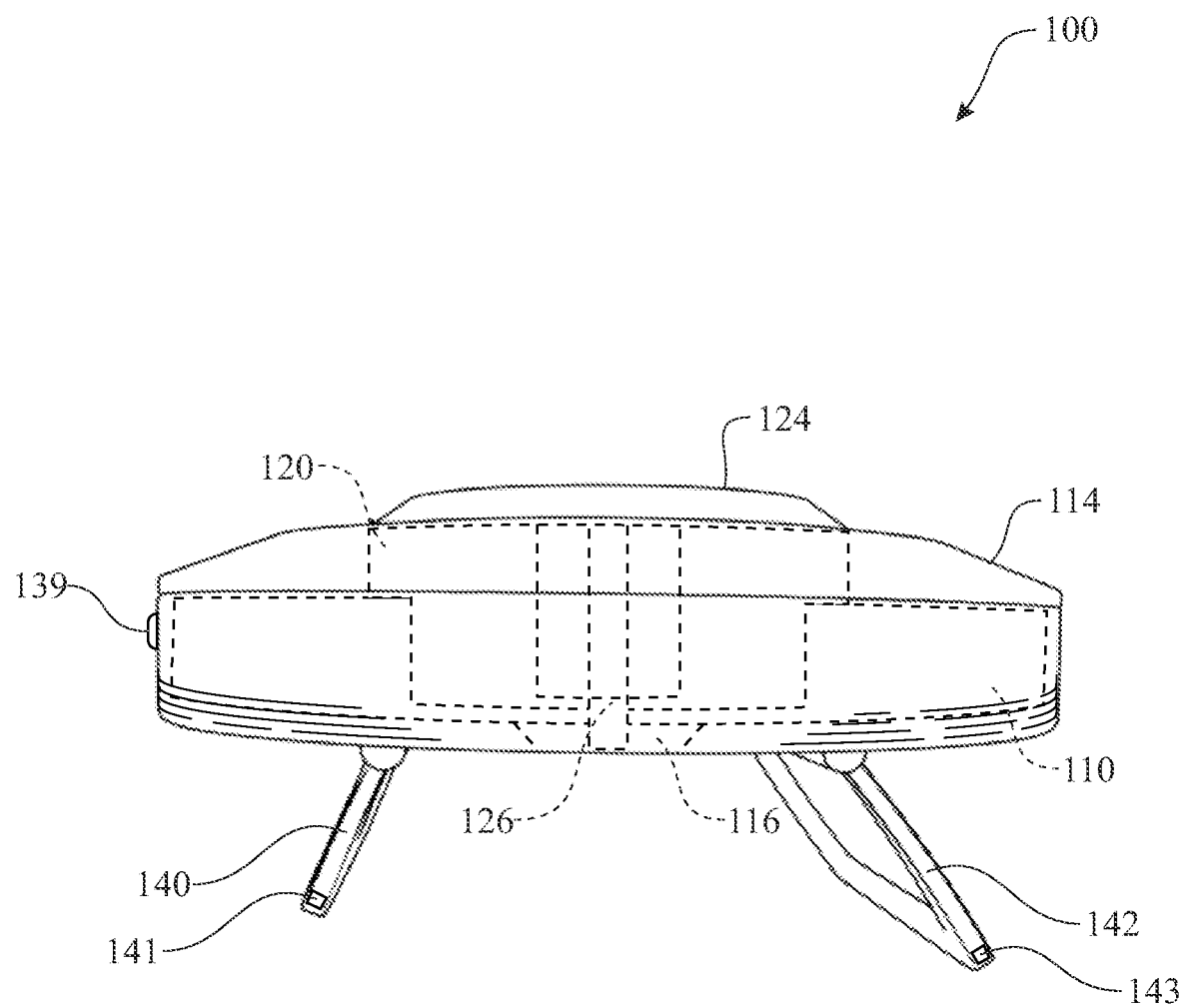
FIG. 5 presents a left side elevation view of the exemplary narcotics and Opioids secure storage and dispensing apparatus as originally introduced in FIG. 1, the illustration presenting both trays closed and both legs in an extended configuration.
Figure 6:
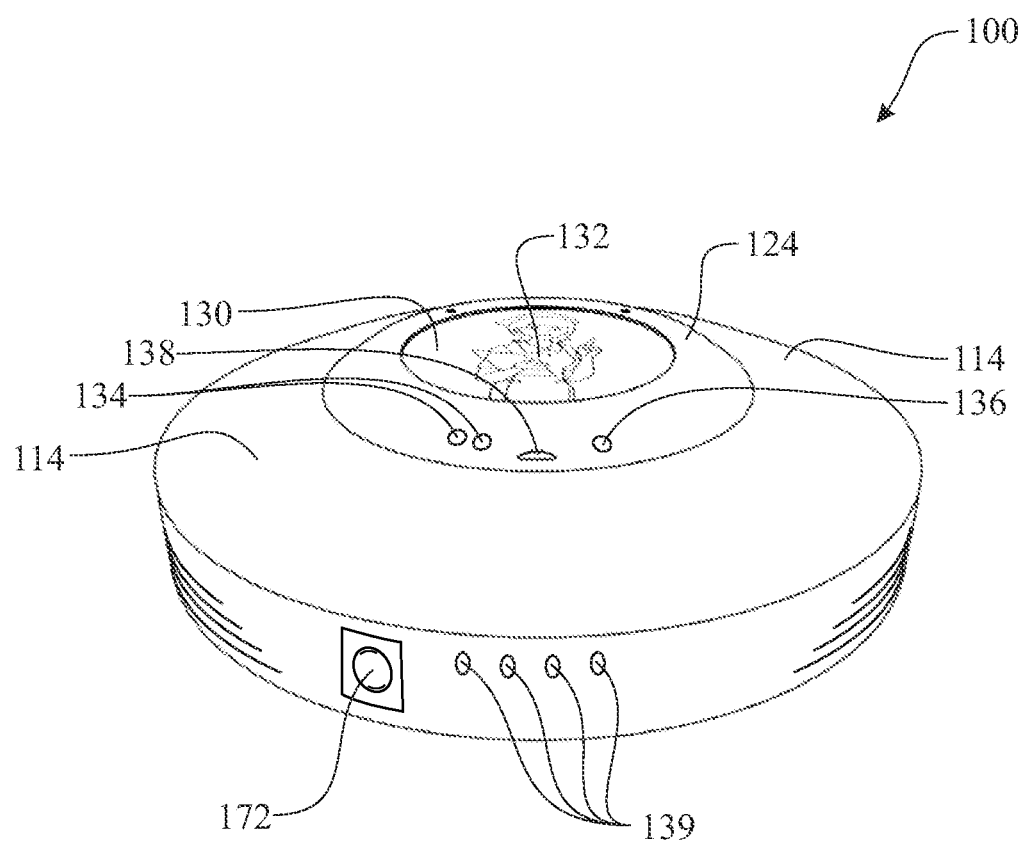
FIG. 6 presents a top, front isometric view of the exemplary narcotics and Opioids secure storage and dispensing apparatus as originally introduced in FIG. 1, the illustration presenting both trays in a closed configuration and both legs in a retracted configuration.
Figure 7:
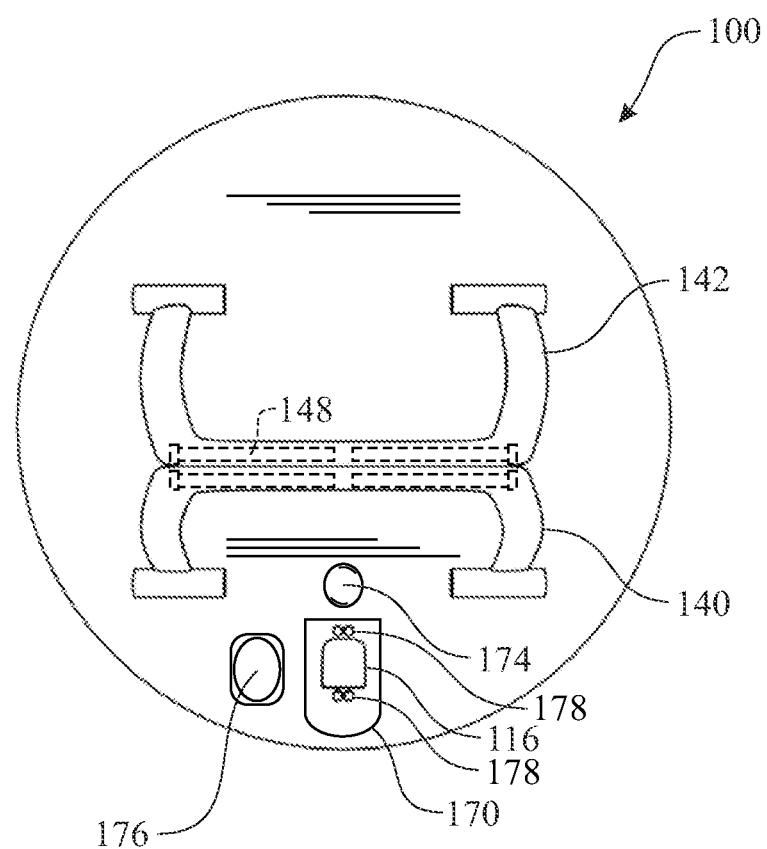
FIG. 7 presents a bottom view of the exemplary narcotics and Opioids secure storage and dispensing apparatus as originally introduced in FIG. 1 with legs closed.

A narcotics and Opioids secure storage and dispensing apparatus 100 is introduced in FIGS. 1 and 2. The shape of the narcotics and Opioids secure storage and dispensing apparatus is generally circular and includes a round primary medication tray 110 and a similarly rounded secondary medication tray 120; each tray 110, 120 having a parallel rounded cover 114 and a secondary cover 124 respectively. The round primary medication tray 110 includes a primary tray medication compartment 112. The rounded secondary medication tray 120 includes a secondary tray medication compartment 122. The two compartments 112, 122 house the medication until the medication is dispensed. Each of the primary medication tray 110 and the secondary medication tray 120 are rotationally controlled to rotate about a tray rotation axle 126. The tray rotation axle 126 can include sleeved elements to independently control rotation of the primary medication tray 110 and the secondary medication tray 120. Alternatively, motors can directly operate each of the primary medication tray 110 and the secondary medication tray 120, where the primary medication tray 110 and the secondary medication tray 120 are designed to rotate about the tray rotation axle 126. The primary medication tray 110 and the secondary medication tray 120 are preferably nested to one another as illustrated in FIG. 5, thus limiting access and removal of the primary medication tray 110 from the narcotics and Opioids secure storage and dispensing apparatus 100.

Figure 15:
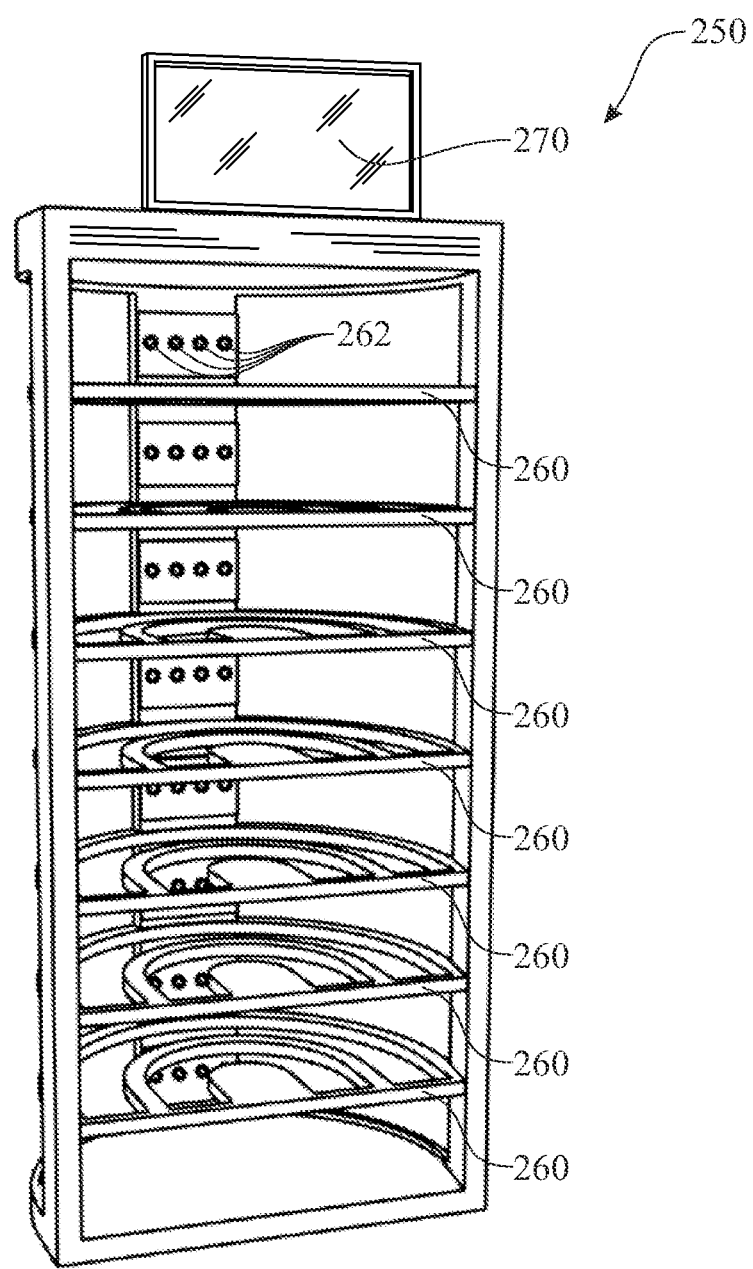
FIG. 15 presents a front, right side isometric view of an exemplary docking station, the docking station being shown in an empty configuration.
Figure 16:
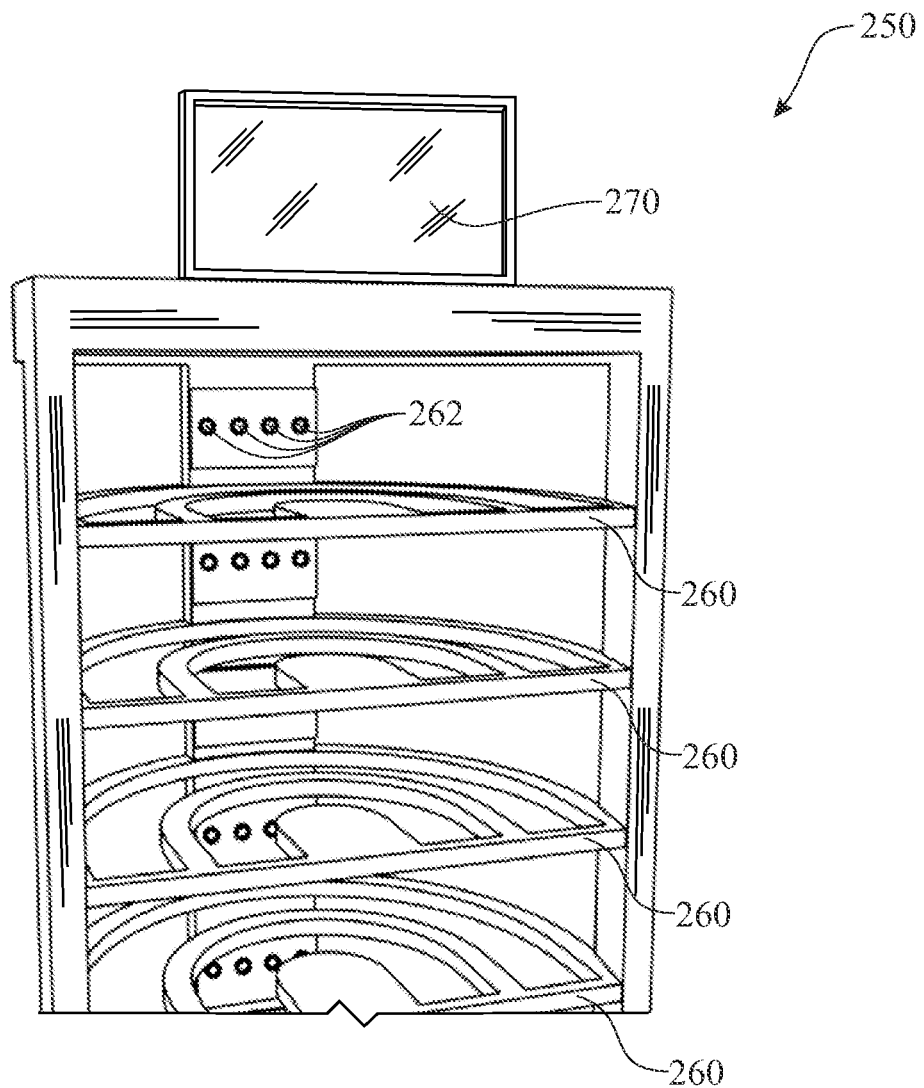
FIG. 16 presents an enlarged front, right side isometric view of the exemplary docking station originally introduced in FIG. 15.
Figure 17:
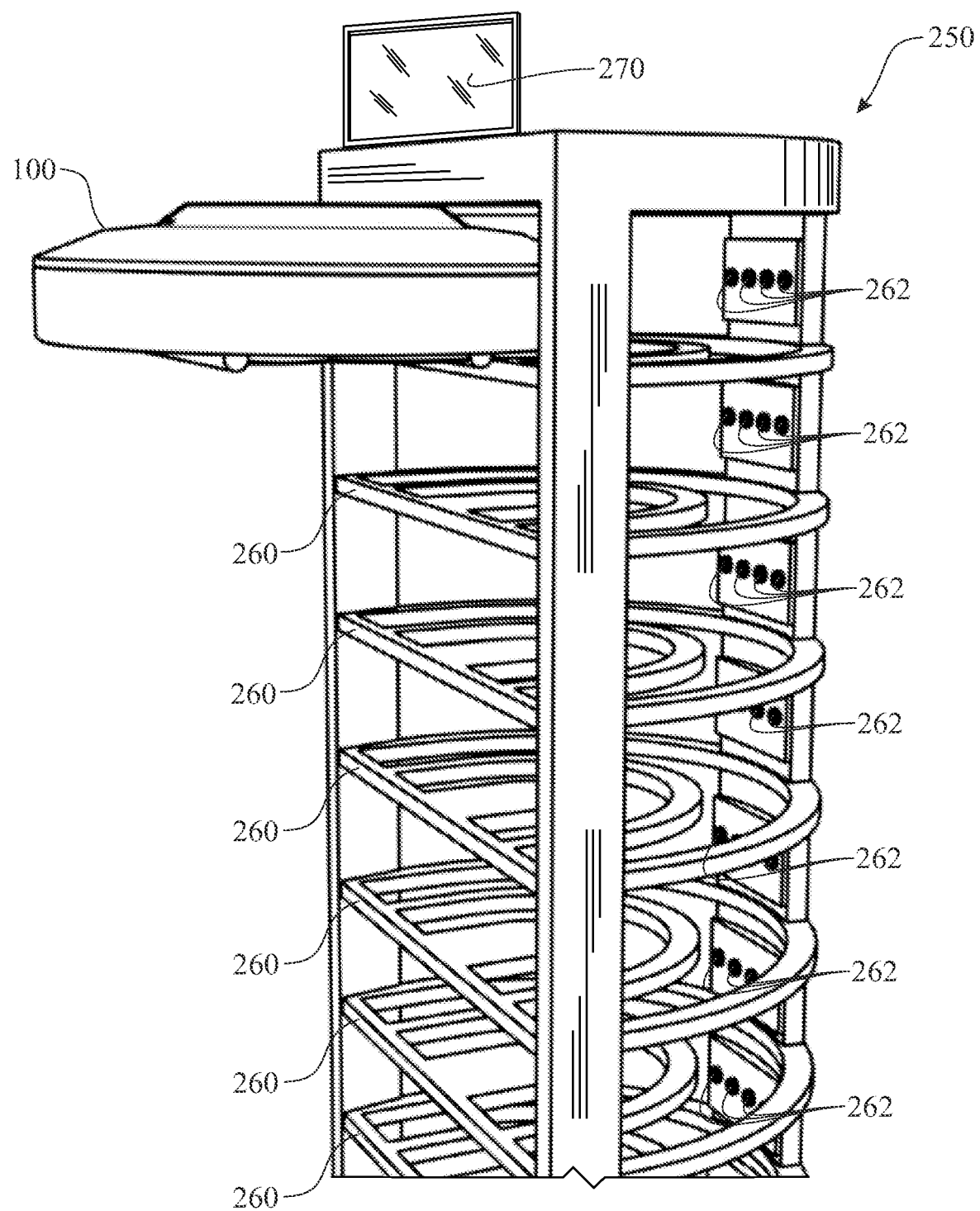
FIG. 17 presents a front, left side isometric view of the exemplary docking station originally introduced in FIG. 15, the illustration presenting one narcotics and Opioids secure storage and dispensing apparatus being partially inserted (docked) into the docking station.
Figure 18:
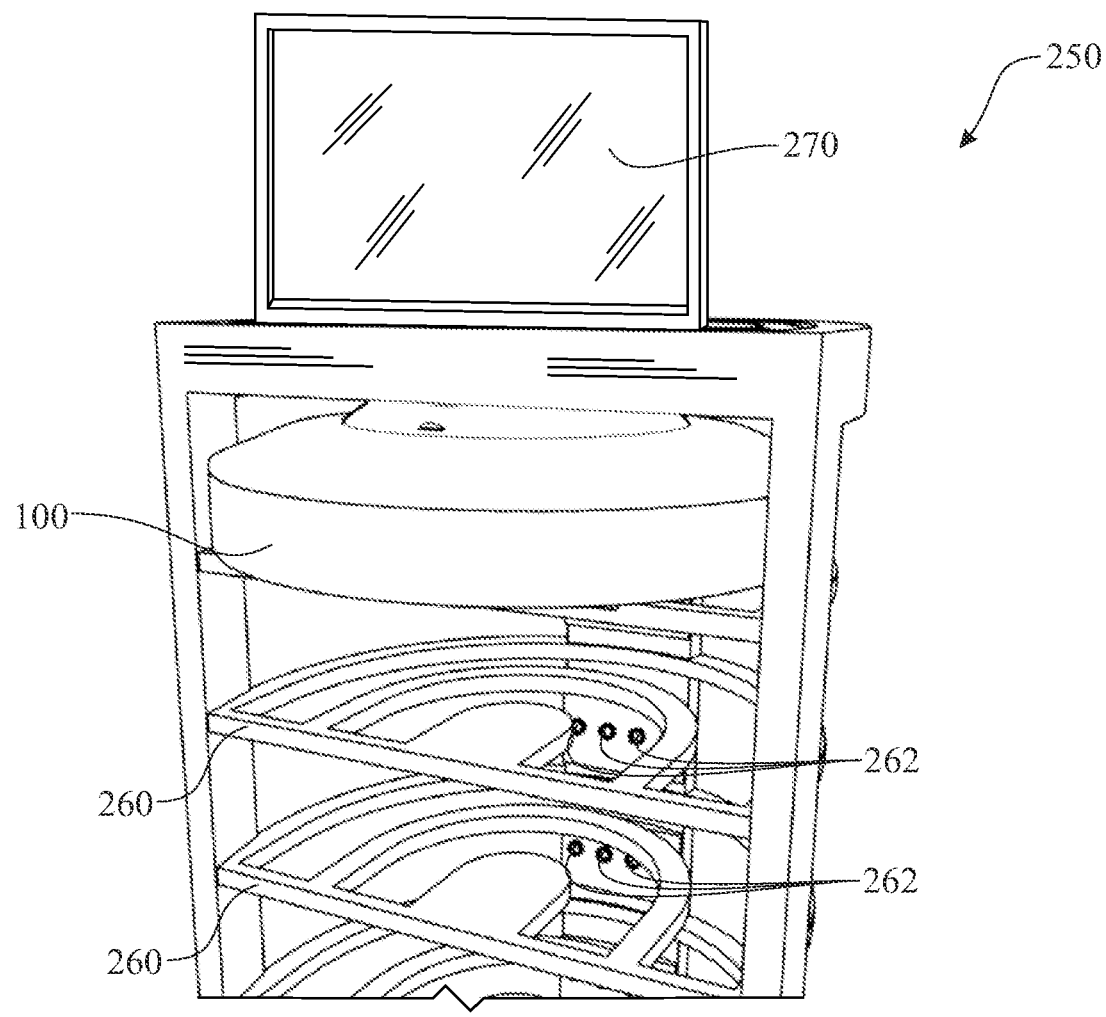
FIG. 18 presents an enlarged front, left side isometric view of the exemplary docking station originally introduced in FIG. 15, the illustration presenting one narcotics and Opioids secure storage and dispensing apparatus being fully inserted (docked) into the docking station.
Figure 19:
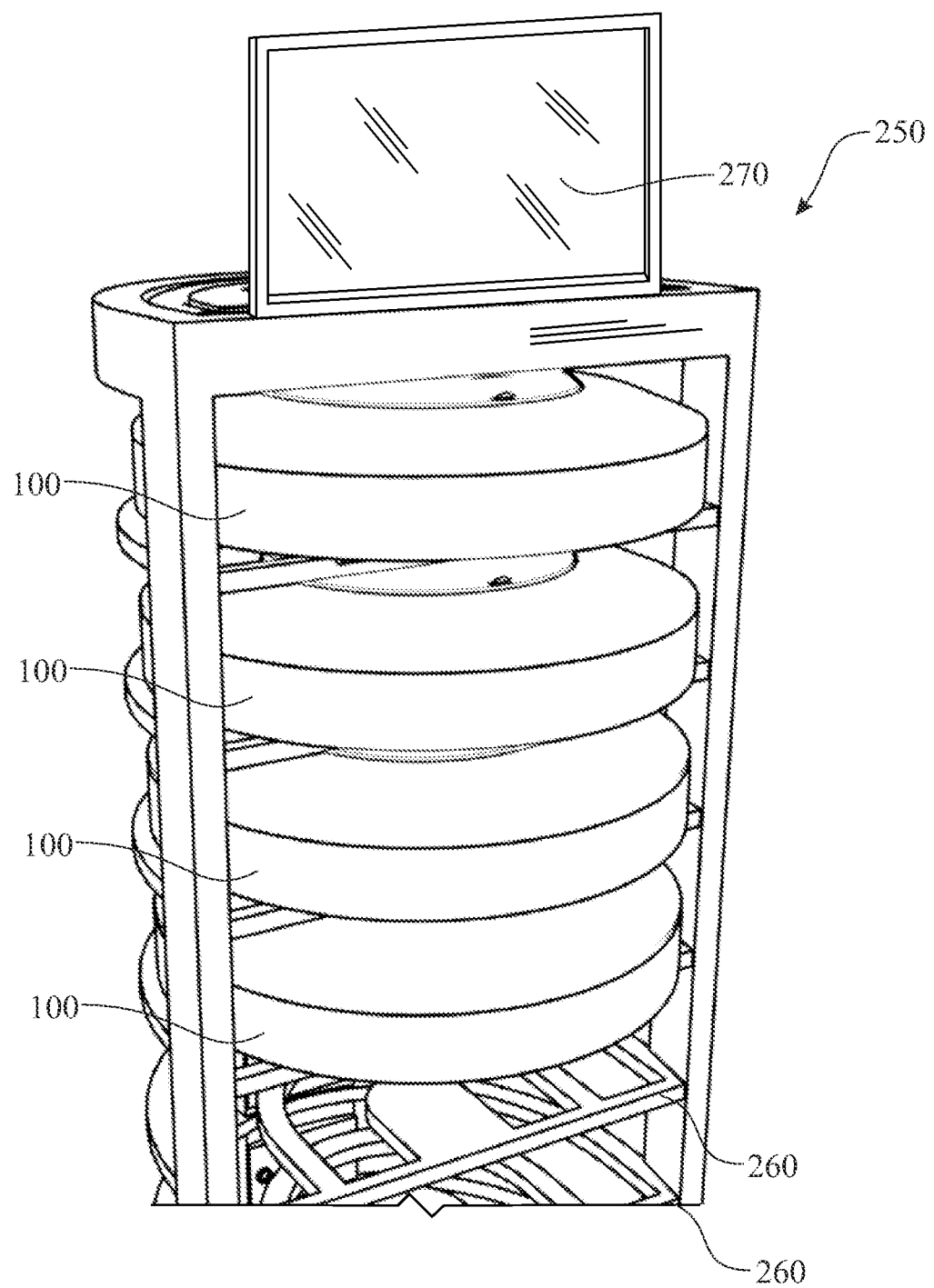
FIG. 19 presents an enlarged front, right side isometric view of the exemplary docking station originally introduced in FIG. 15, the illustration presenting multiple narcotics and Opioids secure storage and dispensing apparatuses being fully inserted (docked) into the docking station.
Figure 20:
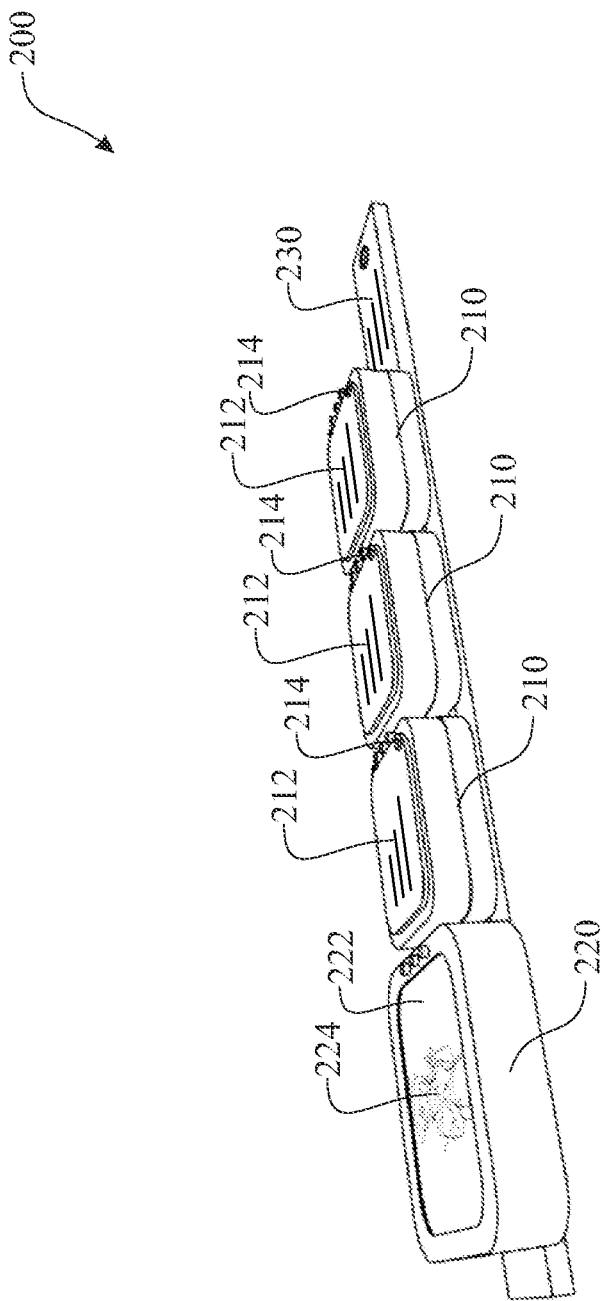
FIG. 20 presents a top, side perspective view of an exemplary wrist/ankle bracelet, the exemplary wrist/ankle bracelet comprising a display unit and three medication compartments.
Figure 21:
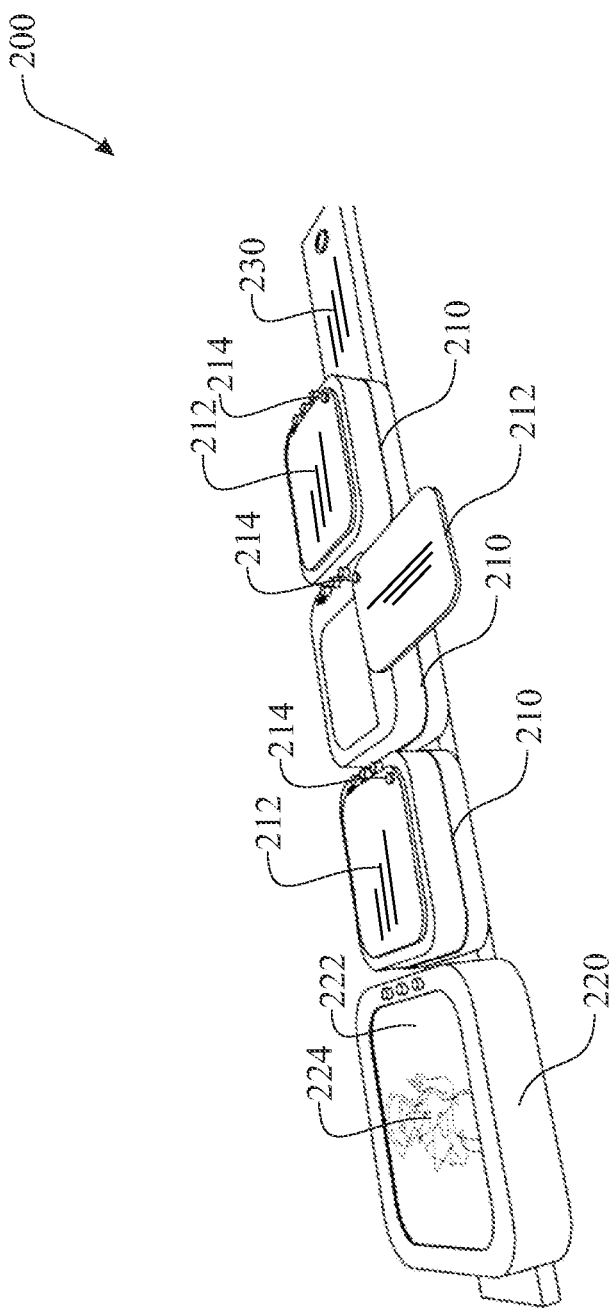
FIG. 21 presents a top, side perspective view of the exemplary wrist/ankle bracelet originally introduced in FIG. 20, the illustration presenting the middle medication compartment being shown in an open position.
Figure 22:
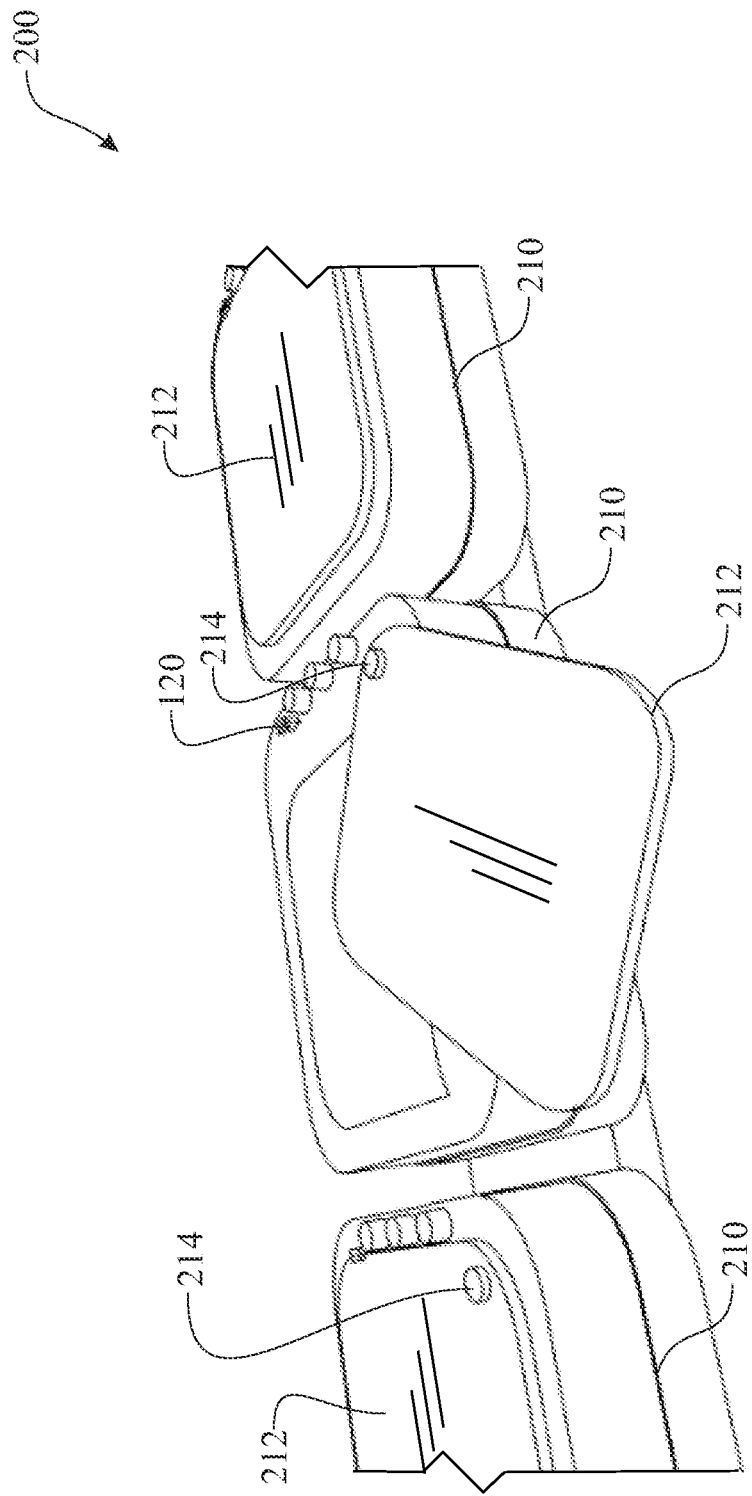
FIG. 22 presents an enlarged top, side perspective view of the exemplary wrist/ankle bracelet originally introduced in FIG. 20, the middle medication compartment in the illustration being shown in a partially open position.
Figure 23:
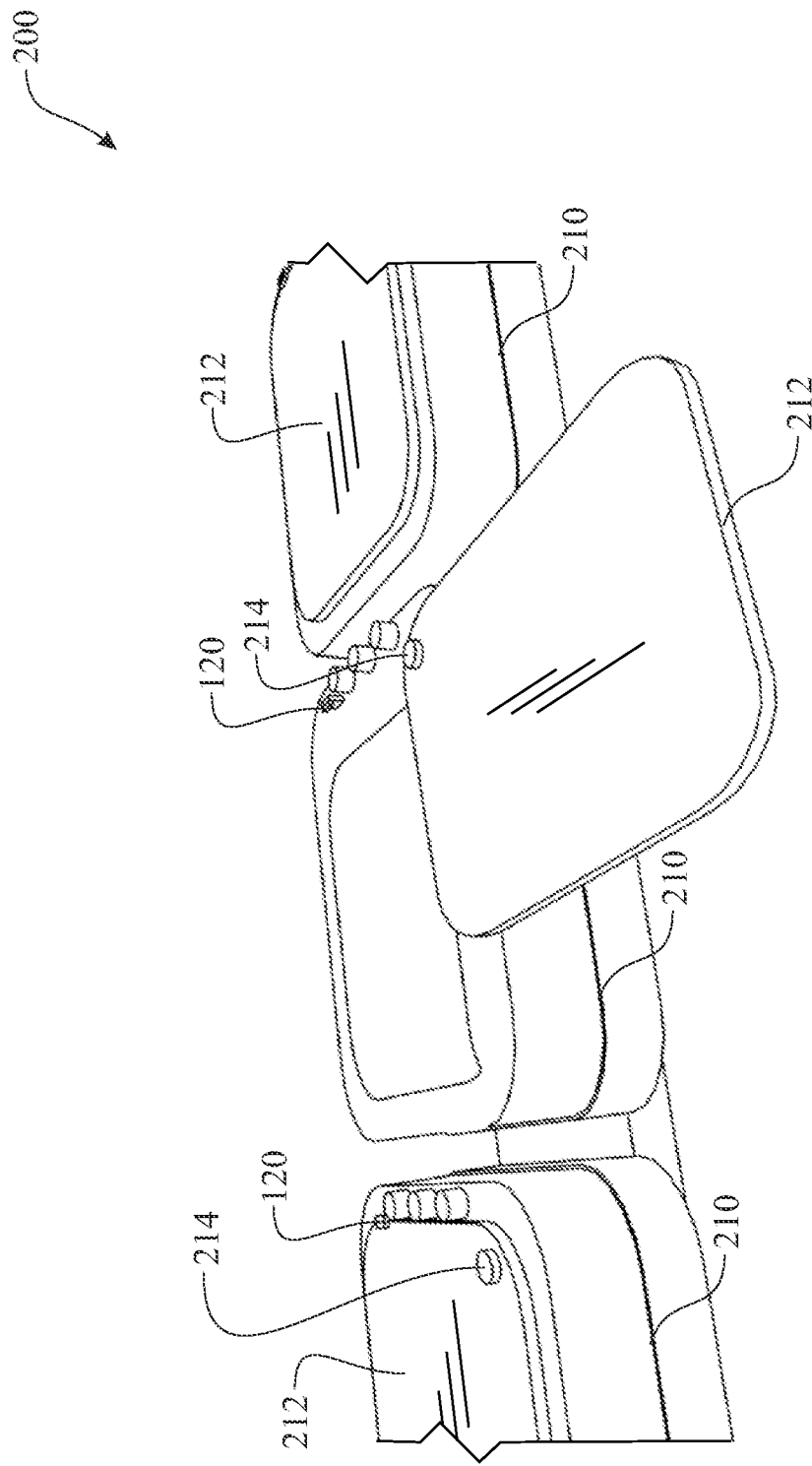
FIG. 23 presents an enlarged top, side perspective view of the exemplary wrist/ankle bracelet originally introduced in FIG. 20, the middle medication compartment of the illustration being shown in a fully open position.
Figure 24:
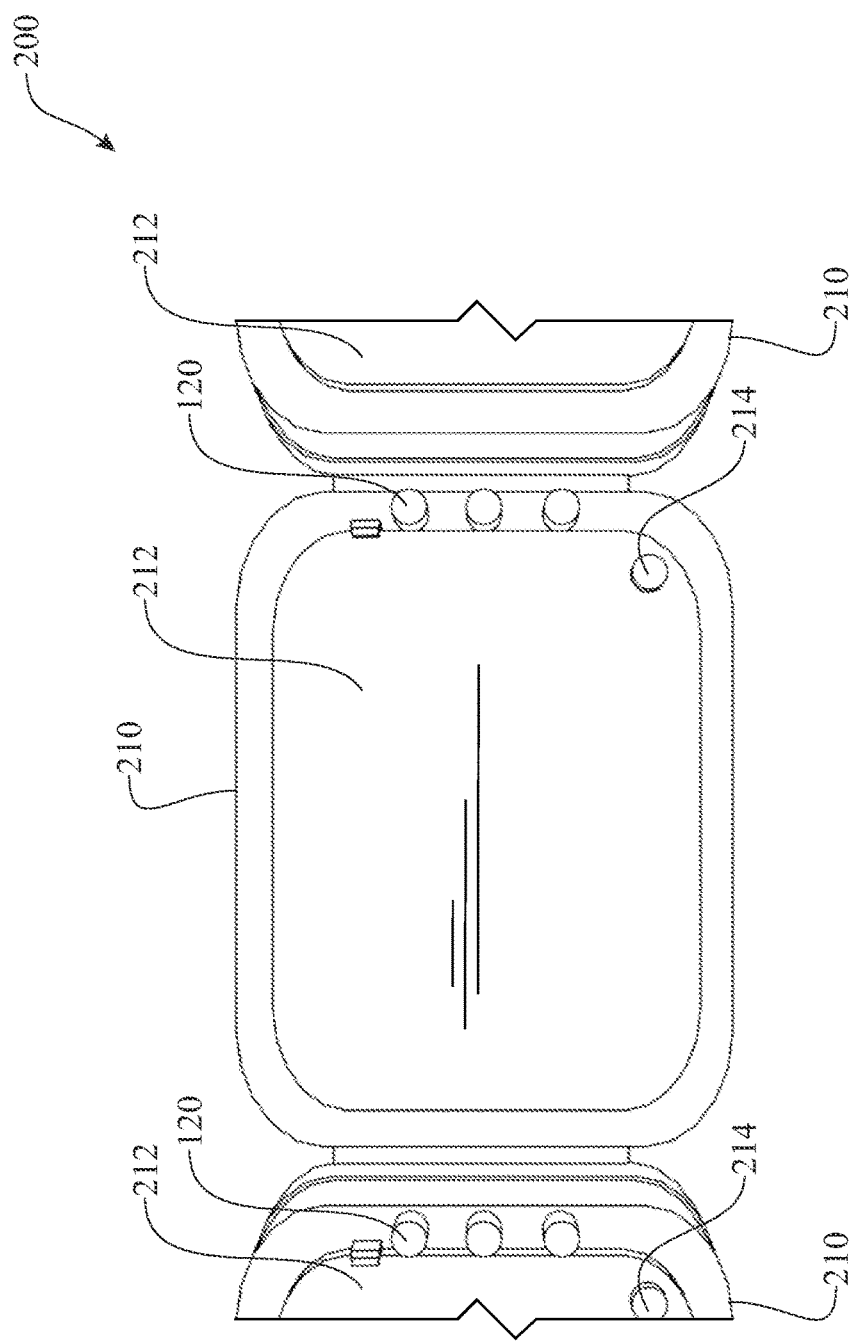
FIG. 24 presents an enlarged top view of the exemplary wrist/ankle bracelet originally introduced in FIG. 20, the three medication compartments of the illustrated bracelet being shown in a closed position.
Figure 25:
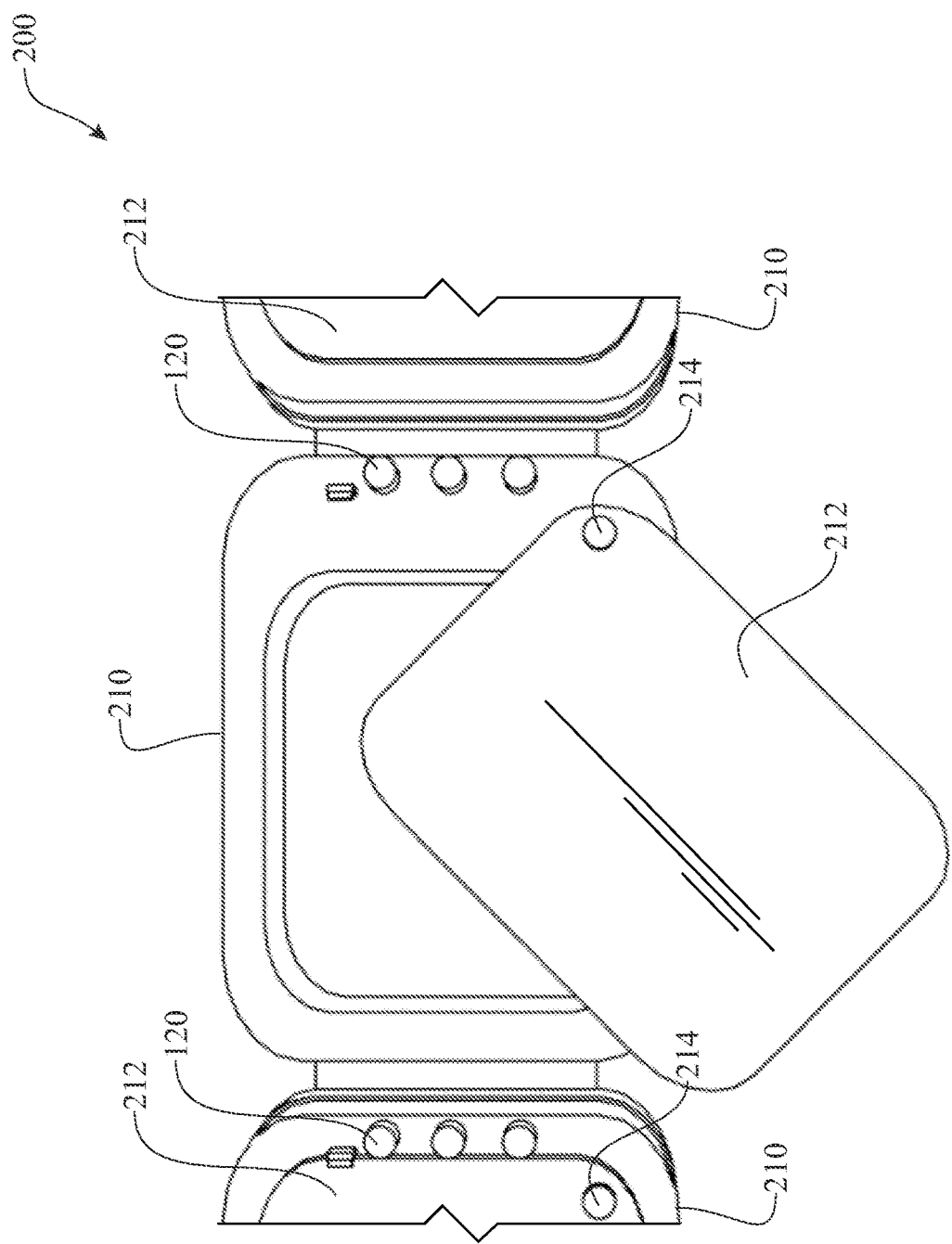
FIG. 25 presents an enlarged top view of the exemplary wrist/ankle bracelet originally introduced in FIG. 20, the middle medication compartment of the illustrated bracelet being shown in a partially open position.
Figure 26:
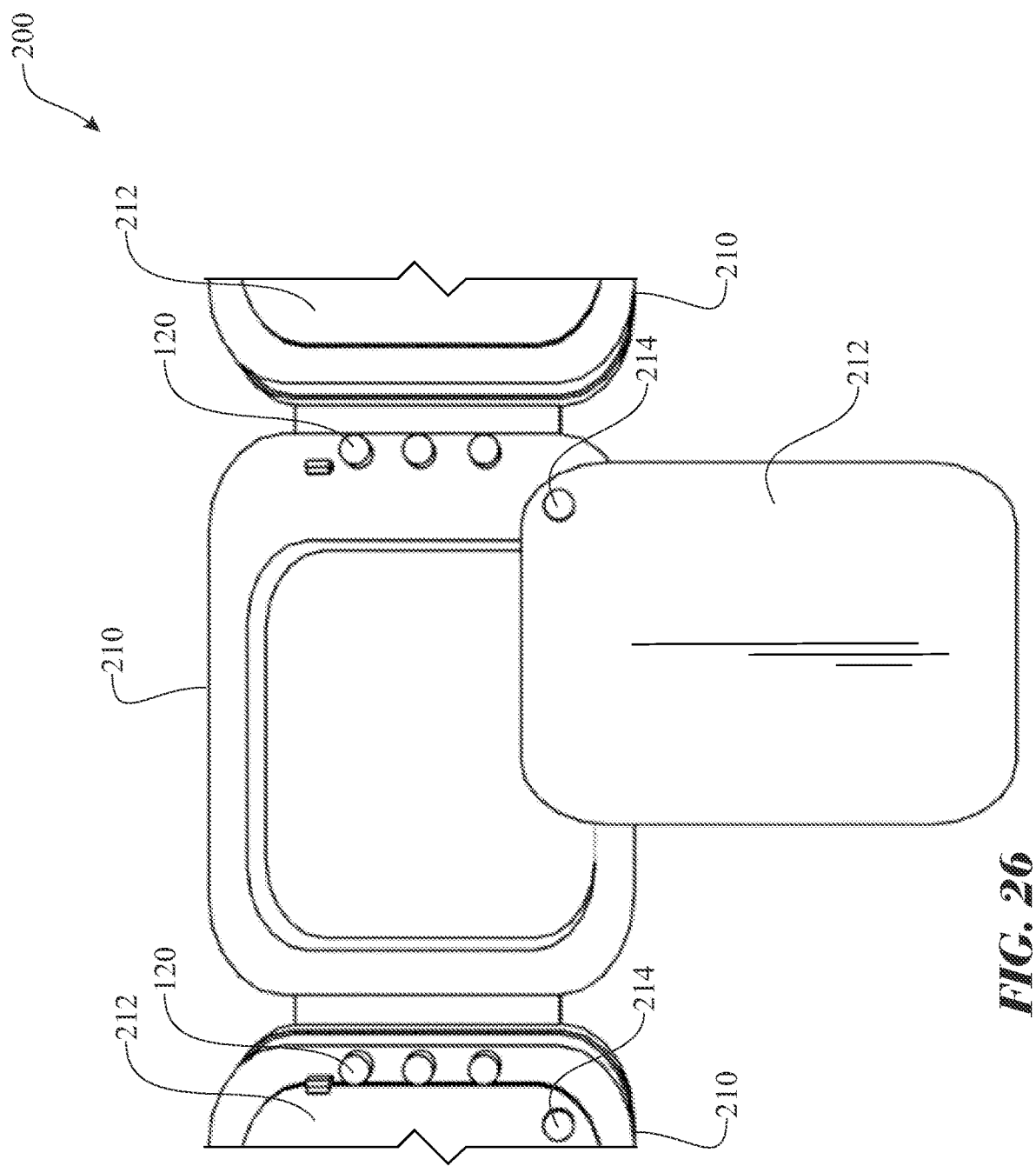
FIG. 26 presents an enlarged top view of the exemplary wrist/ankle bracelet originally introduced in FIG. 20, the middle medication compartment of the illustrated bracelet being shown in an open position.
Figure 27:
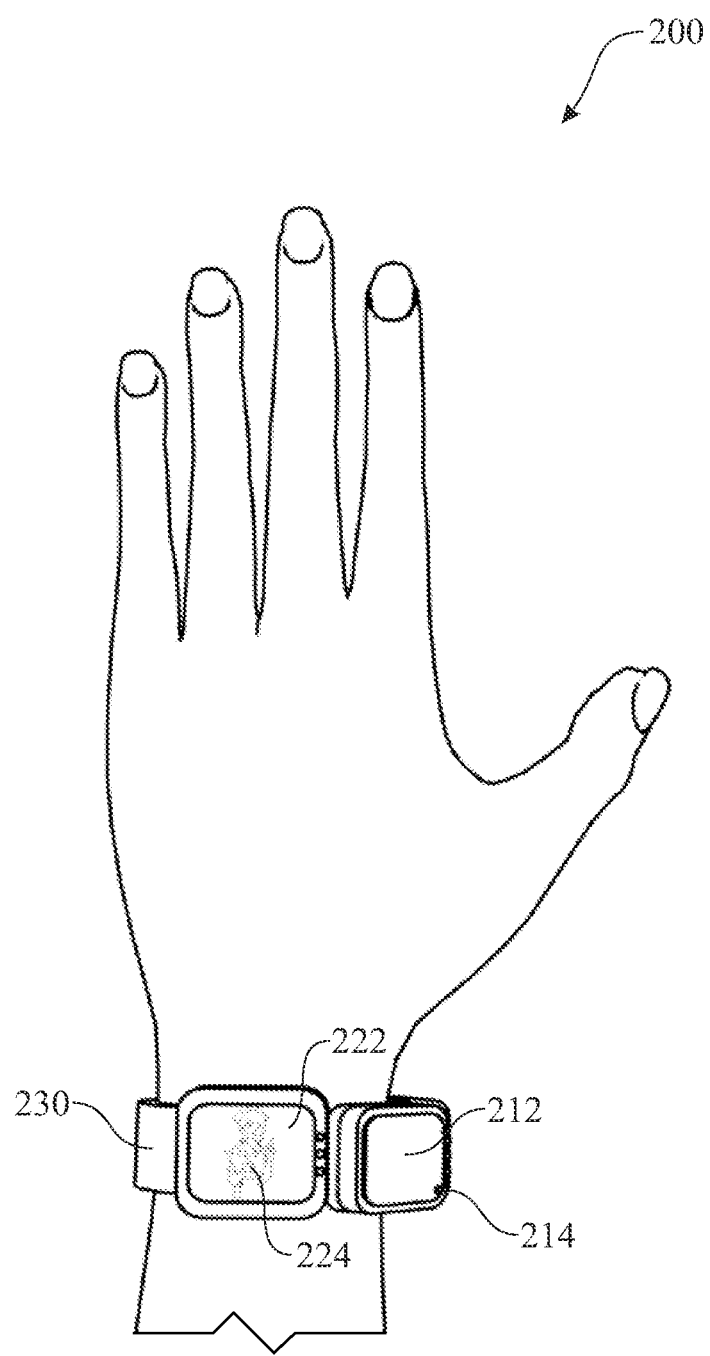
FIG. 27 presents a top view of the exemplary wrist/ankle bracelet originally introduced in FIG. 20, the illustrated exemplary wrist/ankle bracelet shown as being worn as a wrist bracelet.
Figure 28:
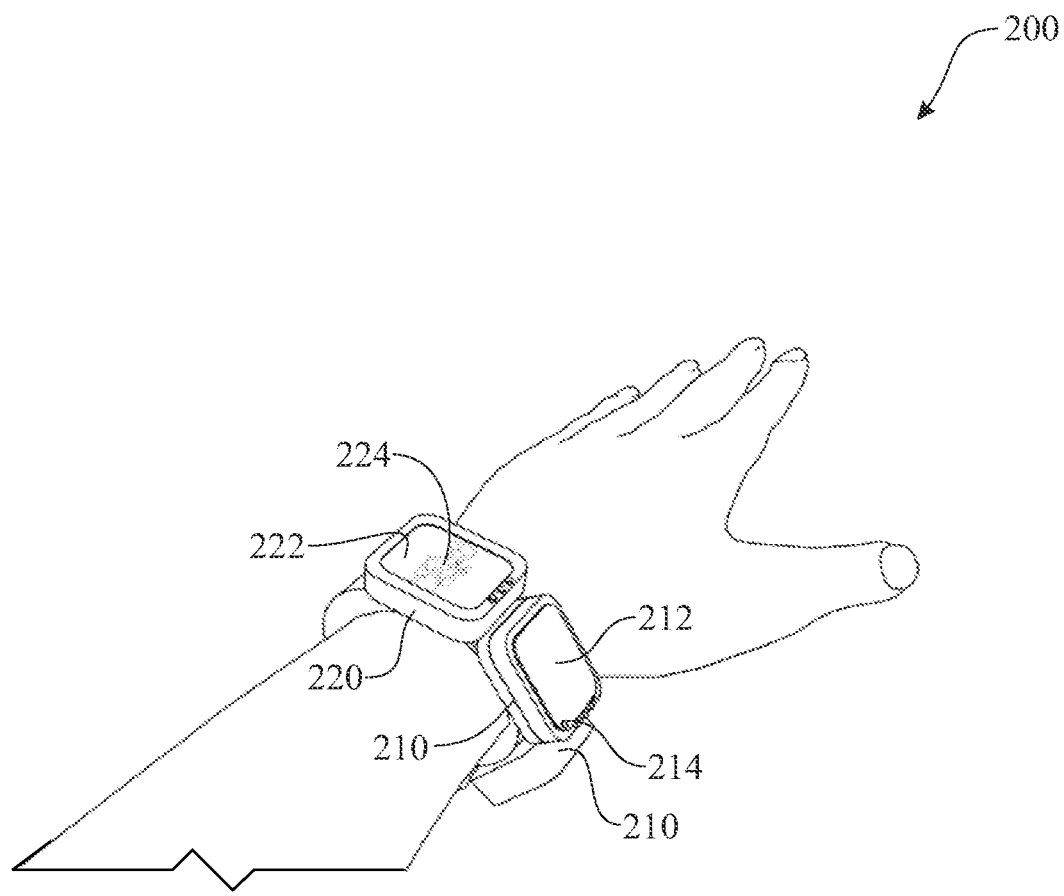
FIG. 28 presents a top, side, rear perspective view of the wrist bracelet as illustrated in FIG. 27.
Figure 29:
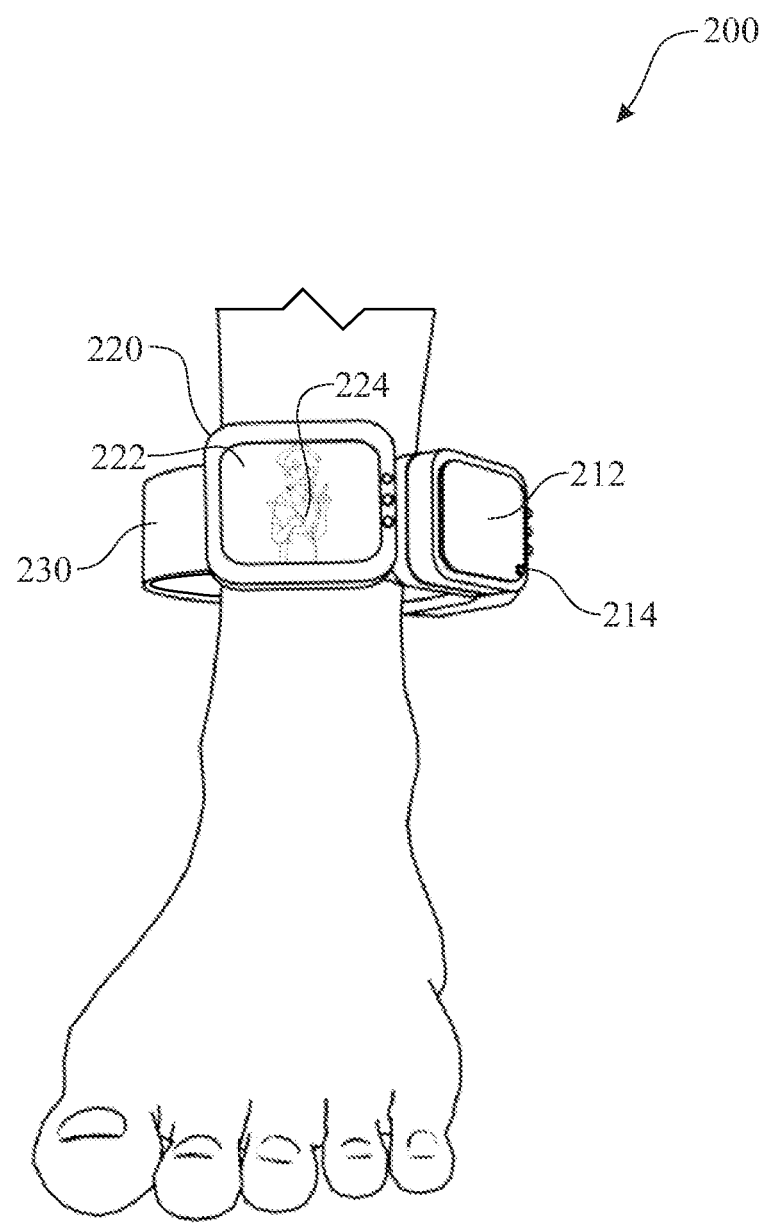
FIG. 29 presents a front view of the exemplary wrist/ankle bracelet originally introduced in FIG. 20, the illustration presenting the exemplary wrist/ankle bracelet shown being worn as an ankle bracelet, the display unit being shown in the front of the ankle.
Figure 30:
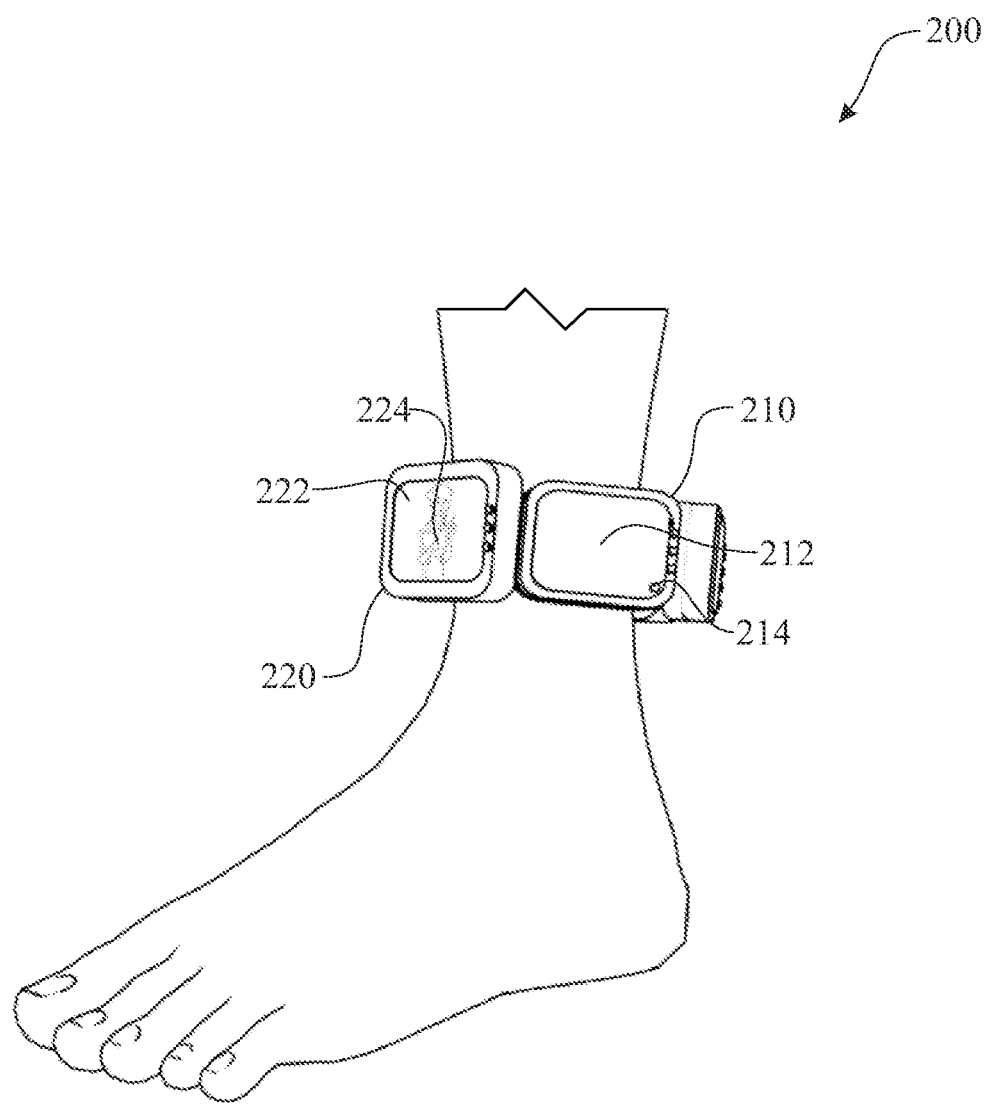
FIG. 30 presents a side view of the exemplary wrist/ankle bracelet originally introduced in FIG. 20, the illustration presenting the exemplary wrist/ankle bracelet shown being worn as an ankle bracelet, the illustration showing the display unit and an adjacent medicine compartment.
Figure 31:
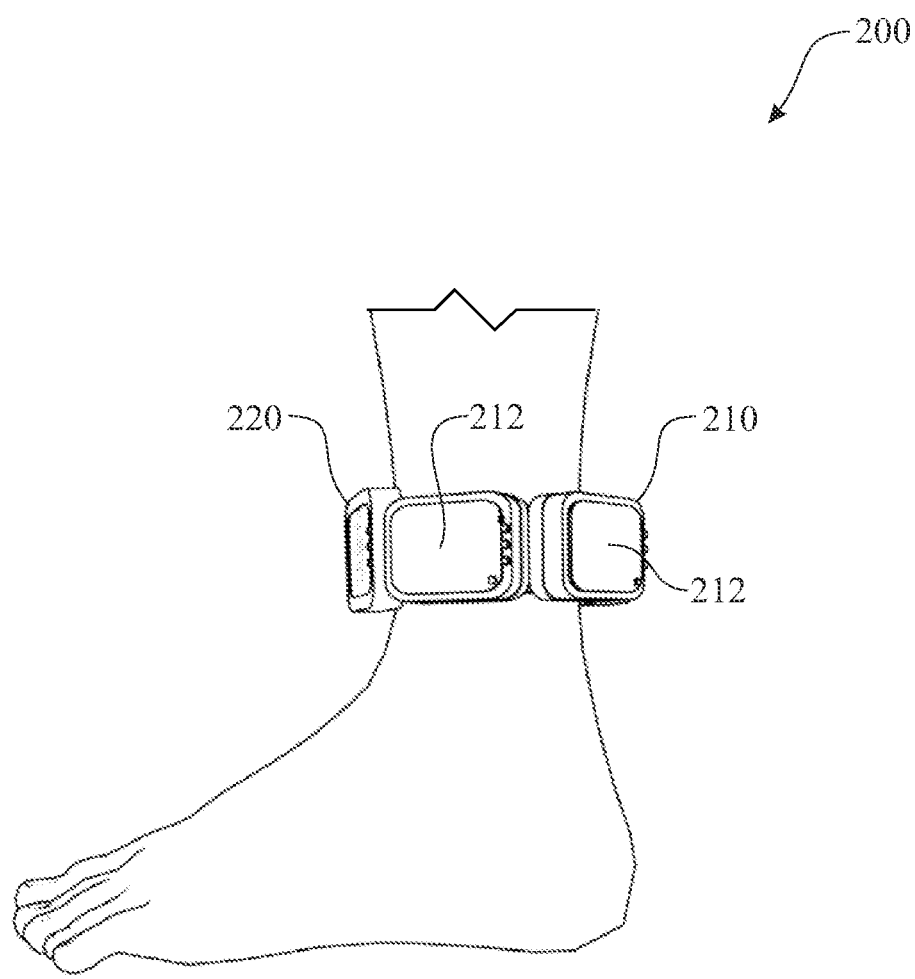
FIG. 31 presents a side view of the exemplary wrist/ankle bracelet originally introduced in FIG. 20, the illustration presenting the exemplary wrist/ankle bracelet shown being worn as an ankle bracelet, the illustration showing the display unit and two medication compartments.
Figure 32:
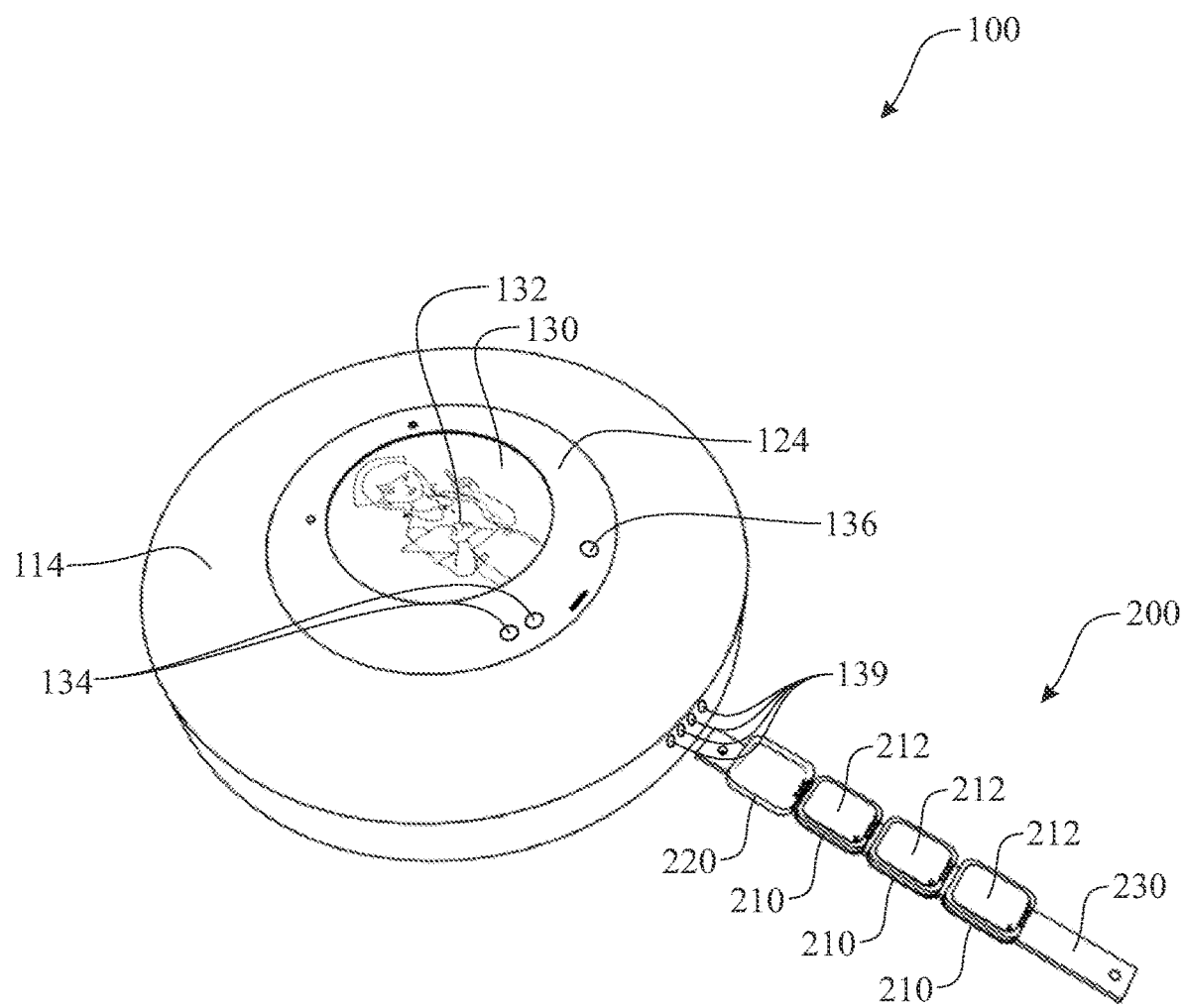
FIG. 32 presents a top, right side isometric view of the narcotics and Opioids secure storage and dispensing apparatus originally introduced in FIG. 1 and the exemplary wrist/ankle bracelet originally introduced in FIG. 20, the illustration showing the exemplary wrist/ankle bracelet in a process of being docked with the narcotics and Opioids secure storage and dispensing apparatus.
Figure 33:
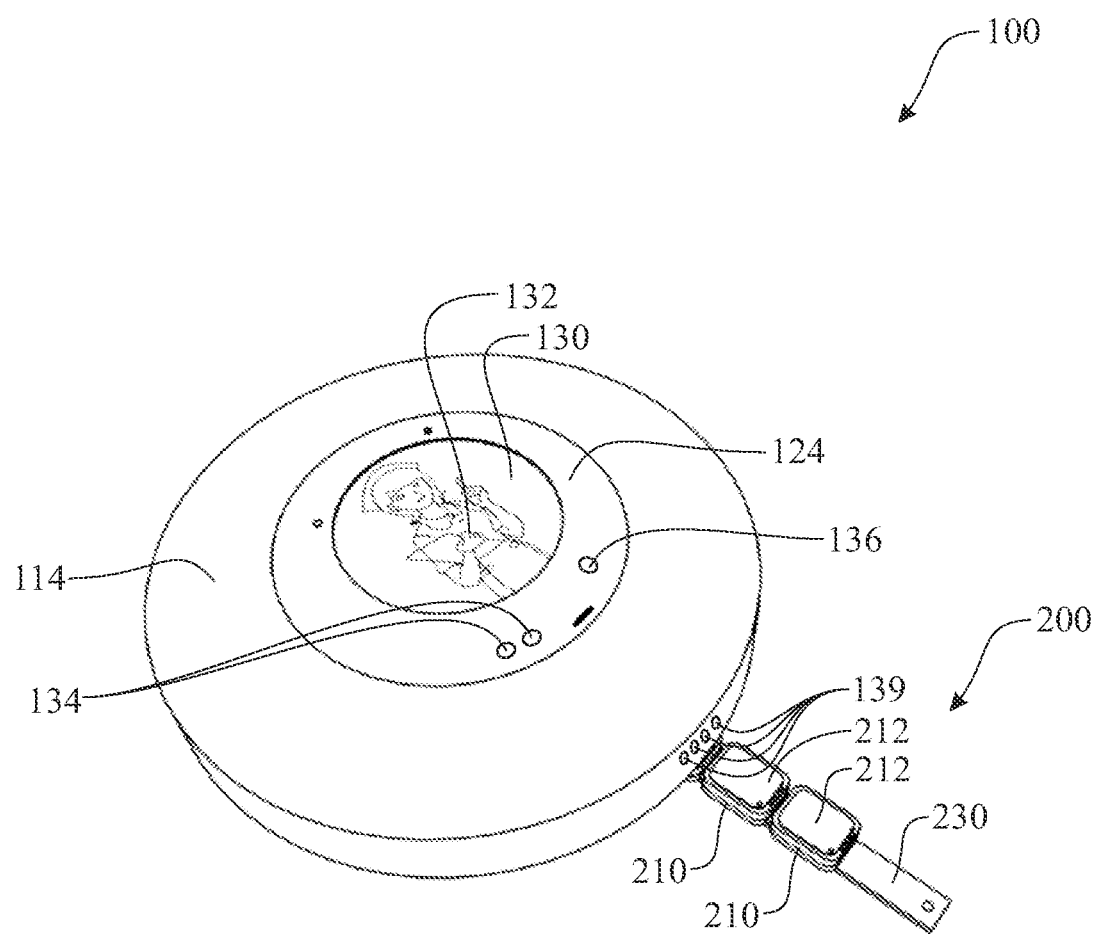
FIG. 33 a top, right side isometric view of the narcotics and Opioids secure storage and dispensing apparatus originally introduced in FIG. 1 and the exemplary wrist/ankle bracelet originally introduced in FIG. 20, the illustration showing the exemplary wrist/ankle bracelet in a docked configuration with the narcotics and Opioids secure storage and dispensing apparatus.
Figure 34:
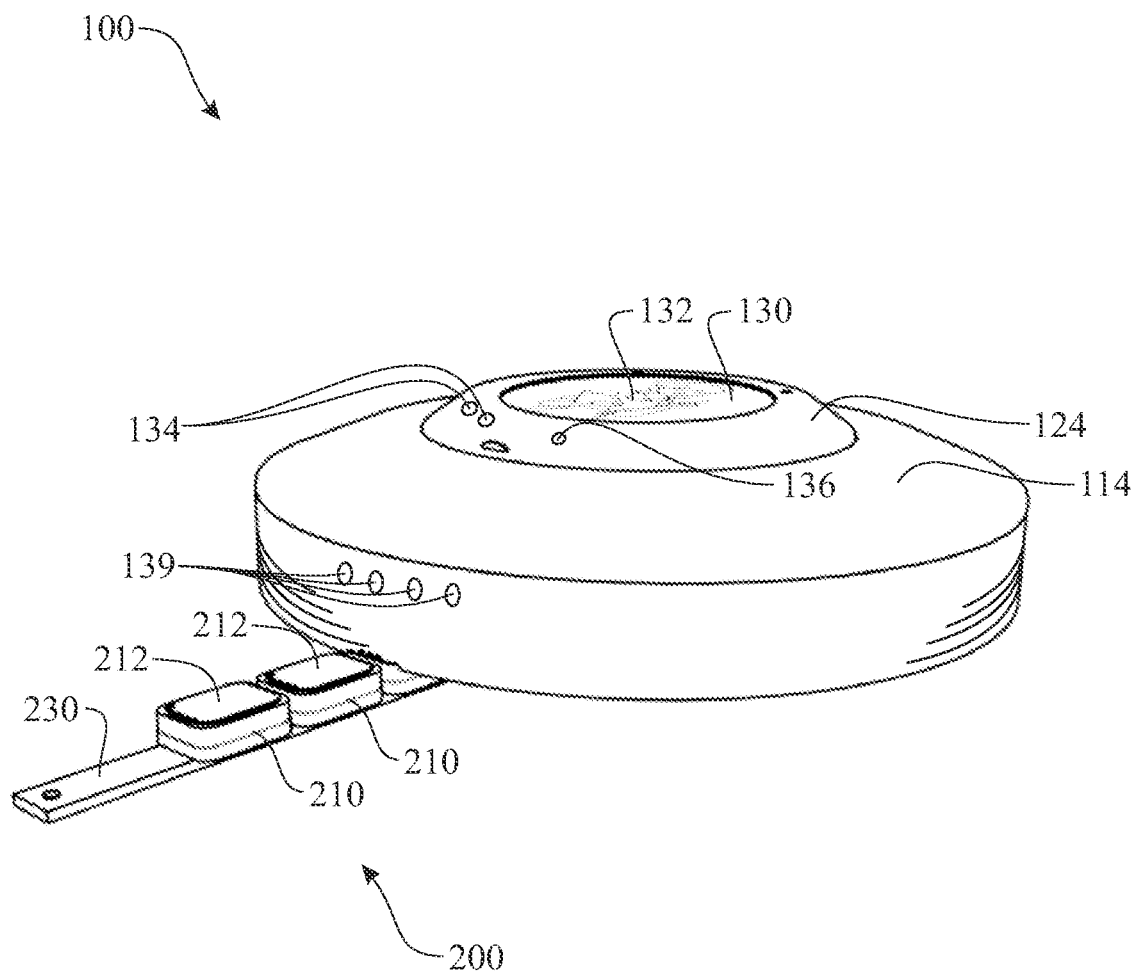
FIG. 34 shows a top, left side isometric view of the narcotics and Opioids secure storage and dispensing apparatus originally introduced in FIG. 1, the illustration presenting the exemplary wrist/ankle bracelet originally introduced in FIG. 20 being docked with the narcotics and Opioids secure storage and dispensing apparatus.
Figure 35:
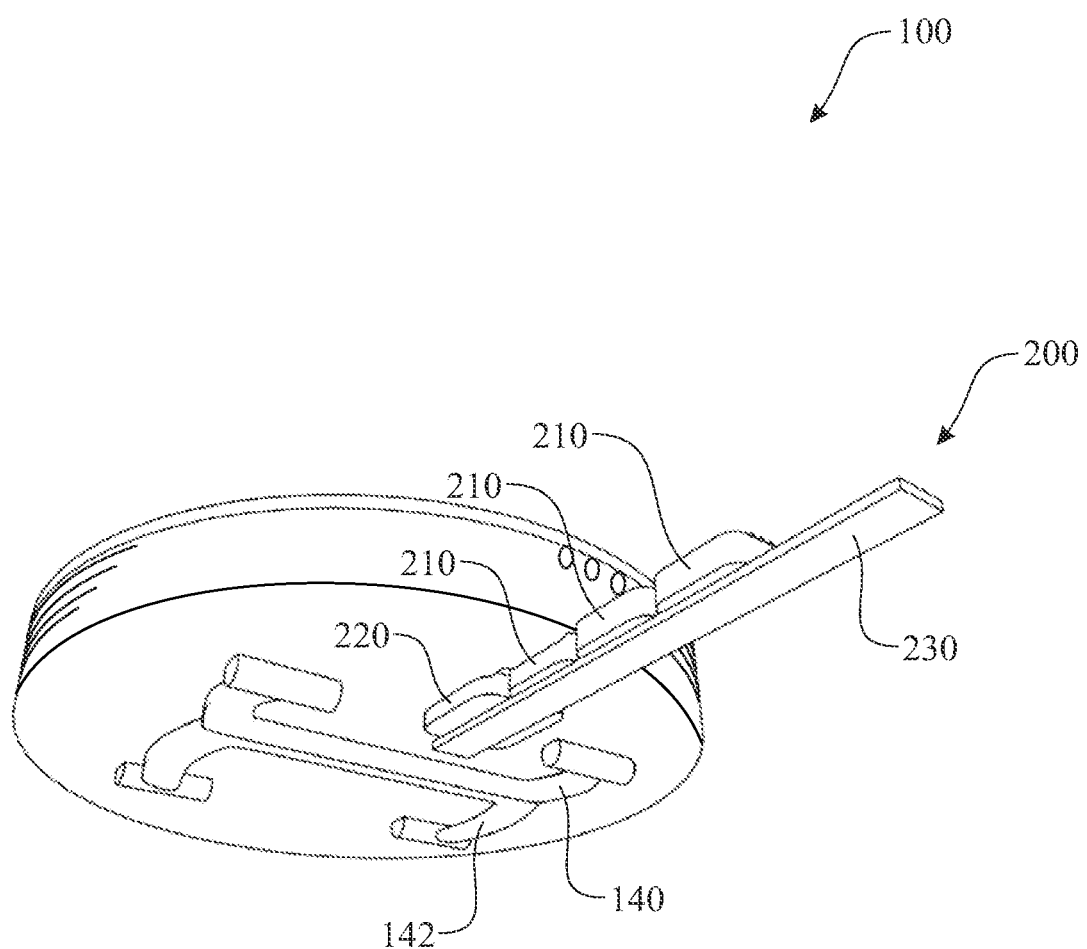
FIG. 35 shows a bottom, right side view of the narcotics and Opioids secure storage and dispensing apparatus originally introduced in FIG. 1, the illustration presenting the exemplary wrist/ankle bracelet originally introduced in FIG. 20 being docked with the narcotics and Opioids secure storage and dispensing apparatus.
Figure 36:
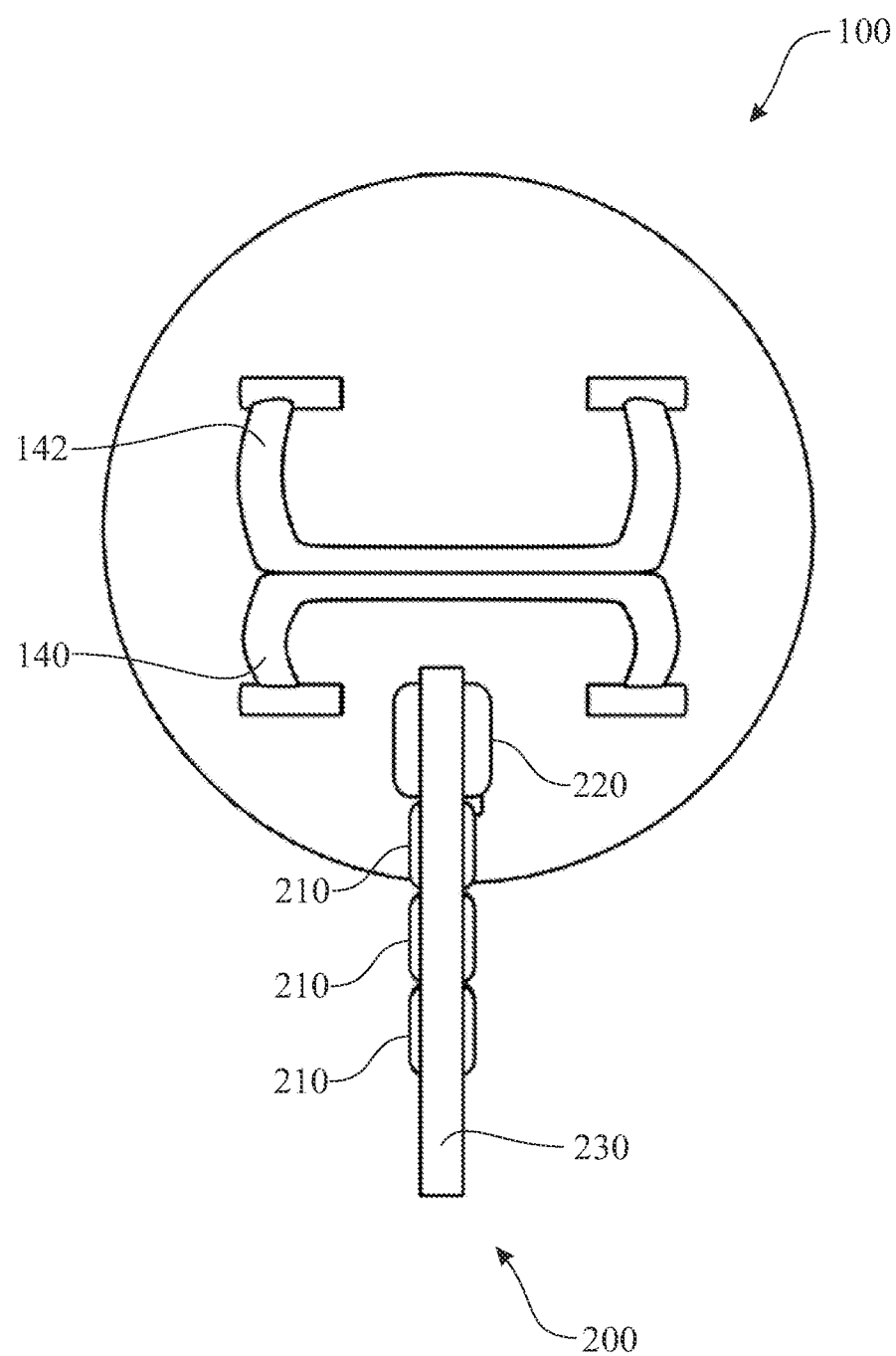
FIG. 36 presents a bottom view of the narcotics and Opioids secure storage and dispensing apparatus originally introduced in FIG. 1, the illustration presenting the exemplary wrist/ankle bracelet originally introduced in FIG. 20 being docked with the narcotics and Opioids secure storage and dispensing apparatus.

The secondary cover 124 may or may not have a port for microphone 136 and speaker 134 which is recessed respective to the top cover 114. The secondary cover 124 also houses a secondary tray cover locking harness 152 and a dual tray cover interconnected locking shaft 154 which is used to lock the device, preventing unauthorized access and tampering. The narcotics and Opioids secure storage and dispensing apparatus 100 includes a display unit 130 used to present a graphical user interface (GUI) for the various functions of the narcotics and Opioids secure storage and dispensing apparatus 100 and can house a mobile computing device and an Avatar 132. The mobile computing device can be embedded into the current setup and maybe a separate detachable unit. The narcotics and Opioids secure storage and dispensing apparatus 100 can include a set of legs 140, 142, one in the back (rear supporting leg 142) and the other in the front (front supporting leg 140). The narcotics and Opioids secure storage and dispensing apparatus 100 can be charged through charging contacts 139. The charging contacts 139 can also provide a connection to the charging contacts 262 within each storage shelf 260 of a storage cart (docking station) 250 (FIG. 15).

Referring to FIGS. 3 through 8, when in use, the narcotics and Opioids secure storage and dispensing apparatus 100, the top cover 114 securely covers the manually loaded medication as well as a sealed blister pack 160 medication can be placed in the primary medication tray 110. Meanwhile, the secondary mediation tray cover 124 securely covers the secondary medication tray 120 of the narcotics and Opioids secure storage and dispensing apparatus 100 which contains manually loaded supplemental medications, vitamins and other pills 129. The top cover 120 further utilizes a tamper proof dual lock mechanism to securely lock access to medication 119, 129 in both the primary medication tray 110 as well as the secondary medication tray 120 wherein a motorized shaft securely anchors the access cover 124 of the inner rotary tray 120 and furthermore, a plurality of sliding shafts 150 extend out of the inner rotary tray access cover 124 and protrude into matching holes (not shown) within outer rotary tray access cover 114 to interlock and secure the two rotary access covers 114, 124. The secondary mediation tray cover 124 for secondary mediation tray 120 also comprises of an embedded touch display screen 130, a microphone 136 and a speaker 134 which allow the artificial intelligence avatar 132 (FIG. 8) as well as the remote operators and caregivers to interactively communicate with the user.

The primary medication tray 110 of the narcotics and Opioids secure storage and dispensing apparatus 100, can hold both manually loaded pills 119, 129 as well as a sealed blister pack 160 (described in FIGS. 9 through 14). The primary medication tray 110 comprises multiple medication compartments 112 containing Opioids and other medications 119 for one or more time instances during a day such as morning, noon, afternoon and evening, as well as one or more days of the week. The primary medication tray 110 utilizes a motor 352 to rotate and present the medication stored in each medication compartment at the appropriate time and day of the week. Medication contained within the sealed blister pack 160 placed in the primary medication tray 110 can be dispensed utilizing a punch lever 118 and the supporting motor and electronic 356. A medication dispensing schedule for the primary medication tray 110, (such as a schedule based upon primary medication 119 of the Blister pack 160) and the secondary medication 129 dispensed into the secondary supplemental medication tray 120 of the narcotics and Opioids secure storage and dispensing apparatus 100 can be programmed locally by utilizing the artificial intelligence Avatar assistant 132 as well as by remote caregivers and physicians utilizing the wireless module 340. The artificial intelligence virtual assistant Avatar 132 further utilizes text to speech, speech to text and Natural Language Processing NLP 326 technology to interactively communicate with the user, triage the user and gather relevant information regarding user's health status.

The secondary medication tray 120 of narcotics and Opioids secure storage and dispensing apparatus 100 contains manually loaded supplemental medications, vitamins, and other pills 129. The secondary medication tray 120 comprises of multiple medication compartments 122 containing vitamins, supplemental medication and new additions to regular medication contained in the primary medication try 110.

Dispensing of the medications contained in each of the secondary medication tray 120 compartment 122 can be programmed to dispense at:

a. Simultaneously, with the medication in the primary medication tray compartments at the scheduled time instance such as morning, noon, afternoon and evening, as well as the scheduled day of the week.
b. At a pre-programmed time interval prior to the dispensing of the medication in the primary medication tray compartments at the scheduled time instance such as morning, noon, afternoon and evening, as well as the scheduled day of the week.
c. At a pre-programmed time interval after the dispensing of the medication in the primary medication tray compartments at the scheduled time instance such as morning, noon, afternoon and evening, as well as the scheduled day of the week The secondary tray cover 124 for secondary mediation tray 120 further comprises an embedded touch display screen 130 or a mobile device 368, such as a mobile phone or a tablet, as well as a microphone 136 and speaker 134, wherein the microphone 136 and the speaker 134 allow the artificial intelligence Avatar assistant 132 as well as the remote operators and caregivers to interactively communicate with the user.

The display unit 130 of the narcotics and Opioids secure storage and dispensing apparatus 100 is utilized to schedule, edit and view medication to be dispensed, provide visual communication between the artificial intelligence Avatar assistant 132 and the user and provide video communication between the user and remotely located operators and caregivers.

The artificial intelligence Avatar assistant 132 of the narcotics and Opioids secure storage and dispensing apparatus 100 utilizes text to speech, speech to text and Natural Language Processing (NLP) 326 technology to interactively communicate with the user, triage the user and gather relevant information regarding user's health status.

The legs 140, 142 can provide several functions. The front supporting leg 140 of the narcotics and Opioids secure storage and dispensing apparatus 100 that can be folded closed and snapped in place to allow the device to be carried around.

The rear supporting leg 142 of the narcotics and Opioids secure storage and dispensing apparatus 100 that can be folded closed and snapped in place to allow the device to be carried around. The rear leg 142 can also folded fully open and snapped in place, to be used as a carrying handle for the device.

One or both legs 140, 142 can include a controlled access to a storage cavity provided within an interior of the respective leg 140, 142. Access to the storage cavity can be provided by a supporting leg storage access element 141, 143. The supporting leg storage access element 141, 143 is preferably a door which can be pivotally opened, hingeably opened, slideably opened, or opened using any other suitable process. The supporting leg storage access element 141, 143 can be locked with limited access, where the access could be provided via a remote authorization from a counselor, a medical support person, an Emergency Medical Technician (EMT), a nurse, a nurse practitioner, a physician, or any other authorized party. One or more treatments of a suspected overdose counteracting drug 148 can be storage within the storage cavity. In one example, the suspected overdose counteracting drug 148 can be NARCAN® provided in either a spray or an injecting delivery format. It is preferred to include at least two treatments of the suspected overdose counteracting drug 148 within the narcotics and Opioids secure storage and dispensing apparatus 100.

Although the illustrated exemplary narcotics and Opioids secure storage and dispensing apparatus 100 utilizes the legs 140, 142 for storage of the suspected overdose counteracting drug 148, the suspected overdose counteracting drug 148 can be stored in a storage cavity located anywhere on the exemplary narcotics and Opioids secure storage and dispensing apparatus 100, including the body, an underside of the body, or any other suitable location.

Access to the storage cavity can be initiated by actuation of a panic button 138. The user can actuate the panic button 138 using any prescribed process. For example, the panic button 138 can be actuated by depressing the panic button 138 over an extended period of time (such as 3 seconds). In another example, actuation can be accomplished by simultaneously depressing a pair of spatially arranged panic buttons 138.

Upon actuation of the panic button(s) 138, the narcotics and Opioids secure storage and dispensing apparatus 100 can proceed along any of several paths. a first option would be to provide immediate access to the suspected overdose counteracting drug 148 stored within the narcotics and Opioids secure storage and dispensing apparatus 100. A second option would be to initiate access for authorization. The narcotics and Opioids secure storage and dispensing apparatus 100 would access a predetermined authorizing party, such as a counselor, a medical support person, an Emergency Medical Technician (EMT), a nurse, a nurse practitioner, a physician, or any other authorizing party. The authorizing party would determine whether conditions are appropriate to provide access to the suspected overdose counteracting drug 148 stored within the narcotics and Opioids secure storage and dispensing apparatus 100. The authorizing party can opt to contact the user via the wireless module 340 of the narcotics and Opioids secure storage and dispensing apparatus 100 and interact with the user via the user interface 360. Alternatively, the authorizing party activate features of the narcotics and Opioids secure storage and dispensing apparatus 100 to determine the conditions surrounding the narcotics and Opioids secure storage and dispensing apparatus 100. Examples of remotely activated features can include microphone 136, a medication consumption tracking (fisheye) camera 172, a medication dispense monitoring camera 174, or any other feature installed on the narcotics and Opioids secure storage and dispensing apparatus 100 which can acquire information that can aid the authorizing party in determining the conditions of the user and surrounding environment. The medication consumption tracking (fisheye) camera 172 and the microphone 136 can be remotely activated, if desired, to record both video and audio following the unwarranted motion. The artificial intelligence avatar 132 (or any other suitable communication elements) can be activated by a remote party to communicate with one or more persons (such as the user) that would be located proximate the narcotics and Opioids secure storage and dispensing apparatus 100 as desired.

Access to the suspected overdose counteracting drug 148 can be provided by any suitable controlled access panel 141, 143. This can include a motorized access control, a magnetically controlled access operation, a mechanically controlled access operation, a pin controlled access operation, or any other locking and opening access control. Access can also be monitoring by a security monitoring system similar to or the same security monitoring system employed for monitoring security of the narcotics and Opioids secure storage and dispensing apparatus 100. It is recognized that access to the suspected overdose counteracting drug 148 is less concerning than access to the narcotics or Opioids stored within the primary medication tray 110. Although the exemplary illustrations present the storage for the suspected overdose counteracting drug 148 within the legs 140, 142 of the narcotics and Opioids secure storage and dispensing apparatus 100, the suspected overdose counteracting drug 148 can be stored in any reasonable portion of the narcotics and Opioids secure storage and dispensing apparatus 100.

Figure 9:
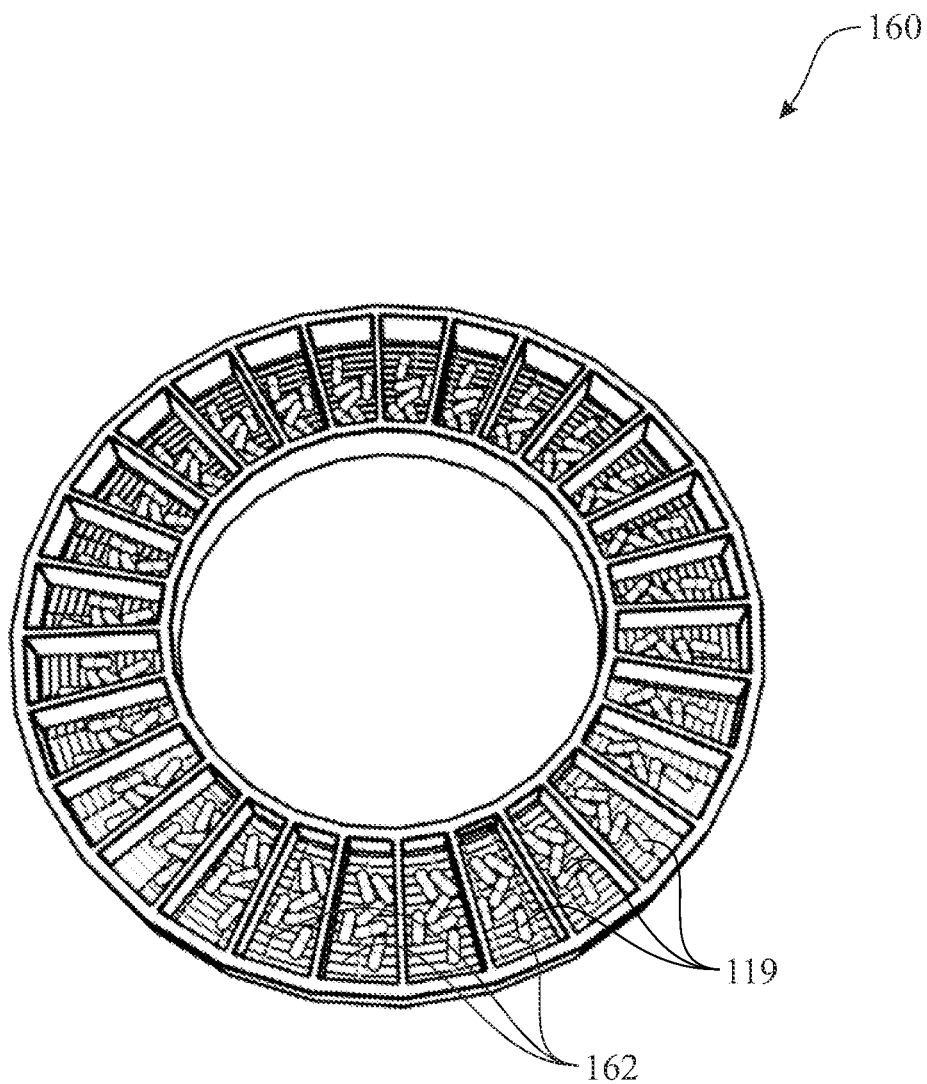
FIG. 9 presents a top isometric view of an exemplary sealed blister pack filled with pills.
Figure 10:
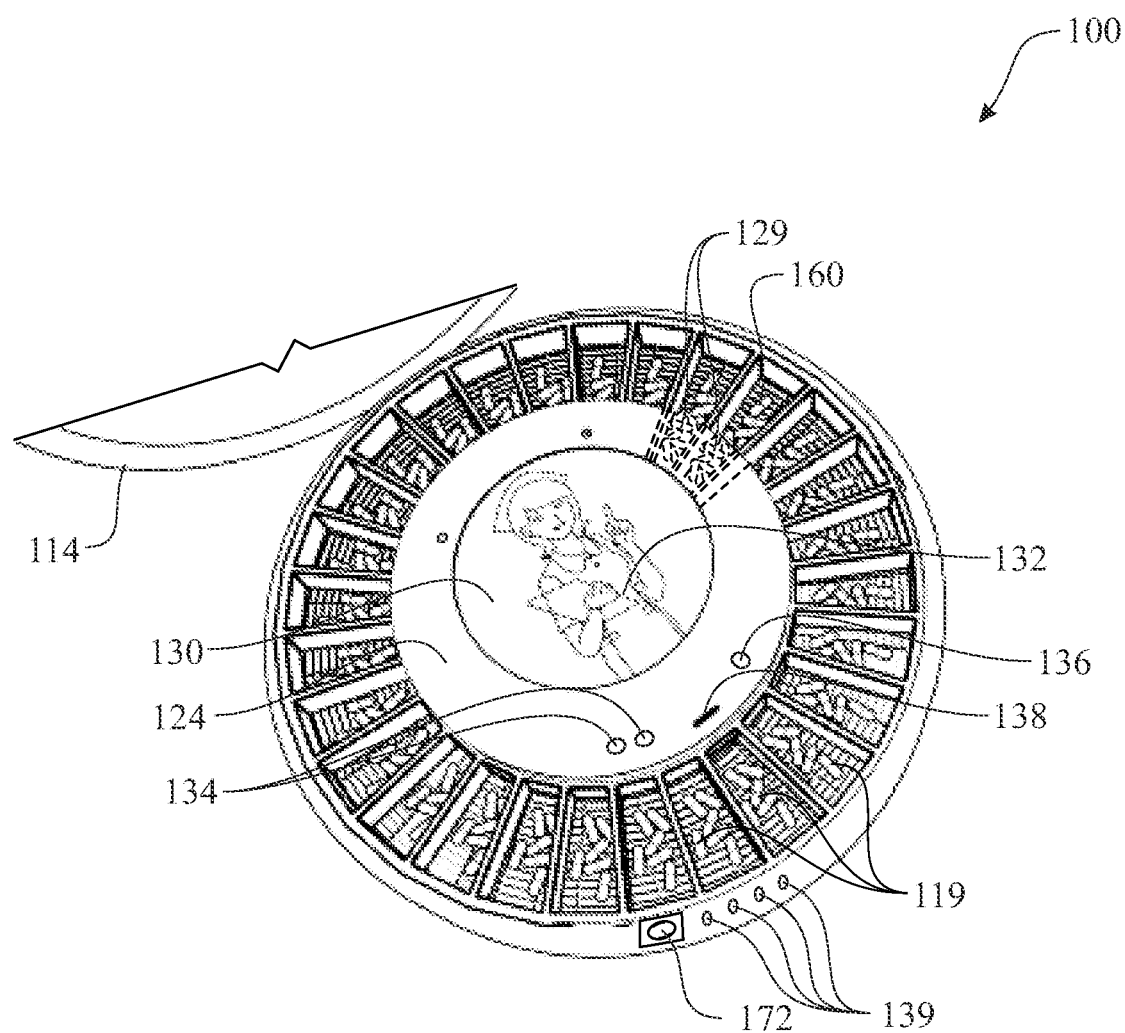
FIG. 10 presents a top, front, right side isometric view of the exemplary narcotics and Opioids secure storage and dispensing apparatus as originally introduced in FIG. 1, the illustration presenting the sealed blister pack filled with pills inserted in to the primary tray of the narcotics and Opioids secure storage and dispensing apparatus.
Figure 11:
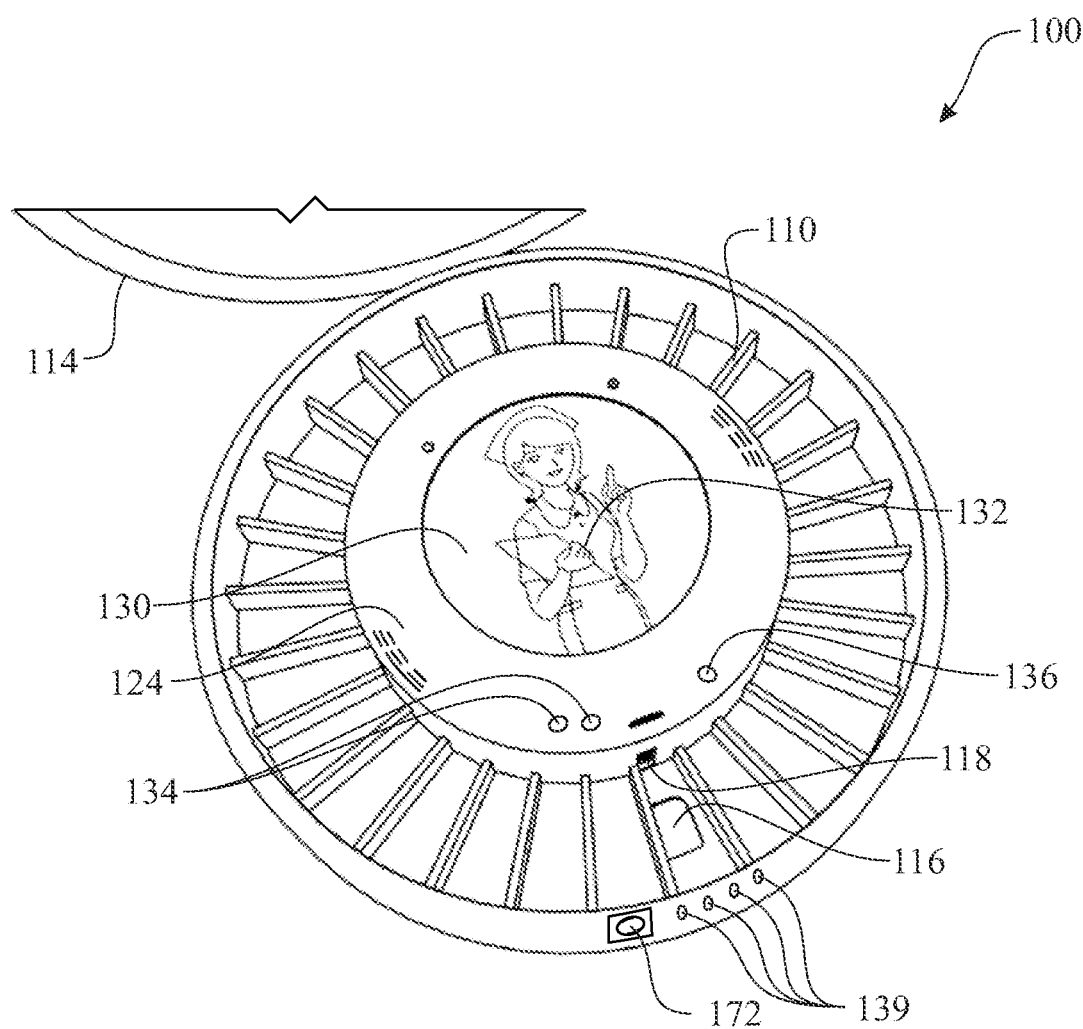
FIG. 11 presents a top, front, left side isometric view of the exemplary narcotics and Opioids secure storage and dispensing apparatus as originally introduced in FIG. 1, the illustration introducing a punch lever, the punch lever being in a fully retracted position.
Figure 12:
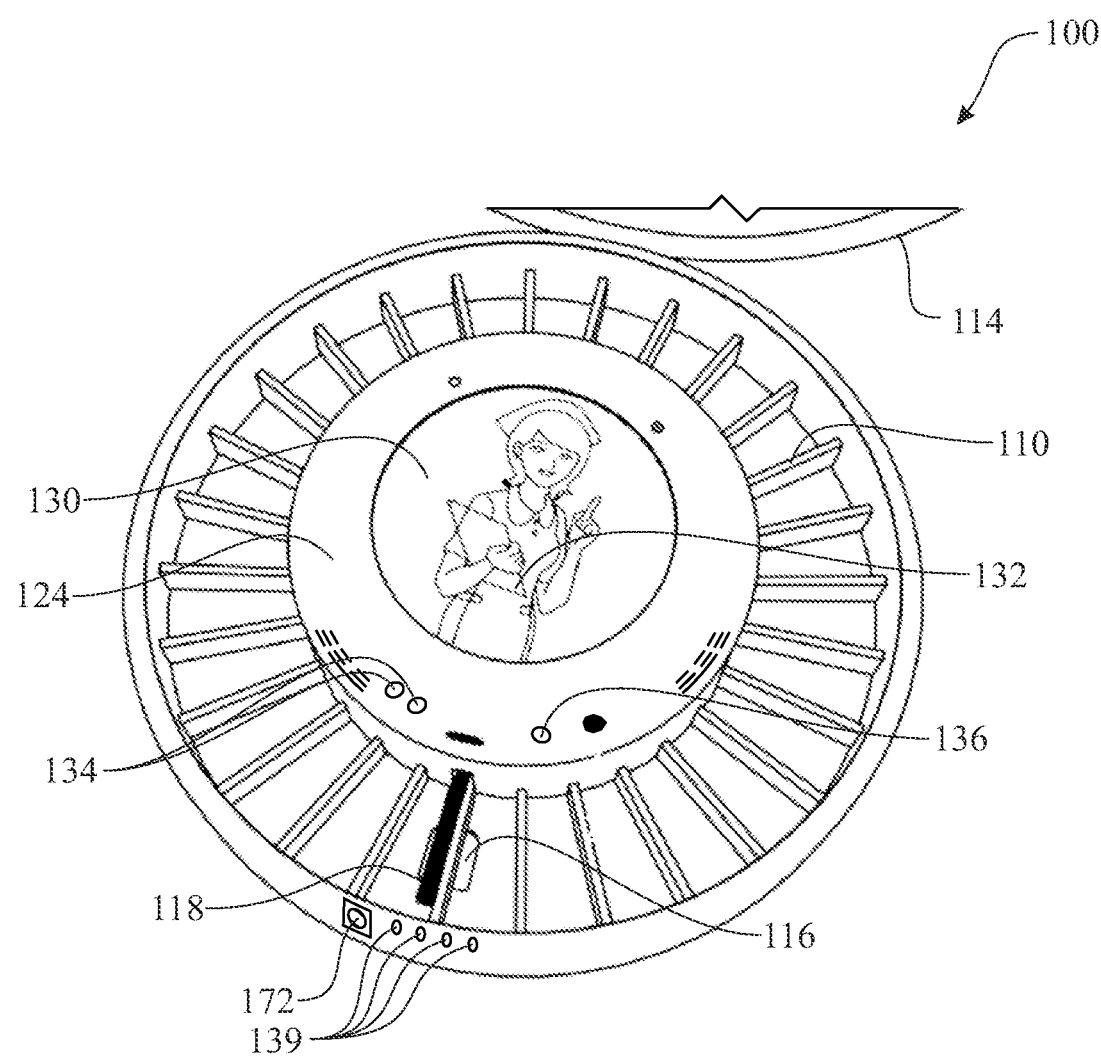
FIG. 12 presents a top, front, left side isometric view of the exemplary narcotics and Opioids secure storage and dispensing apparatus as originally introduced in FIG. 1, the illustration presenting the punch lever in a fully extended position, where the extended punch lever would tear thru the blister seal along a straight linear line.
Figure 13:
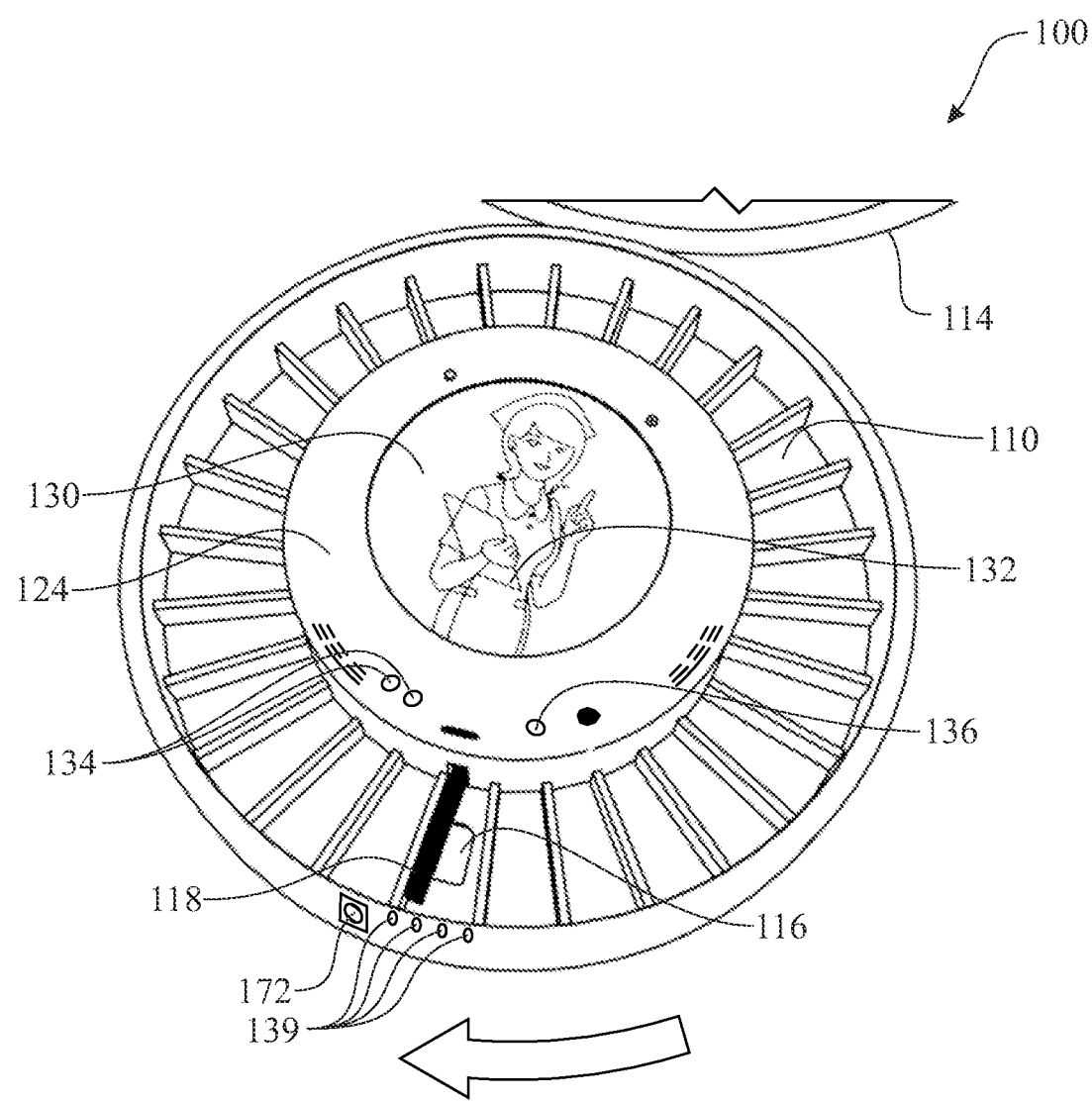
FIG. 13 presents a top, front, left side isometric view of the exemplary narcotics and Opioids secure storage and dispensing apparatus as originally introduced in FIG. 1, the illustration presenting the punch lever position in a fully extended position, where the primary tray is rotated one compartment counter-clockwise to tear an entire blister foil area.
Figure 14:
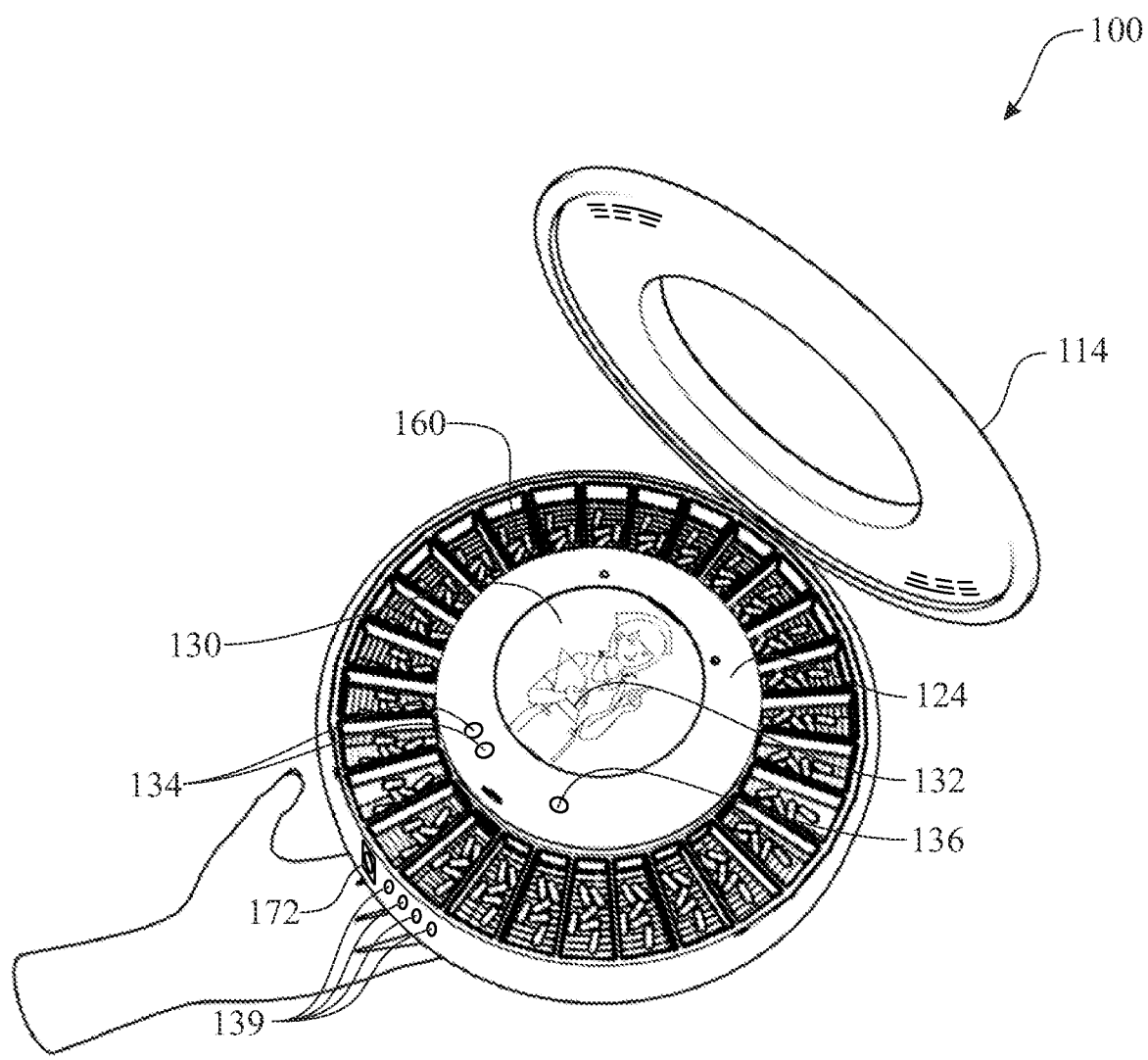
FIG. 14 presents a top, front, right side isometric view of the exemplary narcotics and Opioids secure storage and dispensing apparatus as originally introduced in FIG. 1, the illustration presenting a dispensing of pills from the blister pack of pills located within the primary tray.

The sealed blister pack 160, as shown in FIGS. 9 and 10, contains a plurality of blister pack medication compartments 162. The sealed blister pack 160 is also filled and pre-sealed with medication and placed into the primary medication tray 110 of the narcotics and Opioids secure storage and dispensing apparatus 100. A unique punching mechanism then punctures the sealed blister 160 allowing the pills contained in the blister pack 160 to be released at appropriate time scheduled.

In the dispense compartment 116, another benefit of the narcotics and Opioids secure storage and dispensing apparatus 100, is an ability to simultaneously dispense pills that were (a) manually loaded in the primary medication tray 110, (b) pills contained in the sealed blister pack 160, and supplemental pills manually placed within the secondary medication tray 120, thru a common dispense compartment 116.

Another feature of the narcotics and Opioids secure storage and dispensing apparatus 100 is a motorized punching mechanism 356 detailed in FIGS. 11 through 14. The punch lever 118 utilizes a dual cutting motion to puncture the sealed blister pack 160 and dispense the contained medication into the dispense compartment 116 at scheduled times. In its default normal mode of operation, the punch lever 118 in fully retracted inside the mechanism center core. To tear open the sealed blister pack 160 and release the contained medication, the punch lever 118 is first fully extended out along a straight path creating a straight linear tear in the sealed blister pack 160. Once the punch lever 118 is fully extend out, it will lock in that position while the primary medication compartment 110 then utilizes the primary medication tray motorized system 352 to make a rotary move to cover the entire width of one medication compartment 112 distance. As the result of the secondary rotary movement by the primary medication tray 110, the punch lever 118 will produce a full area tear of the blister pack 160 for the entire surface of one primary medication tray compartment 112. Once the compartment in the blister pack 160 is breached, the contained medication (primary medication 119 in a blister pack 160 of the primary medication tray 110 or secondary medication 129 in a blister pack 160 of the secondary medication tray 120), the dispensing medication 119, 129 would follow a path from the respective compartment 112, 122 to the dispense compartment 116 as best shown in FIG. 5.

The charging contacts 262 located within each storage shelf 260 of the storage cart 250 are arranged to create an electrical communication link with the narcotics and Opioids secure storage and dispensing apparatus charging contacts 139 to enable charging of the narcotics and Opioids secure storage and dispensing apparatus 100 while the narcotics and Opioids secure storage and dispensing apparatus 100 is docked. The charging contacts 262 within each storage shelf 260 further provide a connection circuitry for the storage cart 250 to access, log and report the ID, configuration information on each narcotics and Opioids secure storage and dispensing apparatus, as well as the medication dispensed from the primary medication tray 110, the secondary medication tray 120 and the sealed blister pack 160.

During operation, the narcotics and Opioids secure storage and dispensing apparatus 100 can include features to validate the user acquiring the contained medication. For example, the narcotics and Opioids secure storage and dispensing apparatus 100 can include a medication consumption tracking (fisheye) camera 172. The medication consumption tracking (fisheye) camera 172 can provide a multitude of features. The medication consumption tracking (fisheye) camera 172 can provide facial recognition of the user for validation of the user via biometrics. Similarly, the medication consumption tracking (fisheye) camera 172 can provide a function of an iris scanner for validation of the user via biometrics. The medication consumption tracking (fisheye) camera 172 can also be utilized to identify any unwarranted movement of the narcotics and Opioids secure storage and dispensing apparatus 100, such as in a condition where the narcotics and Opioids secure storage and dispensing apparatus 100 become inverted. Motion sensors can alternative or additionally be utilized for the same or similar function. The medication consumption tracking (fisheye) camera 172 can be used to track the medication from dispensing through ingestion. This provides a validation process that the patient has actually taken the medication.

Any, a portion, or all video acquired by the medication consumption tracking (fisheye) camera 172 can be recorded and stored in the memory module 320, transmitted to a remote storage media, transmitted to a monitoring party, or transmitted to any other desired recipient (including a portable device associated with a person, a portable device, or a fixed device, or any combination thereof).

A medication dispensing member 170 provides a controlled access to the dispense compartment 116. The medication dispensing member 170 additionally offers an option for pre-staging of medication (primary medication and/or supplemental medication) within the dispense compartment 116 prior to dispensing. The medication dispensing member 170 could be operated using a motor, a cable, hydraulic actuator, a pneumatic actuator, or any other drive mechanism. The medication dispensing member 170 can open via a hinge along one side, rotated into an open position (similar to the process for opening the bracelet compartment door 212), opened via a sliding motion, or any other suitable method of opening an automatically operated member.

Figure 8:
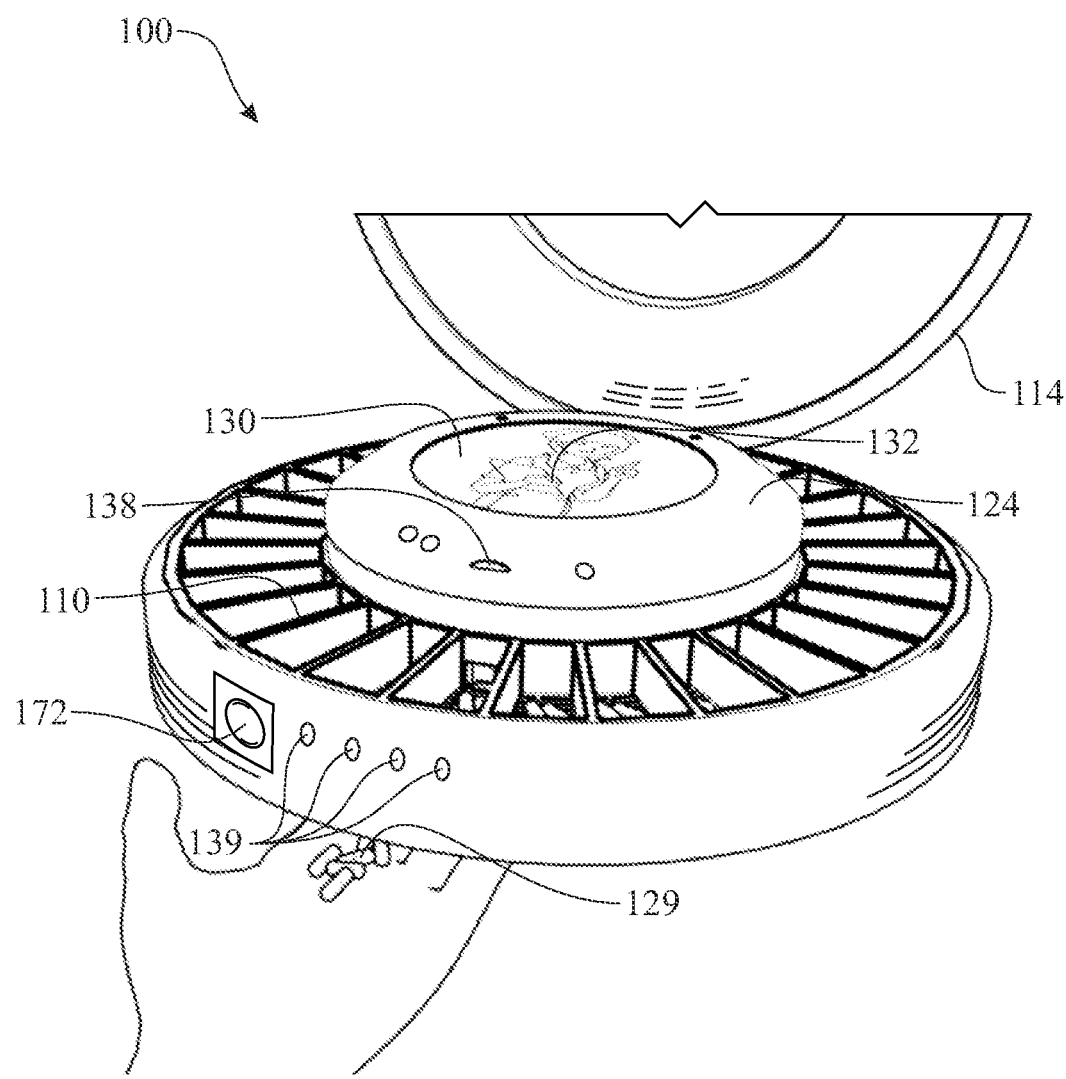
FIG. 8 presents a top, front, left side isometric view of the exemplary narcotics and Opioids secure storage and dispensing apparatus as originally introduced in FIG. 1, the illustration presenting manually loaded pills being dispensed from the primary tray.
Figure 52:
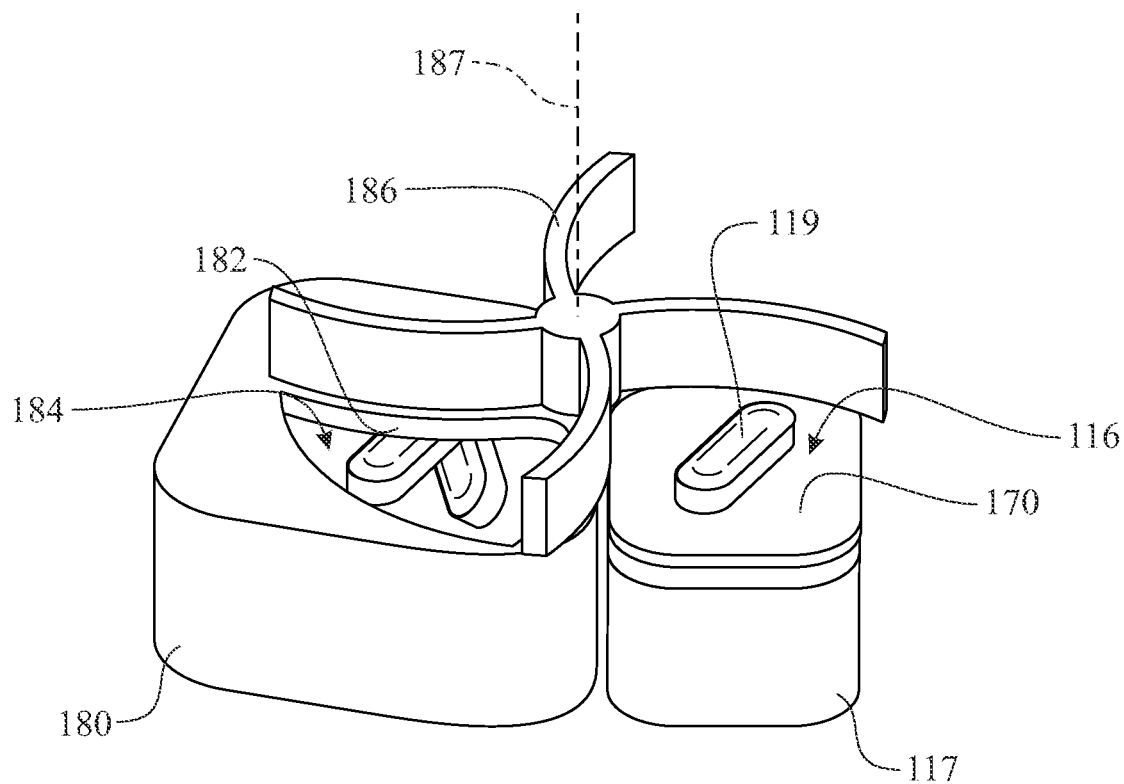
FIG. 52 presents a top, front isometric plan view of the optional medication dispensing staging system and the optional medication reclamation system originally introduced in FIG. 46, the illustration presenting a step of the pill (the exemplary primary medication) being pre-staged in the pre-staging compartment prior to being dispensed for ingestion.
Figure 53:
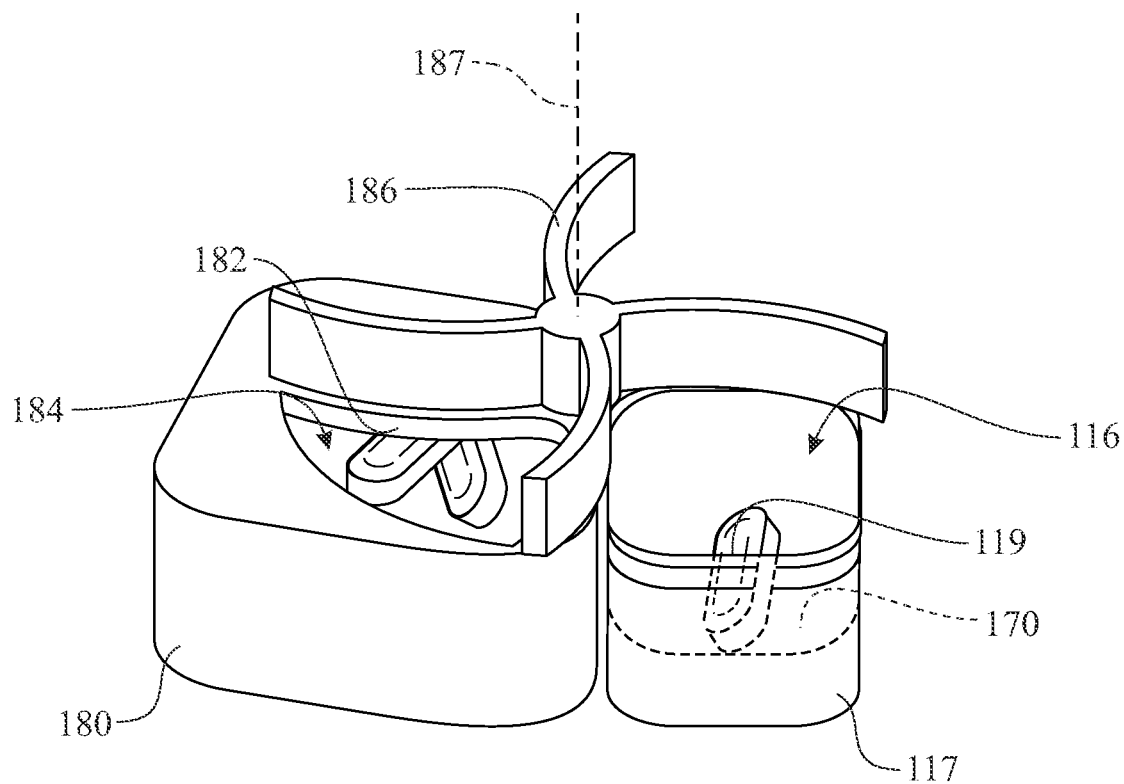
FIG. 53 presents a top, front isometric plan view of the optional medication dispensing staging system and the optional medication reclamation system originally introduced in FIG. 46, the illustration presenting a step of dispensing the pill (the exemplary primary medication) from the pre-staging compartment for ingestion.

One exemplary operation of the medication dispensing door 170 is illustrated in FIGS. 52 and 53. The primary medication 119 would be dispensed from the primary medication tray 110 into the dispense compartment 116. In the exemplary illustration in FIG. 52, the primary medication 119 rests upon an upper surface of the medication dispensing door 170. Upon approval to dispense the primary medication 119, the medication dispensing door 170 would move in accordance to the designed operation of the medication dispensing door 170 (shown as a pivoting door) allowing transfer of the primary medication 119 through a dispensing chute 117 (as illustrated in FIG. 53), and delivering the primary medication 119 to the user (as illustrated in FIG. 8). A scale 376 can be integrated into the medication dispensing door 170, enabling acquisition of a weight of the primary medication 119 prior to dispensing.

A biometric monitoring sensor 176 can be provided, preferably at a location proximate the medication dispensing member 170, enabling user validation immediately prior to dispensing the medication. Further, in an arrangement where the biometric monitoring sensor 176 is located adjacent to the medication dispensing member 170, opening of the medication dispensing member 170 can be initiated by the user placing their finger onto the biometric monitoring sensor 176, positioning their hand under the medication dispensing member 170, retaining their finger in that location while the narcotics and Opioids secure storage and dispensing apparatus 100 dispenses the medication. A medication dispense monitoring camera 174 can be integrated into the narcotics and Opioids secure storage and dispensing apparatus 100, wherein the medication dispense monitoring camera 174 is provided to acquire video during the process of dispensing the medication. This can ensure that the medication was received directly by the patient associated with the script. These features are provided to ensure that the medication is to dispense to the patient and only to the patient. The medication dispense monitoring camera 174 can function in conjunction with the medication consumption tracking (fisheye) camera 172 to acquire video from the time where the medication is dispensed through the time where the medication is ingested. The medication consumption tracking (fisheye) camera 172 can be replicated about a circumference of the body of the narcotics and Opioids secure storage and dispensing apparatus 100. The medication consumption tracking (fisheye) camera 172 can be any suitable camera, including a standard video camera, a zoom lens capability camera, a camera in a motorized mount, a camera in a motorized mount being remotely controlled, an infrared camera, a night-vision camera, or any other suitable video acquisition system. One or more light emitting elements 178 can be integrated into the narcotics and Opioids secure storage and dispensing apparatus 100 at a location proximate the dispense compartment 116. The light emitting elements 178 are provided to emit light towards the dispensing location, which can additionally support acquisition of video using the medication dispense monitoring camera 174.

Figure 45:
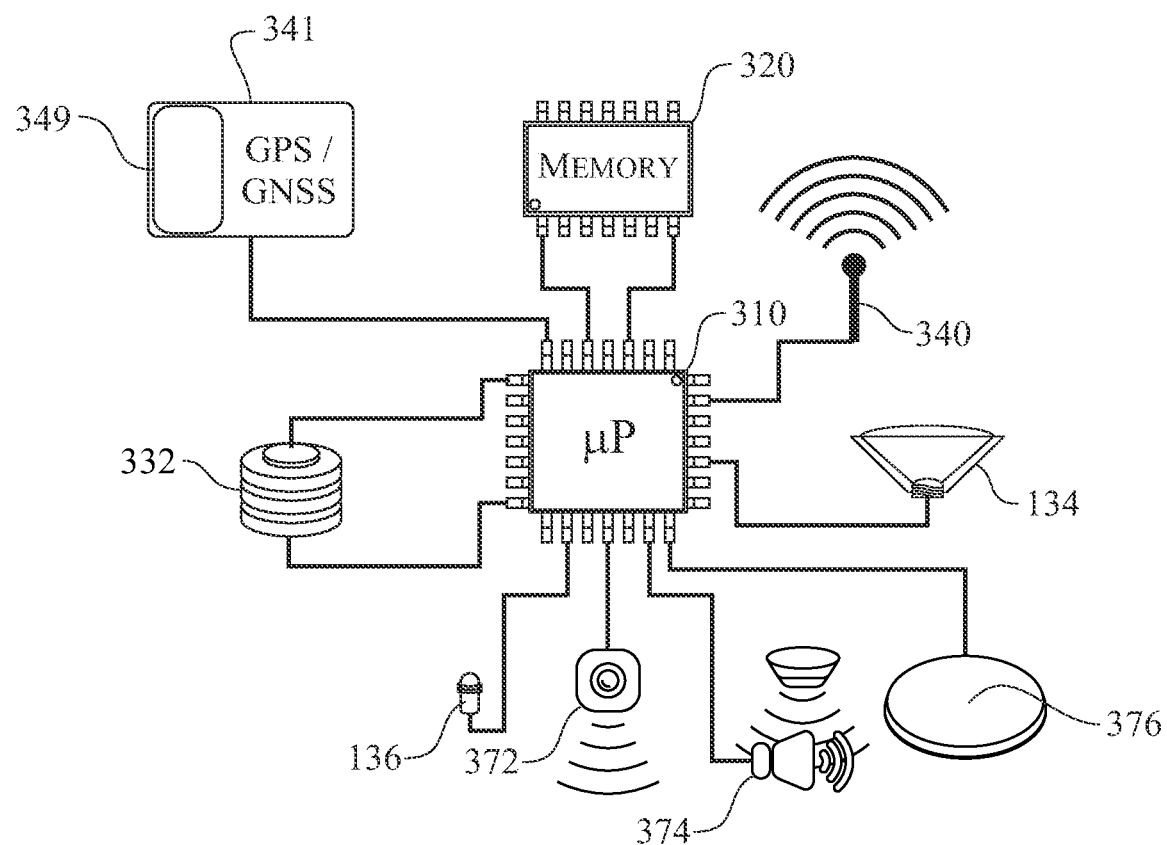
FIG. 45 presents an exemplary schematic diagram illustrating an apparatus security monitoring portion thereof.

One of the goals of the narcotics and Opioids secure storage and dispensing apparatus 100 is to enable a process for tracking the dispensing and ingestion of the medication 119, 129. A first optional process employs the GPS/GNSS 341. The inclusion of a GPS/GNSS 341 (FIG. 45) enables the narcotics and Opioids secure storage and dispensing apparatus 100 to identify a date, time, and location of the narcotics and Opioids secure storage and dispensing apparatus 100 during a specific event. The narcotics and Opioids secure storage and dispensing apparatus 100 can include an instruction set (stored in the memory module 320) to record the date, time and location when the medication 119, 129 is dispensed and/or ingested. The date, time, and location can be associated with other information acquired during the dispensing and/or ingesting of the medication 119, 129, such as video of the dispensing and/or ingestion process. The acquisition of medication dispensing documentation can be programmed by the manufacturer of the narcotics and Opioids secure storage and dispensing apparatus 100, a caregiver, a medical professional, or any other authorized person. A second optional process employs a gel-coating that can be used to encapsulate the medication 119, 129. A sensor would be embedded within the gel-coating, wherein the sensor would verify that the medication 119, 129 is placed in the mouth of the user for ingesting.

The storage/charging cart/station are illustrated in FIGS. 15 through 19. The storage cart 250 is shown comprising one or more storage shelves 260 to place and dock the narcotics and Opioids secure storage and dispensing apparatus 100. The storage cart further provides charging contacts for each storage shelf to allow charging the narcotics and Opioids secure storage and dispensing apparatus 100 while being docked. While the narcotics and Opioids secure storage and dispensing apparatus 100 are docked in the cart shelves 210, the storage cart further employs the charging contacts 212 to access, log and report the ID, configuration information on each narcotics and Opioids secure storage and dispensing apparatus 100, as well as the medication dispensed from the primary medication tray 110, the secondary medication tray 120 and the sealed blister pack 160.

The storage cart 250 is preferably portable and would include a plurality of casters. Alternatively, mobility of the storage cart 250 can be provided by integrating powered wheels, including a steering mechanism. The mobility of the storage cart 250 can be user operated, automated, or a combination thereof.

Each storage cart 250 comprises of one or more storage shelves 210 to place and dock the narcotics and Opioids secure storage and dispensing apparatus 100. The charging contacts 212 within each storage shelf 260 of the storage cart 250 allow charging of the narcotics and Opioids secure storage and dispensing apparatus 100 while being docked. The charging contacts 262 within each storage shelf 210 further provides the connection circuitry for the storage cart 250 to access, log and report the ID, configuration information on each narcotics and Opioids secure storage and dispensing apparatus 100, as well as the medication dispensed from the primary medication tray 110, the secondary medication tray 120 and the sealed blister pack 160.

The storage cart (docking station) 250 can additional include a storage cart interactive system 270. The storage cart interactive system 270 can incorporate a display (preferably a touch display), a speaker, a microphone, and any other user interface devices, such as a keyboard, a pointing device, or any other suitable user interface devices. The storage cart interactive system 270 can be assembled to the storage cart (docking station) 250 using hinges enabling the storage cart interactive system 270 to be rotated between an upright (vertical) orientation and a lowered (horizontal) orientation.

An ankle/wrist controlled medication dispensing bracelet 200 is an alternate form of the narcotics and Opioids secure storage and dispensing apparatus 100. The ankle/wrist controlled medication dispensing bracelet 200 is provided in a form factor of a bracelet in order to provide mobile dispensing and monitoring of the Opioids usage and adherence. The ankle/wrist controlled medication dispensing bracelet 200 can be configured to be placed on the user's wrist as an controlled medication dispensing bracelet 200. Alternatively, the ankle/wrist controlled medication dispensing bracelet 200 can be configured to be placed on the user's ankle.

Each ankle/wrist controlled medication dispensing bracelet 200 comprises of one or more medication compartments 210 which will contain the medication to be dispensed at scheduled time. Each medication compartment 210 of the controlled medication dispensing bracelet 200 comprises of a compartment door 212, a compartment door motor 214, and motor controller circuitry 358 to securely open and close the respective compartment door 212.

Each medication compartment 210 of ankle/wrist controlled medication dispensing bracelet 200 comprises a compartment door 212, a motorized mechanism 358, and an actuating door motor 214.

The actuating door motor 214 and the associated supporting motor controller circuitry 358 are provided for each bracelet medication compartment door 212 to securely open and close the respective compartment door 212.

The bracelet band 230 is configured to support a main bracelet control unit 220 and a plurality of the bracelet medication compartments 210.

The bracelet docking magnets provide contact points between the controlled medication dispensing bracelet 200 and the narcotics and Opioids secure storage and dispensing apparatus 100.

The main bracelet control unit 220 comprises a touch display unit 222 which provides interactive communication between the controlled medication dispensing bracelet 200) with the bracelet artificial intelligence Avatar assistant 224. The bracelet touch display 222 can also provide video communication between the user and the remote operators and caregivers.

The main bracelet control unit 220 comprises of a touch display unit 222 which provided interactive communication between the controlled medication dispensing bracelet 200 with the bracelet artificial intelligence Avatar assistant 224. The artificial intelligence virtual Avatar assistant 224 of the current invention, Opioids bracelet 200 utilizes text to speech, speech to text and Natural Language Processing (NLP) 326 technology to interactively communicate with the user, triage the user and gather relevant information regarding user's health status.

The main bracelet control unit 220 comprises of a touch display unit 222 which provided interactive communication between the controlled medication dispensing bracelet 200 with the bracelet artificial intelligence Avatar assistant 224.

The narcotics and Opioids secure storage and dispensing apparatus charging contacts 139, which are detailed in FIGS. 32 through 36, connects to the charging contacts 212 within each storage shelf 210 of the storage cart 250 to allow charging the narcotics and Opioids secure storage and dispensing apparatus 100 while being docked. The charging contacts 139 further provide the storage cart 250 with access, log and report the ID, configuration information on each narcotics and Opioids secure storage and dispensing apparatus 100, as well as the medication dispensed from the primary medication tray 110, the secondary medication tray 120 and the sealed blister pack 160.

The secondary mediation tray cover 124 further comprises of a microphone 136 which allows the artificial intelligence Avatar assistant 224 as well as the remote operators and caregivers to interactively communicate with the user. The secondary mediation tray cover 124 further comprising a speaker 134 which allows the artificial intelligence avatar assistant 224 as well as the remote operators and caregivers to interactively communicate with the user. The primary medication tray 110 comprises of multiple medication compartments 112 containing the Opioids and other medications for one or more time instances during a day such as morning, noon, afternoon and evening, as well as one or more days of the week. The secondary medication tray 120 comprises of multiple medication compartments 122 containing vitamins, supplemental medication and new additions to regular medication contained in the primary medication tray 110.

The microphone 136 can continuously monitor for sound. When the microphone 136 records a sound that the microprocessor 310 determines to be unusual, the microphone 136 continues to record, but the recording is saved.

Figure 37:
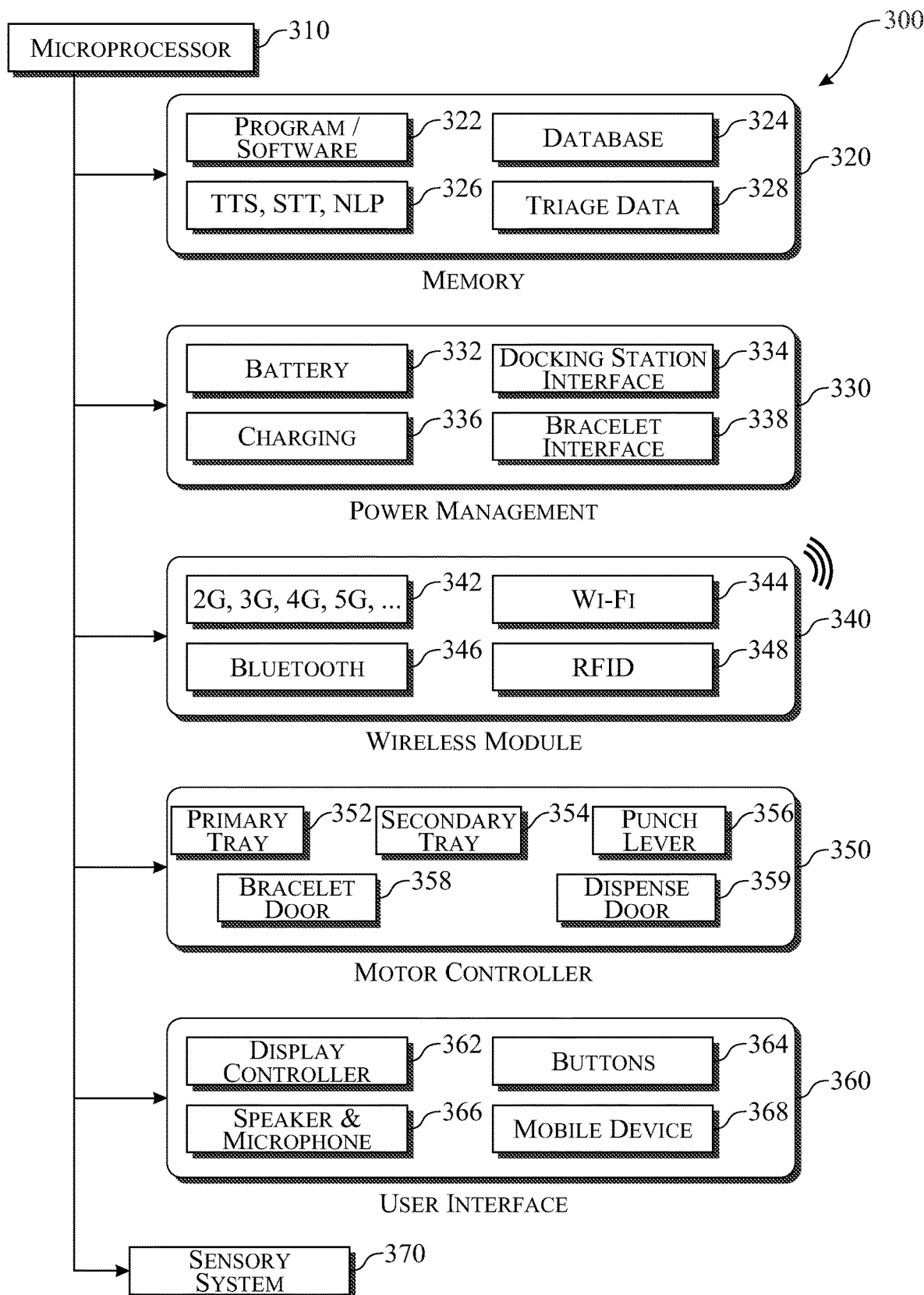
FIG. 37 presents a block diagram of elements of the narcotics and Opioids secure storage and dispensing apparatus in accordance with the present invention.

An electronic block diagram representative of the narcotics and Opioids secure storage and dispensing apparatus 300 is presented in FIG. 37. The block diagram comprises of a microcontroller 310, a memory module 320, a power management system 330, a wireless module 340, a motor controller 350, a user interface 360 and a sensory system 370.

The memory module 320 includes a storage area for the program 322, a database 324, text to speech (TTS), speech to text (STT) and Natural Language Processing (NLP) 326 as well as storage area for triage data 328.

The power management module 330 includes a battery 332, a docking station interface 334, a charging circuitry 336 and a bracelet interface 338.

Figure 46:
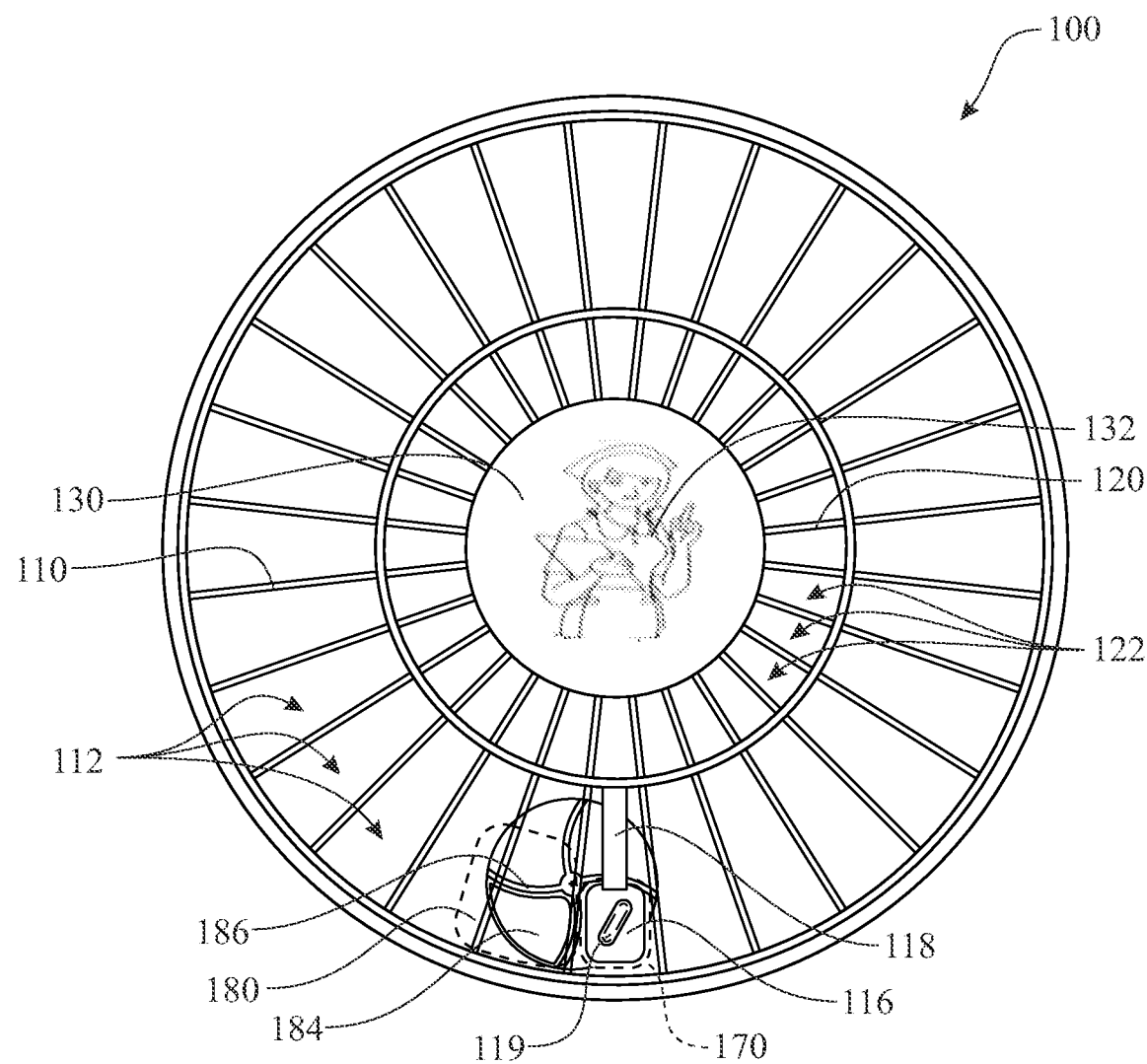
FIG. 46 presents a top plan view of the narcotics and Opioids secure storage and dispensing apparatus originally introduced in FIG. 1, the illustration introducing an optional medication dispensing staging system and an optional medication reclamation system.
Figure 47:
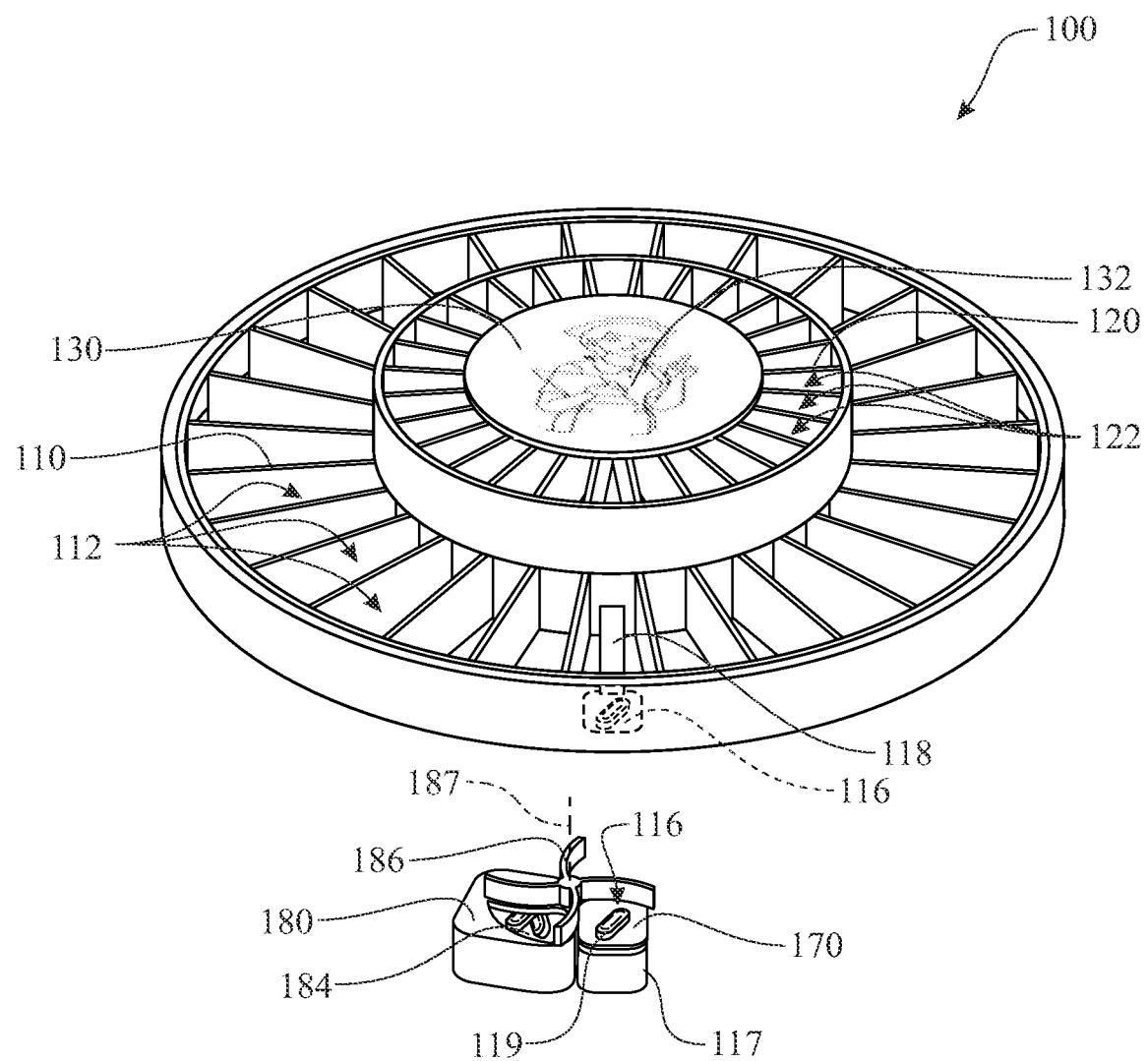
FIG. 47 presents a top, front isometric plan view of the narcotics and Opioids secure storage and dispensing apparatus originally introduced in FIG. 1, the illustration detailing the optional medication dispensing staging system and the optional medication reclamation system.

The wireless module 340 includes cellular transmission circuitry 342 for 2G, 3G, 4G and 5G, Wi-Fi circuitry 344, Bluetooth circuitry 346 and RFID circuitry 347. The wireless module 340 can additionally include a Global Positioning System (GPS)/Global Navigation Satellite System (GNSS) receiver 348 (FIG. 46) and an antenna 349 (FIG. 46).

The motor controller module 350 includes motor control circuitry for a primary tray 352, a secondary tray 354, a punch lever 356, a bracelet door 358 and a dispense door 359.

The user interface module 360 includes a display controller 362, buttons 364, a speaker and a microphone 366, and a mobile device 368.

The sensory system module 370 contains circuitry for various optical and mechanical sensors.

Figure 44A:
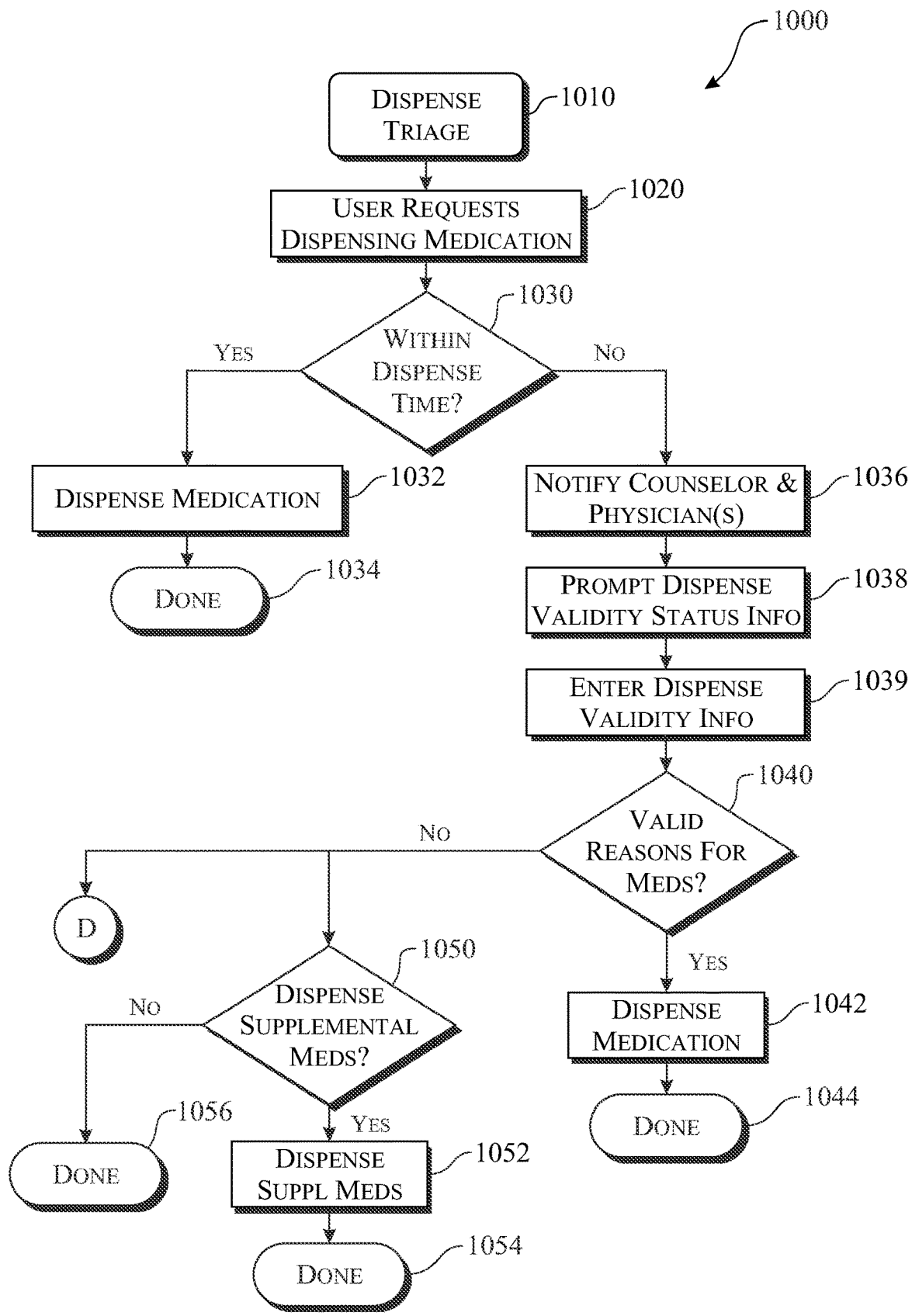
FIG. 44A presents an first portion of an exemplary flow diagram describing steps of a process for triaging a request for dispensing of medication.
Figure 44B:
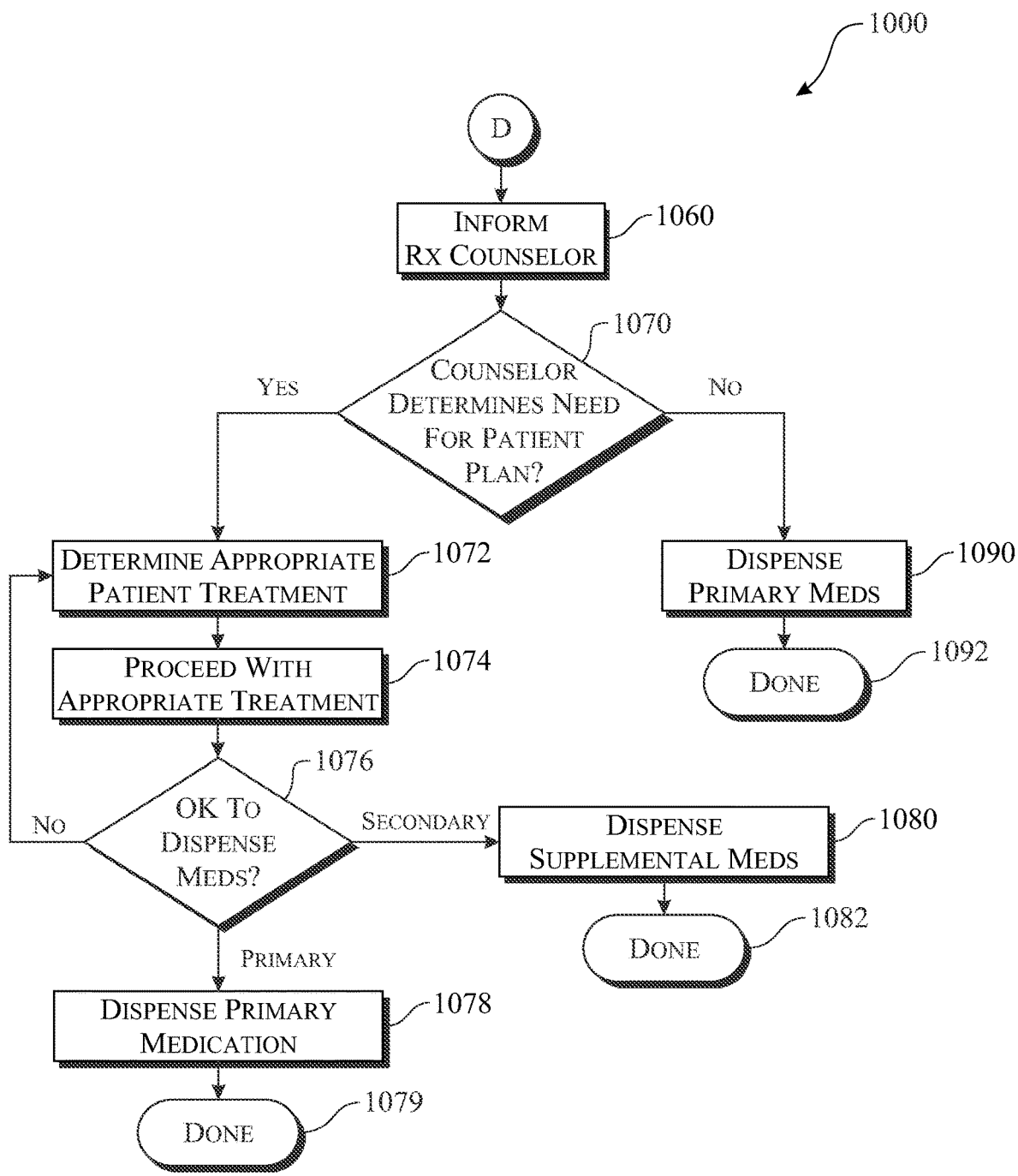
FIG. 44B presents a second portion of the exemplary flow diagram describing steps of a process for triaging a request for dispensing of medication presented in FIG. 44A.

It is critical that the narcotics and Opioids secure storage and dispensing apparatus 100 is configured to dispense the medication while ensuring against unwarranted access to the medication. This is of particular interest when dealing with narcotics, Opioids, and other schedule II drugs. Security for the narcotics and Opioids secure storage and dispensing apparatus 100 can be provided employing a number of features. Unwarranted access to the encase medication can be prevented using a security elements as introduced in FIG. 44. The exemplary security elements include a motion sensor 372 and a noise sensor 374. The motion sensor 372 can be arranged to detect general unwarranted motion as well as sudden impact or shock, generally indicative of unwarranted motion of the narcotics and Opioids secure storage and dispensing apparatus 100. This can include a person trying to gain access to the contained medication by breaking the enclosure, the top cover 114, the secondary medication tray cover 124, or any other enclosing feature of the narcotics and Opioids secure storage and dispensing apparatus 100. The noise sensor 374 can be arranged to detect general unwarranted noise, generally indicative of breakage of the enclosure of the narcotics and Opioids secure storage and dispensing apparatus 100. Other sensing devices can be employed to identify when an unwarranted activity is taking place respective to the narcotics and Opioids secure storage and dispensing apparatus 100. For example, strain gauges can be installed at potential pry points or other locations that might identify when the enclosure is being subjected to an unwarranted force. Each of the sensors would directly or indirectly provide a signal to the microprocessor 310. Power to the system is provided by the battery 332, a corded power source, a solar power source, or any other suitable power source. The microprocessor 310 can operate in accordance with an instruction set that monitors for any signals from the sensors that exceed a normal range. Upon identification of a scenario where a sensor generated a signal that exceeds the normal range or any other signal that is determined to be suspect, the microprocessor 310 would initiate an alert. The alert can include a local alert, such as a light and/or an audible alarm emitted through the speaker 134 (such as in a form of a siren or other high pitch sound generator), a remote alert by transmitting a signal to a remote receiver using the wireless module 340, or activating any other alerting function, or any combination thereof. The transmitted signal can include information identifying which sensor or sensors are providing a signal suggesting a suspect activity on the narcotics and Opioids secure storage and dispensing apparatus 100 as well as a location identified by a Global Positioning System (GPS) or a Global Navigational Satellite System (GNSS) 341. A GPS/GNSS antenna 349 would be included to support the GPS/GNSS 341 system. Additionally, the narcotics and Opioids secure storage and dispensing apparatus 100 can activate the medication consumption tracking (fisheye) camera 172 and the microphone 136 to record both video and audio following the unwarranted motion. Although the above is directed towards the narcotics and Opioids secure storage and dispensing apparatus 100, the same can be applied to the controlled medication dispensing bracelet 200.

A first scale 376 can be integrated into the narcotics and Opioids secure storage and dispensing apparatus 100, wherein the first scale 376 would be located proximate the dispense compartment 116, where the first scale 376 can acquire a weight of the medication 119, 129 staged for dispensing. A second scale 376 can be integrated into the narcotics and Opioids secure storage and dispensing apparatus 100, wherein the second scale 376 would be located at a medication reclamation safe 180 (FIGS. 46-53) within the narcotics and Opioids secure storage and dispensing apparatus 100, where medication 119, 129 that is not dispensed would be transferred to the medication reclamation safe 180 within the narcotics and Opioids secure storage and dispensing apparatus 100 and weighed using the scale 376. Every step would preferably include a process of weighing the medication 119, 129 using one or more scales 376 to track each transfer of the medication 119, 129. Weight of each pill 119, 129 is available from the manufacture and can be acquired using the wireless module 340 and stored within the memory module 320. Non-dispensed medication 119, 129 would be stored in the medication reclamation safe 180 awaiting diversion/destruction by Drug Enforcement Agency (DEA) (or other authorizing) certified facility. This function enables another important verification that no pill can ever be lost or go missing through any stage of handling by the narcotics and Opioids secure storage and dispensing apparatus 100, the user, or any other persons.

The medication would remain in the dispense compartment 116 until one of two conditions:

(a) dispensing of the primary medication 119 is appropriate. This can be based on a scheduled time for dispensing, a request by the user for dispensing of the primary medication 119, a request by the user for dispensing of the primary medication 119 that is approved by an authorizing process (either the system or a decision by an authorized person), or any other acceptable condition, (b) dispensing of the primary medication 119 is determined to be inappropriate. In this condition, the staged primary medication 119 can be forwarded to the medication reclamation safe 180. Conditions can include when a time window for dispensing of the primary medication 119 has lapsed without a request for dispensing of the primary medication 119, the user fails to meet criteria suitable for prescribing taking of the primary medication 119, or any other scenario where it would be determined inappropriate for the user to take the primary medication 119. In one scenario of this condition, it could be determined to reclaim the primary medication 119 and to dispense the supplemental medication 129, wherein the primary medication 119 would be transferred to the medication reclamation safe 180 and the supplemental medication 129 would be transferred to the 116 #for dispensing.

Figure 48:
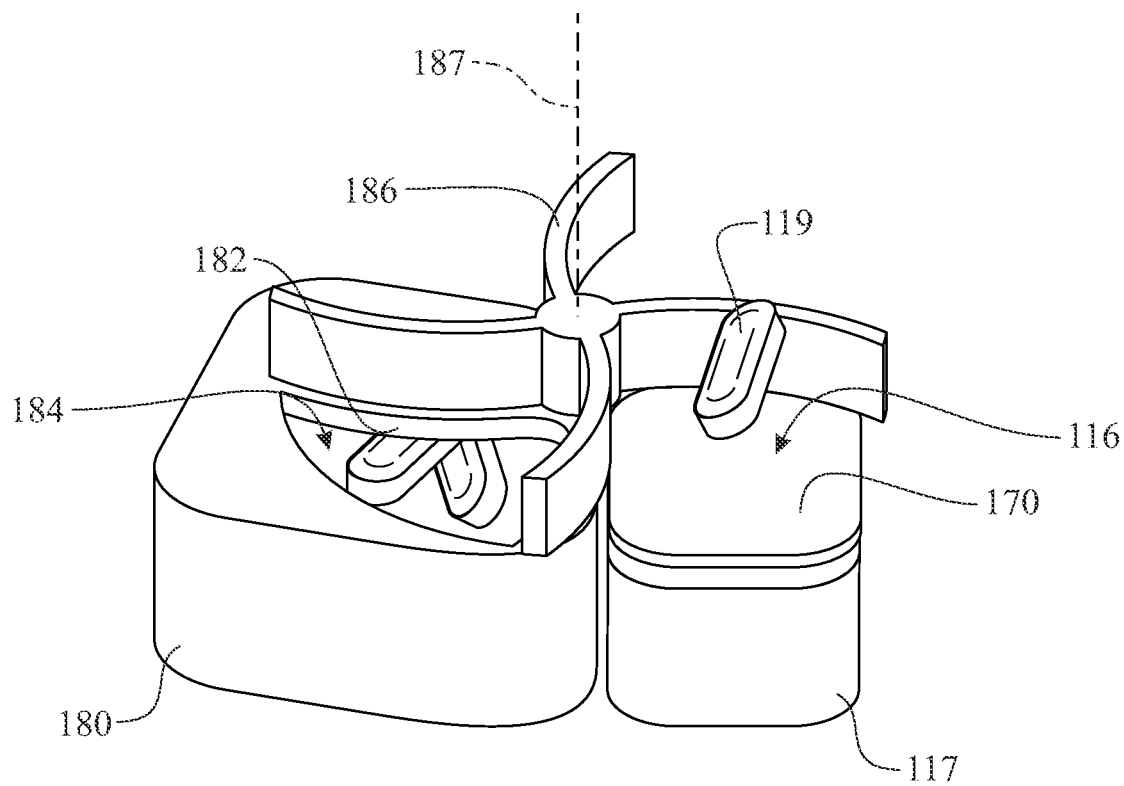
FIG. 48 presents a top, front isometric plan view of the optional medication dispensing staging system and the optional medication reclamation system originally introduced in FIG. 46, the illustration presenting a step of a pill (an exemplary primary medication) being dispensed into the pre-staging compartment of a dispensing process.
Figure 49:
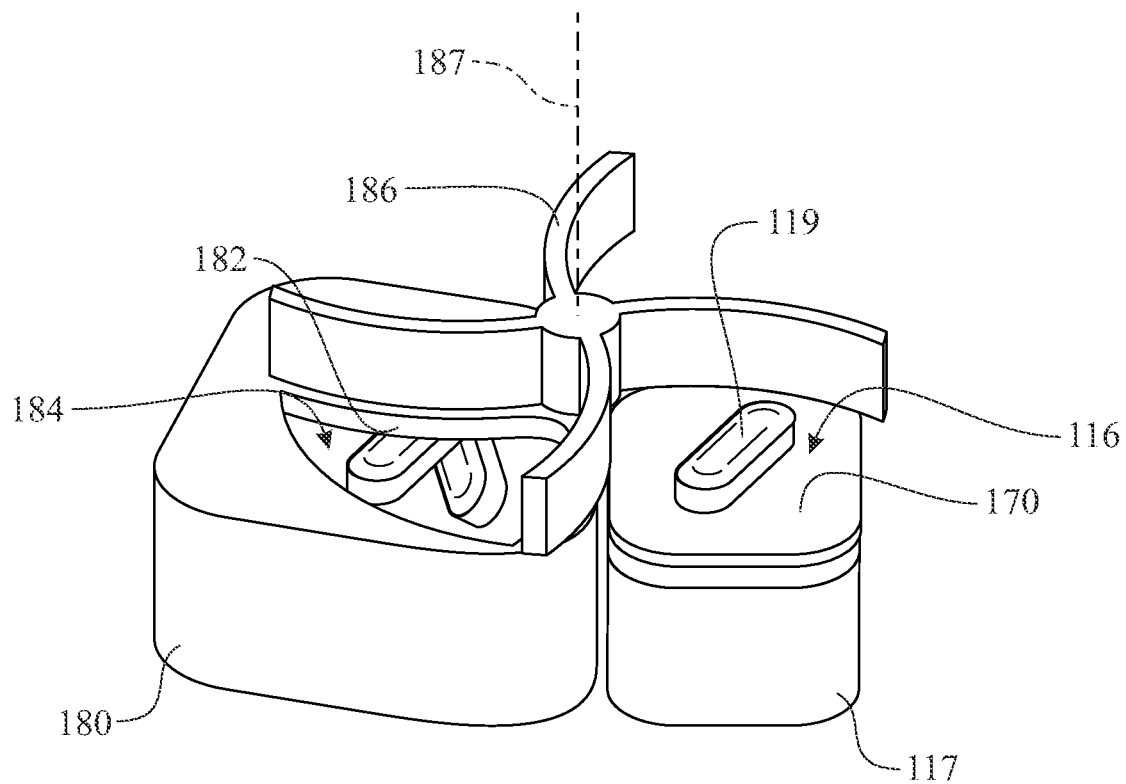
FIG. 49 presents a top, front isometric plan view of the optional medication dispensing staging system and the optional medication reclamation system originally introduced in FIG. 46, the illustration presenting a step of the pill (the exemplary primary medication) being pre-staged in the pre-staging compartment prior to being collected in a medication reclamation safe.
Figure 50:
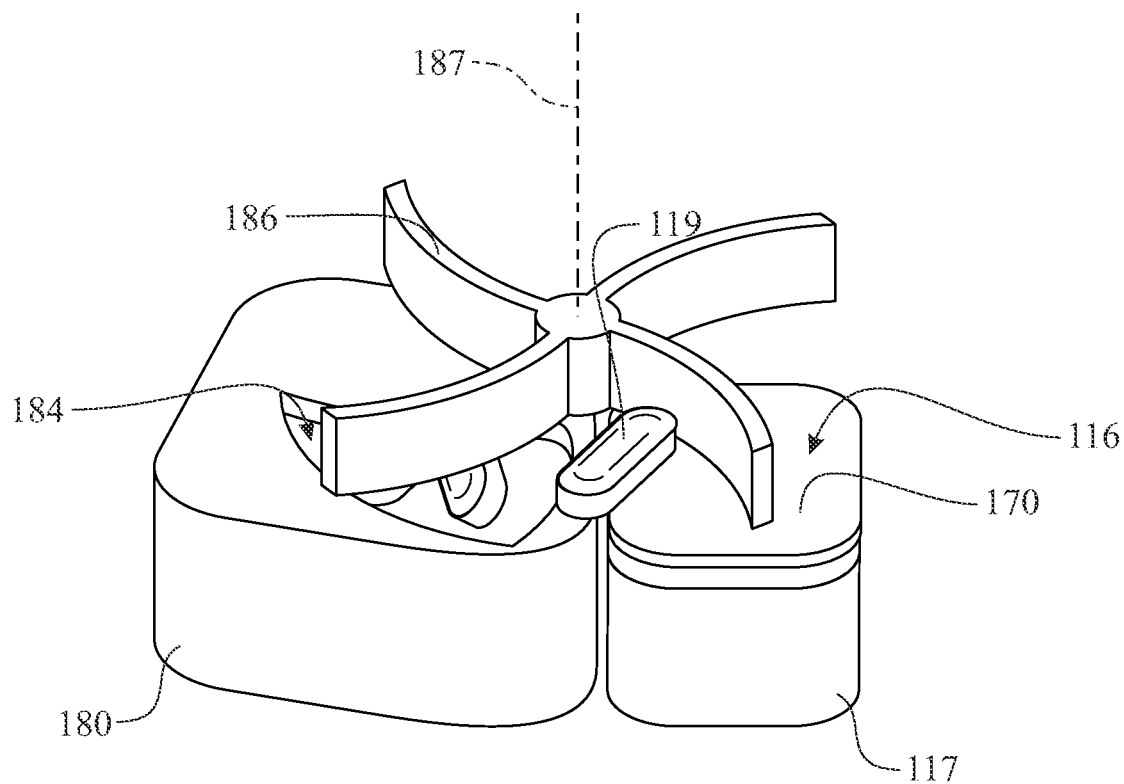
FIG. 50 presents a top, front isometric plan view of the optional medication dispensing staging system and the optional medication reclamation system originally introduced in FIG. 46, the illustration presenting a step of the pill (the exemplary primary medication) being transferred to the medication reclamation safe.
Figure 51:
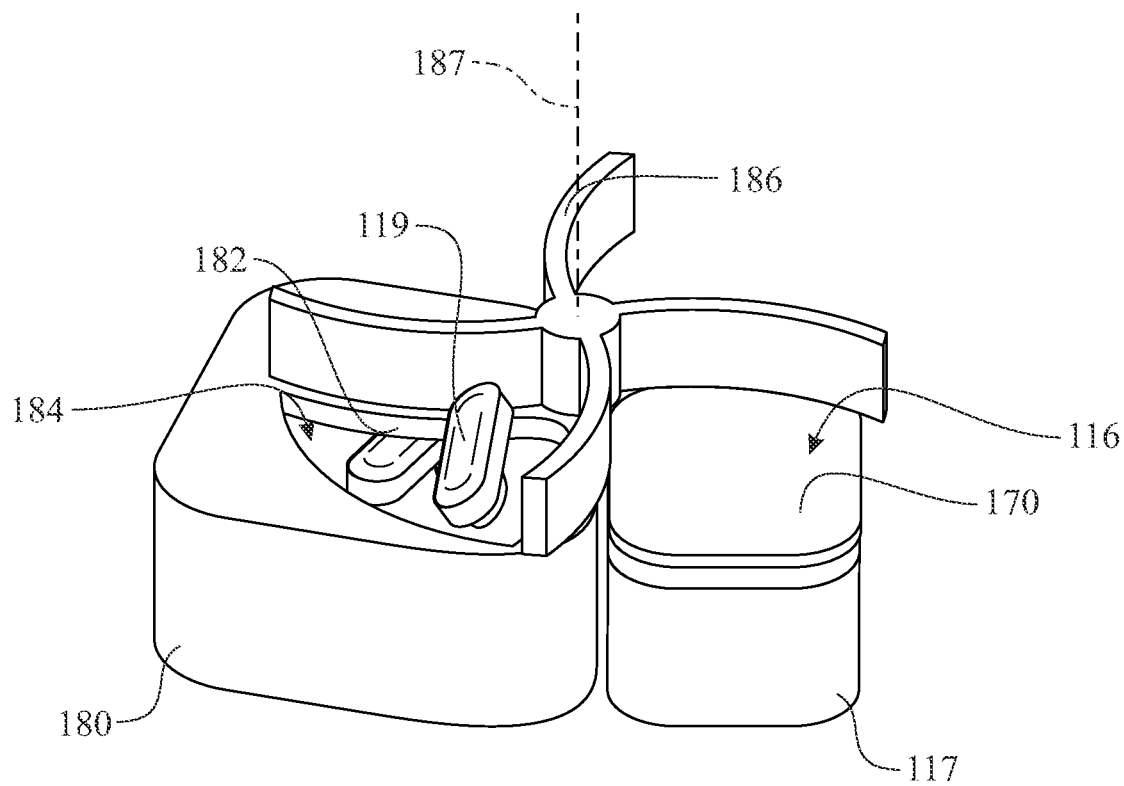
FIG. 51 presents a top, front isometric plan view of the optional medication dispensing staging system and the optional medication reclamation system originally introduced in FIG. 46, the illustration presenting a step of the pill (the exemplary primary medication) being deposited into a repository of the medication reclamation safe.

Operation of one exemplary medication reclamation system is illustrated in FIGS. 48 through 51. The primary medication 119 is dispensed into the dispense compartment 116 (as illustrated in FIG. 48), where the primary medication 119 would come to rest upon an upper surface of the medication dispensing door 170 (as illustrated in FIG. 49). In a condition where it is determined to reclaim the primary medication 119, a reclamation safe pill collection sweeper 186 is operated to transfer the primary medication 119 from the dispense compartment 116 to a reclamation safe repository 184 of the reclamation safe 180. In the exemplary illustrations, the reclamation safe pill collection sweeper 186 is provided in a form of a rotating sweeper that rotates about the upper surface of the medication dispensing door 170. One or more walls (not shown for clarity) can be provided to encapsulate the dispense compartment 116, while enabling operational motion of the reclamation safe pill collection sweeper 186. The reclamation safe pill collection sweeper 186 would continue to move, transferring the primary medication 119 from the dispense compartment 116 to a position over the reclamation safe repositing aperture 182 of the reclamation safe 180. The primary medication 119 would drop through the reclamation safe repositing aperture 182, into the reclamation safe repository 184 (as illustrated in FIG. 51). In the exemplary illustrated version of the medication reclamation system, the reclamation safe pill collection sweeper 186 rotates about a reclamation safe pill collection sweeper rotational axis 187. Although the exemplary reclamation safe pill collection sweeper 186 is illustrated as a rotating member, the reclamation safe pill collection sweeper 186 can be designed to move in accordance with any suitable motion, including a rotating motion, a hinged motion, a sliding motion, and the like. A reclamation safe repository cover (not shown for clarity) can be integrated into a portion of the reclamation safe pill collection sweeper 186 between two adjacent sweeping elements to adequately seal the reclamation safe repositing aperture 182 when the reclamation safe pill collection sweeper 186 is not operating. At a desired time, collected primary medication 119 can be recovered from the reclamation safe 180 using any suitable access process. This can include a mechanical lock, an electronic lock, or any other suitable controlled access system.

A scale 376 can be integrated into the reclamation safe 180 to track a weight of the primary medication 119 being deposited within the reclamation safe repository 184.

Figure 38:
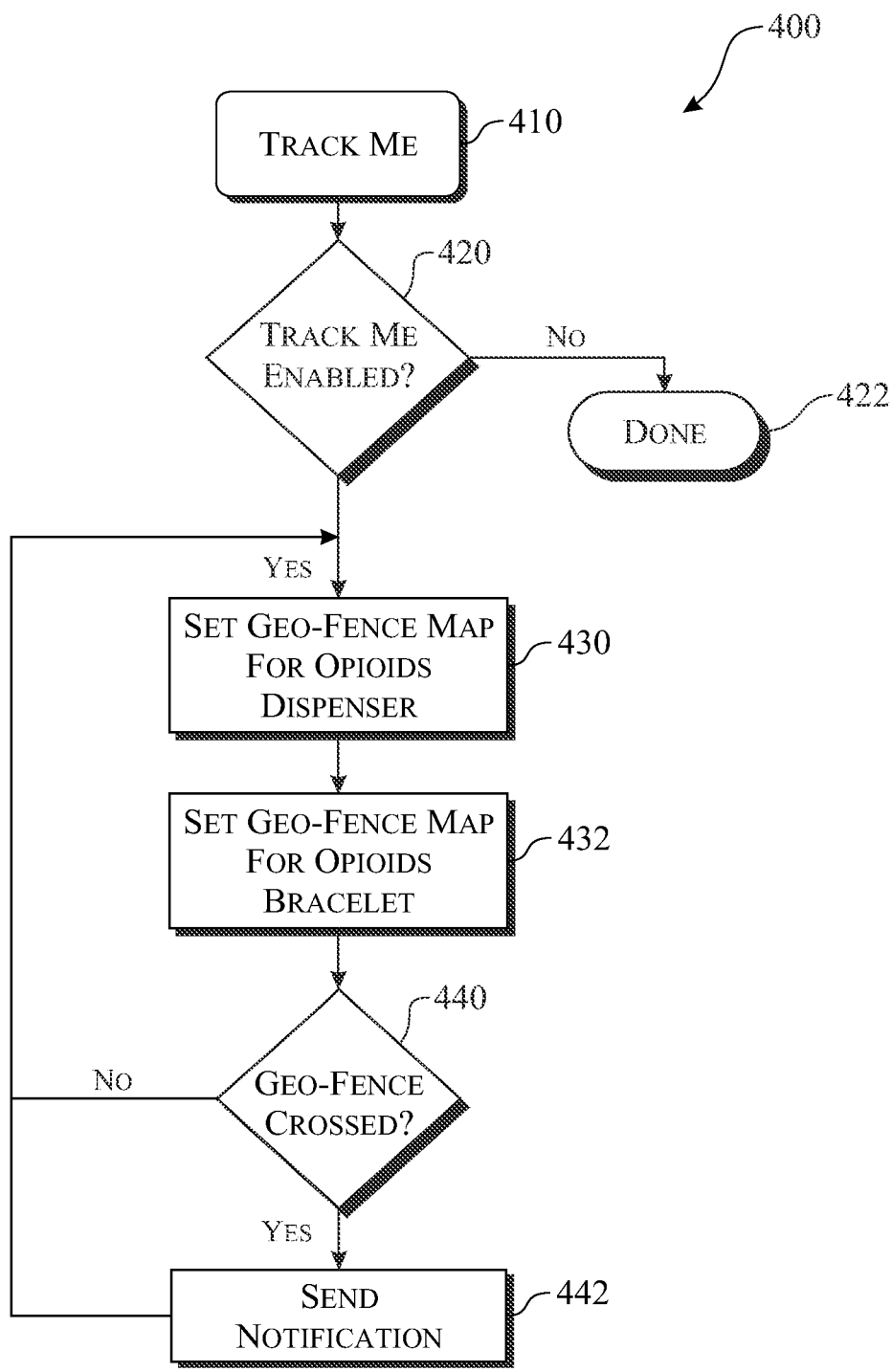
FIG. 38 presents an exemplary flow diagram describing steps of a "track me" process.

A track me process 400 for use in conjunction with the narcotics and Opioids secure storage and dispensing apparatus 100 is presented in FIG. 38. The track me process 400 begins (step 410) with a decision step to determine whether the track me process 400 is enabled (decision step 420). If the track me process is not enabled, then the track me process 400 terminates (step 422). If the track me process 400 is enabled, then the track me process 400 continues within a continuous loop. A geo-fence for the narcotics and Opioids secure storage and dispensing apparatus 100 is established (step 430), followed by a setting of a geo-fence for the Opioids bracelet 200 (step 432). Next, Global Positioning System (GPS) locations are checked to see if the any of the narcotics and Opioids secure storage and dispensing apparatuses 100 or the controlled medication dispensing bracelets 200 cross their respective geo-fences (decision step 440). If geo-fence has not been crossed (decision step 440), then the process loops back and continues setting the geo-fence area (steps 430, 432) and checking to see if either device has crossed the designated area (decision step 440). In the event that geo-fence is crossed (decision step 440), notifications are sent to remote operators and caregivers (step 442). The process again, loops back and continues setting the geo-fence area (steps 430, 432) and checking to see if either device has crossed the designated area (decision step 440). In one option, in a condition where the geo-fence has been breached, the narcotics and Opioids secure storage and dispensing apparatus 100 would lock and transmit a notification to at least one recipient that the narcotics and Opioids secure storage and dispensing apparatus 100 has breached the geo-fence.

Figure 39:
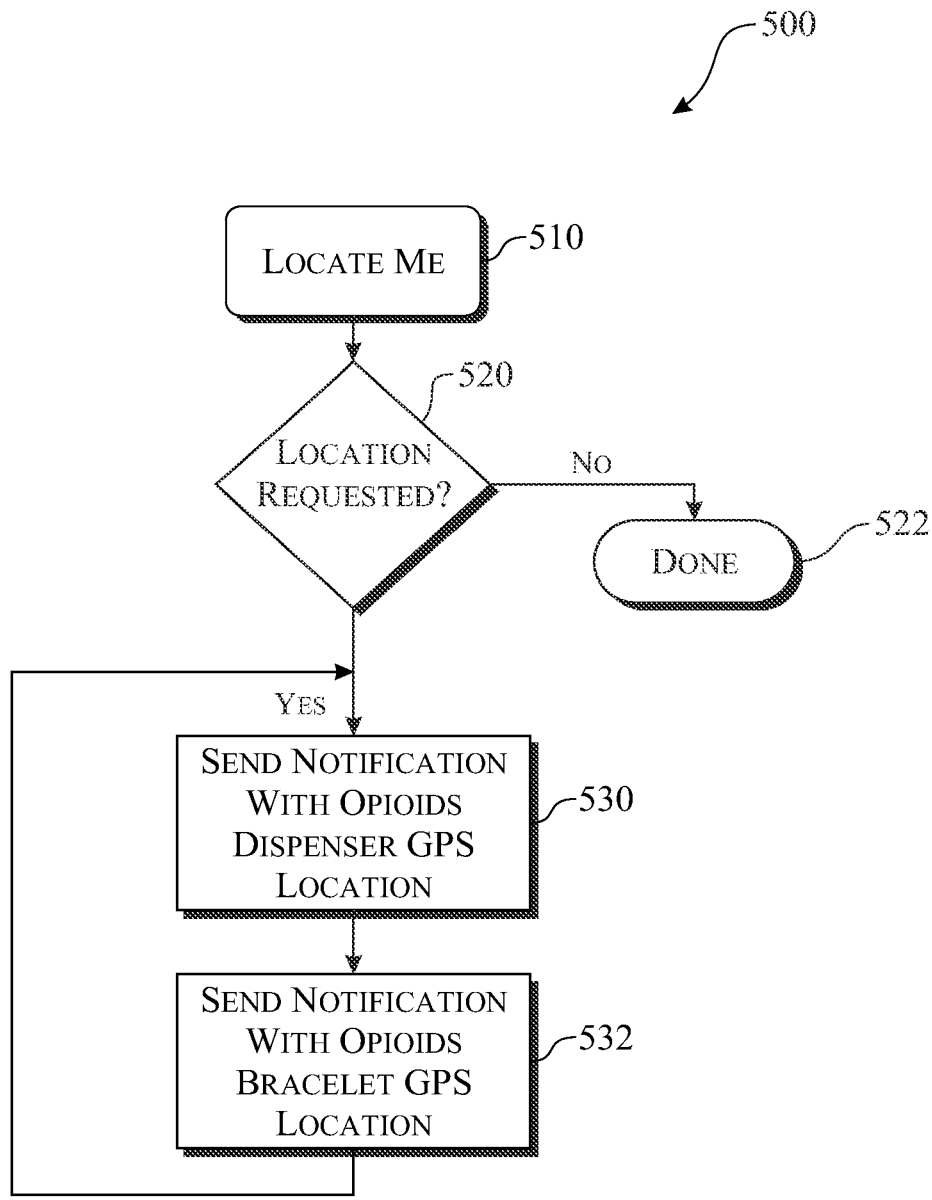
FIG. 39 presents an exemplary flow diagram describing steps of a "locate me" process.

A locate me process 500 for use in conjunction with the narcotics and Opioids secure storage and dispensing apparatus 100 is presented in FIG. 39. The locate me process 500 begins (step 510) with a check as to whether the process is enabled 390*b* (decision step 520). If the locate me process 500 is not enabled, then the process terminates (step 522). If the process is enabled, the locate me process 500 then enters a continuous loop which sends a notification of the Opioids Dispenser GPS location (step 530). This is followed by a step of sending a notification of the Opioid Bracelet GPS location (step 532).

Figure 40:
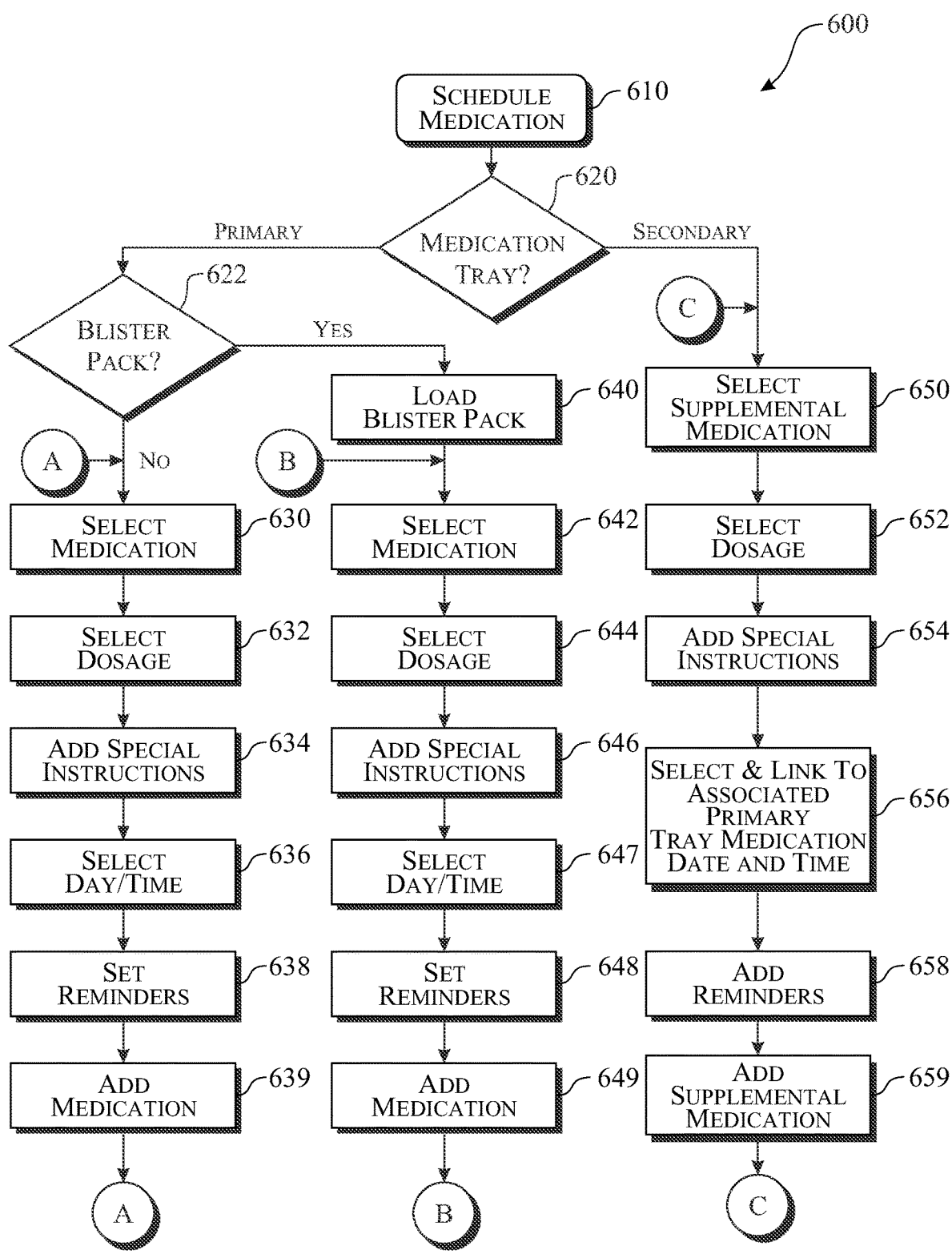
FIG. 40 presents an exemplary flow diagram describing steps of a process for scheduling dispensing of medication.

A schedule medication process 600 for use in conjunction with the narcotics and Opioids secure storage and dispensing apparatus 100 is presented in FIG. 40. The schedule medication process 600 begins with an activation of the schedule medication interface (step 610) in a condition where the schedule medication process 600 is enabled. The schedule medication process 600 checks for the availability of a medication tray in the primary medication compartment and the secondary medication compartment.

Medication can be loaded independently into the narcotics and Opioids secure storage and dispensing apparatus 100 or inserted in a prefilled blister pack 160. The primary medication scheduling process 600 identifies which tray is going to be dispensing the medication (decision step 620).

The primary medication scheduling checks for a blister pack 160 (step 622). If there is no blister pack 160, the primary medication scheduling process prompts a loading of a blister pack (step 640). The primary medication scheduling process prompts for the selection of the medication (step 642). After selection the medication (step 642), the primary medication scheduling process 600 then prompts for a dosage selection (step 644). The primary medication scheduling process 600 prompts for an addition of any special instructions (step 646). Next, the schedule medication process 600 prompts for the selection of a date and a time for administration of the medication (step 637). The next prompt pops up, requesting entry to setting reminders as to when to take the medication (step 648). The primary medication scheduling process 600 then prompts for adding medication (step 649).

If there is a blister pack 160 contained in the primary medication tray 110 (as determined by decision step 622), the schedule medication process 600 will ask for a selection of the medication (step 630). After that, the schedule medication process 600 will then prompts for entry of a dosage selection (step 632). The schedule medication process 600 prompts for the addition of any special instructions (step 634). Next, the schedule medication process 600 prompts for the selection of a date and a time for administration of the medication (step 636). The next prompt is for setting reminders as to when to take the medication (step 638). The schedule medication process 600 then presents a prompt for adding medication (step 639).

The secondary medication scheduling portion involves selecting the supplemental medication (step 650). After the supplemental medication has been set, the secondary medication scheduling portion prompts for a dosage selection (step 652). After the dosage selection has been completed, the secondary medication scheduling portion prompts for the addition of any special instructions (step 654). After entry of any special instructions has been completed, the secondary medication scheduling portion prompts the selection of a date and time for dispensing the supplemental medication and links the scheduled date and time for dispensing the supplemental medication with the scheduled date and time for dispensing the medication from the primary tray medication (step 656). After that has been completed, the secondary medication scheduling portion prompts for the addition of reminders (step 658). After that is done, the secondary medication scheduling portion prompts for the refill or addition of supplemental medication (step 659).

Figure 41:
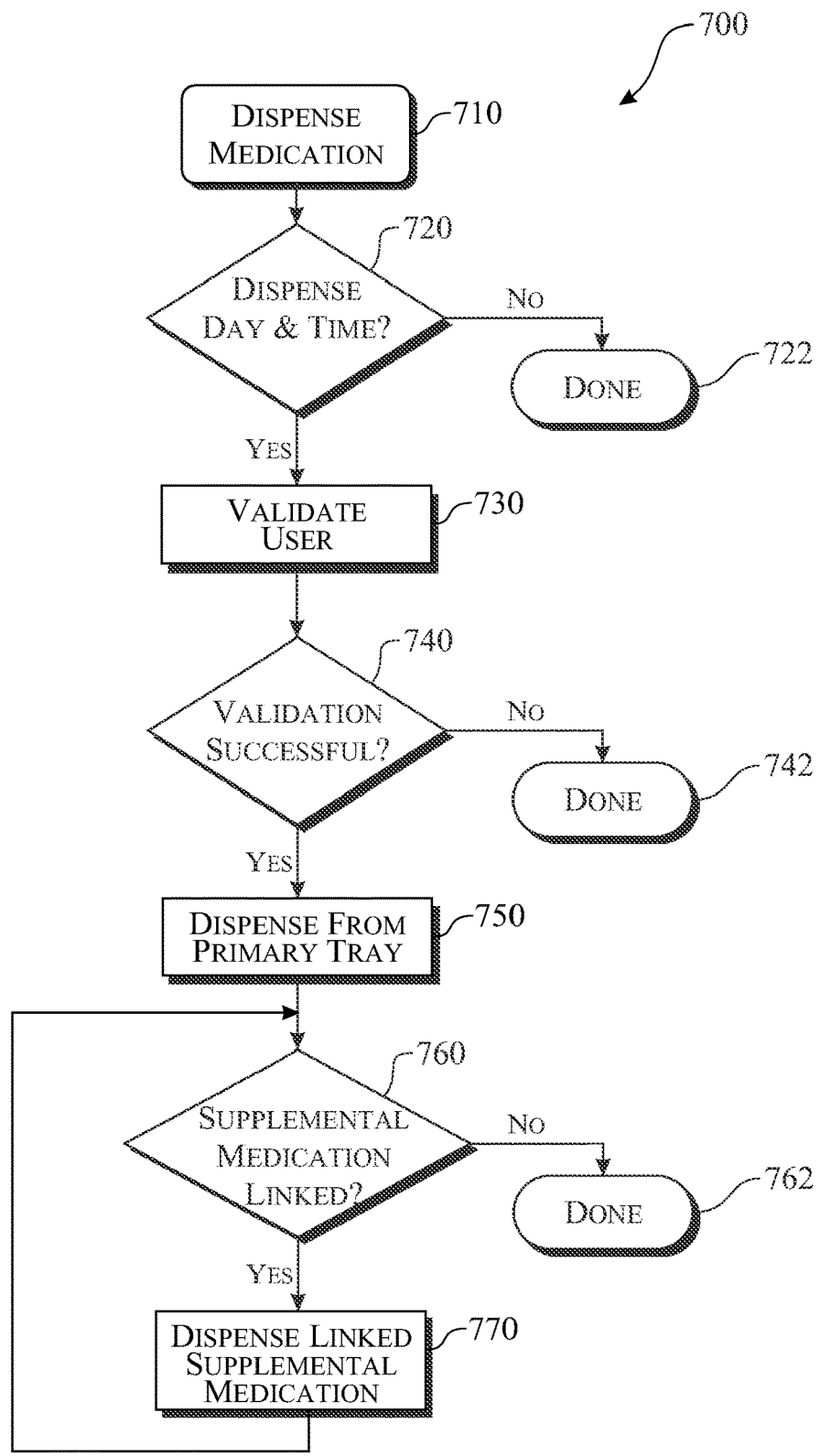
FIG. 41 presents an exemplary flow diagram describing steps of a process for dispensing medication.

A dispense medication process 700 for use in conjunction with the narcotics and Opioids secure storage and dispensing apparatus 100 is presented in FIG. 41. In a high level summary, the dispense medication process 700 involves a step of determining the dispense day and time (step 720), validation of the user (step 730), dispensing from the primary tray (step 750) and finally linking supplemental medication (steps 760, 762, 764). The dispense medication process 700 begins with a check to determine whether the process is enabled (step 710). If the process is enabled (step 710), then the dispense medication process 700 checks for the date and time (step 720). If it is not time for administration of a medication then the process terminates (step 722). If dispense medication process 700 determines that it is time for the medication the dispense medication process 700 the dispense medication process 700 proceeds to validate the user taking the medication (step 730). If the validation fails, the process terminates and nothing happens (step 742). If the validation is successful (decision step 740) the dispense medication process 700 dispenses medication from the primary tray (step 750). After dispensing the medication from the primary tray (step 750), the dispense medication process 700 checks if any supplemental medication is linked (decision step 760). If no supplemental medication is linked, the process terminates (step 762). If any supplemental medication is linked, the dispense medication process 700 dispenses the supplemental medication (step 770).

Figure 42:
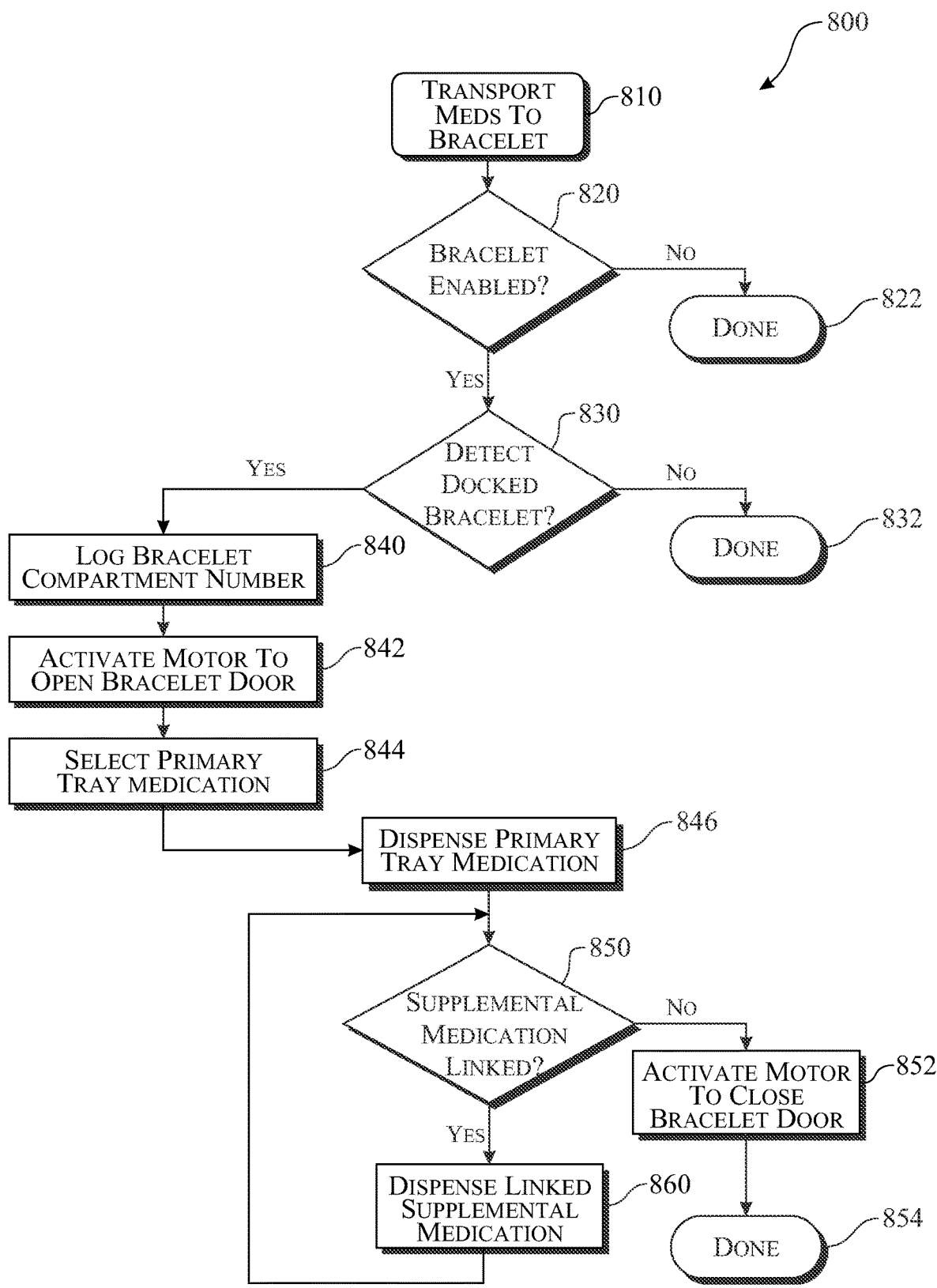
FIG. 42 presents an exemplary flow diagram describing steps of a process for transferring medication to the bracelet.

Referring to FIG. 42 shows a transport meds to bracelet process 800 for use in conjunction with the narcotics and Opioids secure storage and dispensing apparatus 100 is presented in FIG. 42. In the transport meds to bracelet process 800, a bracelet 200 is enabled and the docked bracelet 200 is verified prior to dispensing any primary tray medication. The transport meds to bracelet process 800 initiates (step 810), then determines if transporting the medication from the narcotics and Opioids secure storage and dispensing apparatus 100 to the controlled medication dispensing bracelet 200 is authorized. If the transfer of medication is not authorized, the process terminates (step 822). If the transfer of medication is authorization, the transport meds to bracelet process 800 proceeds to detect if a bracelet 200 is docked (decision step 830). If the decision step 830 determines that a bracelet 200 is not docked, then the process terminates (step 832). If a docked bracelet 200 is detected, the transport meds to bracelet process 800 logs the bracelet identifier and the bracelet compartment number receiving the medication (step 840). The transport meds to bracelet process 800 activates a motor to open the bracelet compartment door 212 (step 842). Then, the primary medication tray 110 is selected (step 844). Next, medication is dispensed from the primary medication tray 110 into the bracelet 200 (step 846). Continuing, the transport meds to bracelet process 800 checks if supplemental medication is linked (decision step 850). If supplemental medication is not linked to the primary medication, the transport meds to bracelet process 800 activates the motor to close the bracelet compartment door 212 (step 852), and the transport meds to bracelet process 800 terminates (step 854). If there is a link between primary medication and supplemental medication, the transport meds to bracelet process 800 dispenses the supplemental medication accordingly (step 860).

Figure 43:
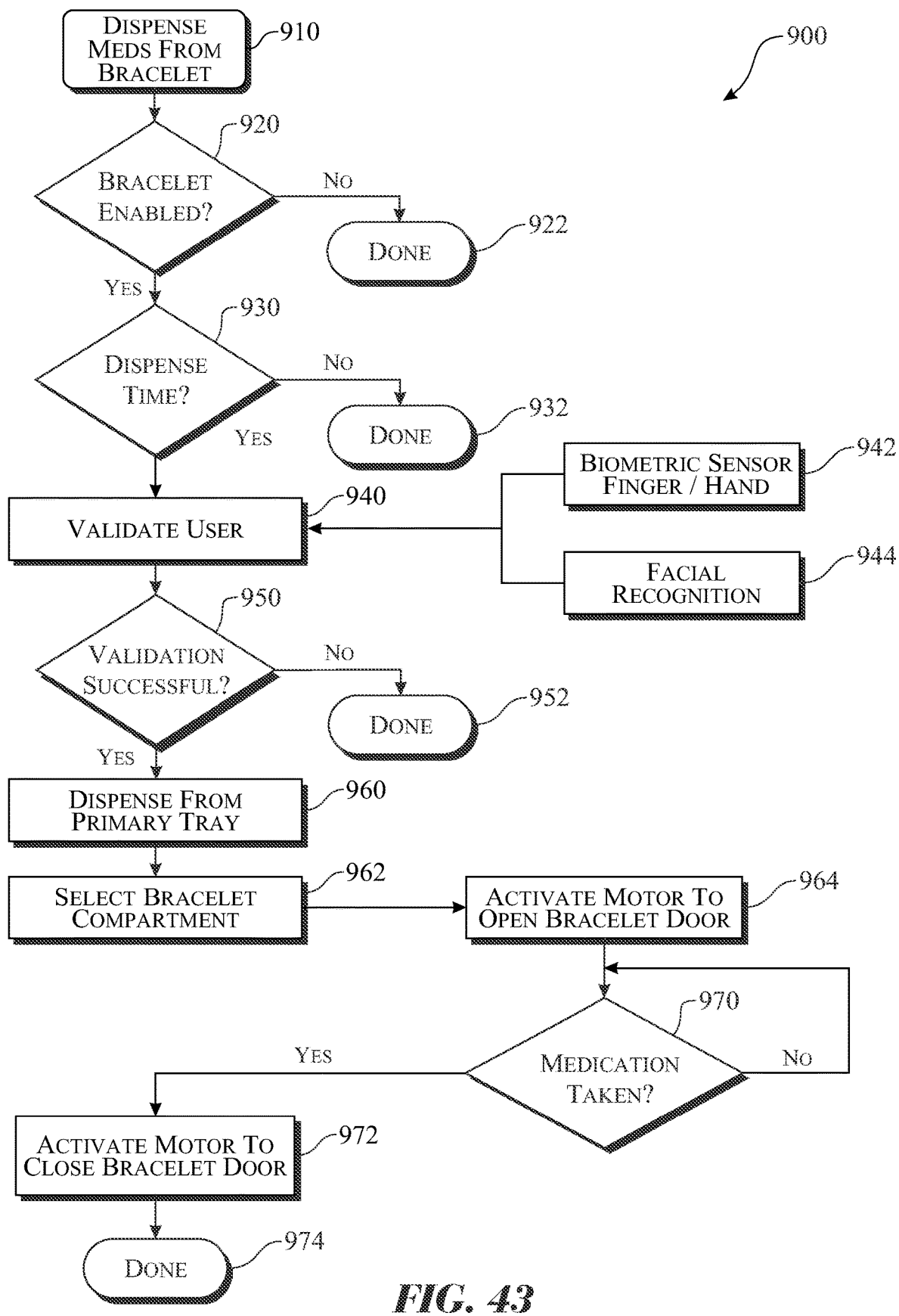
FIG. 43 presents an exemplary flow diagram describing steps of a process for dispensing medication from the bracelet.

A dispense meds from bracelet process 900 for use in conjunction with the narcotics and Opioids secure storage and dispensing apparatus 100 is presented in FIG. 43. The dispense meds from bracelet process 900 determines if a controlled medication dispensing bracelet 200 is enabled (decision step 920), followed by a step of determining a dispense time (step 930). As soon as a user validation process (step 940) is completed, a motor is activated to open the bracelet compartment door 212 (step 964) and medication within the respective compartment is taken prior to closing the bracelet compartment door 212. The dispense meds from bracelet process 900 dispense meds from bracelet process 900 initiates with a step of checking for the availability of medication (step 910). The dispense meds from bracelet process 900 then checks to verify that the controlled medication dispensing bracelet 200 is enabled (decision step 920). If the controlled medication dispensing bracelet 200 is not enabled, then the process terminates (step 922). If the controlled medication dispensing bracelet 200 is enabled, the dispense meds from bracelet process 900 checks for a dispensing time (step 930). If the dispense meds from bracelet process 900 determines that it is not the correct time for administration of the medication (decision step 920), then the process terminates (step 932). If the dispense meds from bracelet process 900 determines that it is the correct time (or within a correct window of time) for dispensing the medication, the dispense meds from bracelet process 900 proceeds to validate the user (step 940). Validation of the user can be accomplished using any suitable process. Two exemplary processes include use of a biometric sensor (finger print reader, hand reader, palm reader, and the like)(step 942) and/or use of a facial recognition process (step 944). It is understood that any number of user verification processes can be employed, including those mentioned, as well as voice recognition, iris scanner, and the like. The dispense meds from bracelet process 900 then determines whether if the process validated the user (decision step 950). If the user is not validated (decision step 950), then the process terminates (step 952). If the user is validated (decision step 950), the dispense meds from bracelet process 900 proceeds to dispense medication from the primary tray 116 (step 960). To accomplish the dispensing process (step 960), the dispense meds from bracelet process 900 asks to select the bracelet compartment (step 962). The dispense meds from bracelet process 900 activates the motor to open the respective bracelet door (step 964). The dispense meds from bracelet process 900 proceeds with a decision step to determine if the medication has been ingested (decision step 970). If process determines that the medication hasn't been ingested (decision step 970), the dispense meds from bracelet process 900 loops back to ensure the door to the respective bracelet compartment is open (step 964). If the dispense meds from bracelet process 900 determines that the medication was taken, the dispense meds from bracelet process 900 activates the motor to close the bracelet door (step 972). The process terminates (step 974).

The inclusion of two distinct trays, each tray filled with a respective set of medication, provides a unique advantage when dealing with certain types of medication, including by not limited to narcotics, Opioids, other highly addictive medication, and the like. The additional inclusion of a user interface (such as the artificial intelligence avatar 132) enables the narcotics and Opioids secure storage and dispensing apparatus 100 to acquire additional information from the patient. The narcotics and Opioids secure storage and dispensing apparatus 100 can acquire information pertaining to the patient and use that information to determine whether it is appropriate to dispense the narcotics. In one example, the primary medication tray 110 can be filled with prescribed narcotics, and the secondary medication tray 120 can be filled with less addictive medications. In a condition where the narcotics and Opioids secure storage and dispensing apparatus 100 acquires information from the patient that introduces suspicion that the narcotic or Opioid is actually medically necessary (as opposed to being requested to support an addiction), the narcotics and Opioids secure storage and dispensing apparatus 100 can dispense medication from the secondary medication tray 120. This can be determined by intelligence within the narcotics and Opioids secure storage and dispensing apparatus 100, sending acquired patient input to a prescribing physician, or any other suitable decision making process. Details of an application of the dual tray benefits of the narcotics and Opioids secure storage and dispensing apparatus 100 are presented in an exemplary medication dispensing triage process 1000 described in FIGS. 44A and 44B.

The exemplary medication dispensing triage process 1000 can be initiated (step 1010) via a request to dispense medication (step 1020). The request can be via a dispense medication request button (not shown), a request through the interactive system, through an application on a mobile device, or any other method of requesting dispensing of medication. Upon initiation of the request to dispense medication (step 1020), the process determines of the request is being submitted within prescribed dispense time (decision step 1030). This is preferably accomplished via software operating on the microprocessor 310. In a condition where the request is submitted within prescribed dispense time (decision step 1030), the narcotics and Opioids secure storage and dispensing apparatus 100 dispenses the medication from the primary medication tray 110 (step 1032) and subsequently terminates the process (step 1034). In a condition where the request is submitted outside of the prescribed dispense time (decision step 1030), the process notifies an associated user counselor and/or physician(s) (step 1036). In a preferred scenario, the process would notify all parties associated with the treatment of the user, including the user's counselor, the user's medical team, and any other parties involved in the treatment of the user (step 1036). The process would then prompt the user to enter/answer information to determine a validity for dispensing of primary medication at the requested time (step 1038). The user would respond by entering the requested information to determine the validity for dispensing of primary medication at the requested time (step 1039). The requested information can additionally include a request for medical data, such as a urine specimen. The urine specimen can be obtained and processed through a portable urine tester (not shown) that would interact with the narcotics and Opioids secure storage and dispensing apparatus 100. Another optional test would be a breathalyzer for testing of alcohol. It is understood that any suitable testing device can interact with the narcotics and Opioids secure storage and dispensing apparatus 100 to acquire medical information pertaining to the user. Other examples include a blood pressure monitor, a glucose monitor, and the like.

Upon receipt of the responses to the requested information to determine the validity for dispensing of primary medication at the requested time (step 1039), the responses are reviewed to determine whether the responses to the requested information to determine the validity for dispensing of primary medication at the requested time (step 1039) justify a condition for dispensing of primary medication at the requested time (decision step 1040). The decision can be completed by a person or the automated system. The automated system can employ artificial intelligence, wherein the artificial intelligence is developed by learning from previous decisions and results. When determined that the conditions for dispensing of primary medication at the requested time (decision step 1040) are valid, the appropriate medication is dispensed from the primary medication tray 110 (step 1042) and the process terminates (step 1044).

When determined that the conditions for dispensing of primary medication at the requested time (decision step 1040) are not valid, the system can proceed to determine if the situation warrants dispensing of medication from the secondary medication tray 120 (decision step 1050) and/or notification of the prescription counselor of the request for dispensing of medication and the submitted reasons for the request (step 1060). When the situation warrants dispensing of medication from the secondary medication tray 120 (decision step 1050), the narcotics and Opioids secure storage and dispensing apparatus 100 proceeds with dispensing of medication from the secondary medication tray 120 (step 1052) and the process terminates (step 1054). An example would be dispensing of a non addictive (non-habit forming) prescription or non-prescription analgesic drug when the user requests dispensing of an addictive class II drug (such as narcotics, Opioids and the like). When the situation does not warrant dispensing of medication from the secondary medication tray 120 (decision step 1050), the process terminates (step 1056).

The narcotics and Opioids secure storage and dispensing apparatus 100 is designed to ensure that the user is monitored by appropriate parties during the period of use of the narcotics and Opioids secure storage and dispensing apparatus 100. The notification of the prescription counselor of the request for dispensing of medication and the submitted reasons for the request (step 1060) ensures that the user is adequately monitored by appropriate parties during the period of use of the narcotics and Opioids secure storage and dispensing apparatus 100.

Upon notification, the counselor for the user would determine a need for a plan for the patient (user) (decision step 1070). In a condition where the counselor determines that the conditions warrant dispensing of medication from the primary medication tray 110 the narcotics and Opioids secure storage and dispensing apparatus 100 proceeds in dispensing medication from the primary medication tray 110 (step 1090) and the process terminates (step 1092).

In a condition where the counselor determines that the conditions warrant generation of a plan, the counselor determines an appropriate patient treatment plan (step 1072) and the process proceeds in accordance with the appropriate patient treatment plan (step 1074). The plan may include dispensing of medication. The plan can direct dispensing of primary medication, dispensing of supplemental medication, or both.

In a condition where the plan includes dispensing of medication from the primary medication tray 110 (decision step 1076), the narcotics and Opioids secure storage and dispensing apparatus 100 proceeds in dispensing medication from the primary medication tray 110 (step 1078) and the process terminates (step 1079). In a condition where the plan includes dispensing of medication from the secondary medication tray 120 (decision step 1076), the narcotics and Opioids secure storage and dispensing apparatus 100 proceeds in dispensing medication from the secondary medication tray 120 (step 1080) and the process terminates (step 1082).

In a condition where the counselor determines that the conditions warrant dispensing of medication from the primary medication tray 110 (decision step 1070) exclusive of a requirement for generating an appropriate treatment plan (step 1072) the narcotics and Opioids secure storage and dispensing apparatus 100 proceeds in dispensing medication from the primary medication tray 110 (step 1090) and the process terminates (step 1092).

The narcotics and Opioids secure storage and dispensing apparatus 100 includes a patient interactive system and two trays 110, 120 carrying differing levels of drugs. This combination provides a unique capability to support a patient/user taking class II medication and/or potentially an addiction. The narcotics and Opioids secure storage and dispensing apparatus 100 enables dispensing of the class II medication from the primary medication tray 110 or alternative, non-addictive medication from the secondary medication tray 120 upon an intelligence decision. Additionally, the narcotics and Opioids secure storage and dispensing apparatus 100 is adapted to enable treatment of an accidental overdose.

An exemplary narcotics and Opioids secure storage and dispensing apparatus 100, a controlled medication dispensing bracelet 200, and an associated method of use are described herein. Although the apparatus and methods taught herein are the preferred and alternate embodiments, it can be recognized that other form factors, materials, and methods of achieving the same results can be contrived from the disclosed teachings. The narcotics and Opioids secure storage and dispensing apparatus 100 as well as the controlled medication dispensing bracelet 200 can be modified to include differing features, a different shape, different user interface devices, activity indicators, such as lights, or any other desired feature and/or function. functions of the narcotics and Opioids secure storage and dispensing apparatus 100 can be integrated in the controlled medication dispensing bracelet 200. For example, the rotary design of the narcotics and Opioids secure storage and dispensing apparatus 100 can be arranged in a linear arrangement, where the dispensing mechanism travels along a linear guide. In another example, the controlled medication dispensing bracelet 200 can store the suspected overdose counteracting drug 148 in one of the available bracelet medication compartments 210.

REFERENCE ELEMENT DESCRIPTIONS

Ref. No. Description 100 narcotics and Opioids secure storage and dispensing apparatus
110 primary medication tray
112 primary tray medication compartment
114 top cover
116 dispense compartment
117 dispensing chute
118 punch lever
120 secondary medication tray
122 secondary tray medication compartment
124 secondary medication tray cover
129 supplemental medications, vitamins and other pills
130 display unit
132 artificial intelligence avatar
134 speaker
136 microphone
138 panic button
139 narcotics and Opioids secure storage and dispensing apparatus charging contacts
140 front supporting leg
141 front supporting leg storage access element
142 rear supporting leg
143 front supporting leg storage access
148 suspected overdose counteracting drug
150 sliding shafts
152 secondary tray cover locking harness
154 dual tray cover interconnected locking shaft
160 sealed blister pack
162 blister pack medication compartments
170 medication dispensing member
172 medication consumption tracking (fisheye) camera
174 medication dispense monitoring camera
176 biometric monitoring sensor
178 light emitting element
180 reclamation safe
182 reclamation safe repository aperture
184 reclamation safe repository
186 reclamation safe pill collection sweeper
187 reclamation safe pill collection sweeper rotational axis
200 controlled medication dispensing bracelet
210 bracelet medication compartment
212 bracelet compartment door
214 bracelet compartment door motor
220 main bracelet control unit
222 bracelet touch display unit
224 bracelet artificial intelligence Avatar assistant
230 bracelet band
250 storage cart (docking station)
260 storage shelf
262 charging contacts
270 storage cart interactive system
300 secure storage for dispensing of Opioids electronic block diagram
310 microprocessor
320 memory module
322 program
324 database
326 text to speech (TTS), speech to text (STT) and Natural Language Processing (NLP)
328 storage area for triage data
330 power management system
332 battery
334 docking station interface
336 charging circuitry
338 bracelet interface
340 wireless module
342 cellular transmission circuitry
344 Wi-Fi circuitry
346 Bluetooth circuitry 347 RFID circuitry
348 Global Positioning System (GPS)/Global Navigation Satellite System (GNSS) receiver
349 antenna
350 motor controller
352 for a primary tray motor control circuitry
354 secondary tray motor control circuitry
356 punch lever motor control circuitry
358 bracelet door motor control circuitry
359 dispense door motor control circuitry
360 user interface
362 display controller
364 button
366 speaker and a microphone
368 mobile device
370 sensory system
372 motion sensor
374 noise sensor
376 digital scale
400 track me process
410 track me process initiation step
420 track me process enabled decision step
422 termination step
430 establish geo-fence for the narcotics and Opioids secure storage and dispensing apparatus step
432 establish geo-fence for the Opioid dispensing bracelet step
440 device crosses geo-fence boundary decision step
442 send notiifcation to remote operators/caregivers step
500 locate me process
510 locate me process initiation step
520 locate me process enabled decision step
522 termination step
530 send notification step with dispenser GPS location step
532 send notification step with bracelet GPS location step
600 schedule medication process
610 schedule medication process activation step
620 determine which tray is dispensing medication decision step
622 determine if a blister pack is being used decision step
630 request entry of desired medication step
632 request entry of dosage of medication step
634 request entry of any additional instructions step
636 selection date and time for administration of medication step
638 setting reminder when to take medication step
639 prompt to refill medication step
640 prompt loading of blister pack step
642 request entry of desired medication step
644 request entry of dosage of medication step
646 request entry of any additional instructions step
647 selection date and time for administration of medication step
648 setting reminder when to take medication step
649 prompt to refill medication step
650 promt to select supplemental medication step
652 prompt for a dosage selection of the secondary medication
654 prompt special instructions associated with supplemental medication step
656 prompt selection and linking to the associated primary tray medication date and time
658 prompt to add reminders
659 prompt to refill supplemental medication step
700 dispense medication process
710 dispense medication process initiation step
720 determining the dispense day and time step
722 termination step
730 acquire validation of the user ingesting medication step
740 validation of the user ingesting medication decision step
742 termination step
750 dispense medication from primary tray step
760 supplemental medication linked decision step
762 termination step
770 dispense medication from secondary tray step
800 transport meds to bracelet process
810 transport meds to bracelet process initiation
820 medication dispensing bracelet
822 termination step
830 bracelet docked decision step
832 termination step
840 log bracelet compartment number step
842 activate motor to open bracelet compartment door step
844 select primary medication tray step
846 dispense medication from primary tray to bracelet step
850 determine if supplemental medication is linked decision step
852 activate motor to close bracelet compartment door step
854 termination step
860 dispense supplemental medication step
900 dispense meds from bracelet process
910 dispense meds from bracelet process initiation
920 bracelet enabled decision step
922 termination step
930 determine dispense time decision step
932 termination step
940 user validation process step
942 biometric sensing process
944 facial recognition process
950 user validated decision step
952 termination step
960 dispense medication from primary tray step
962 identify bracelet compartment to dispense medication step
964 activate motor to open bracelet compartment door step
970 determine if medication has been injested
972 activate motor to close bracelet compartment door step
974 termination step
1000 medication dispensing triage process
1010 medication dispensing triage process initiation
1020 user requests dispensing medication step
1030 request within prescribed dispense time decision step
1032 dispense medication from primary tray step
1034 termination step
1036 notify counselor and/or physicians step
1038 propt dispense validity status information acquisition step
1039 enter dispense validity status information step
1040 validate reasons for prescribing medication decision step
1042 dispense medication from primary tray step
1044 termination step
1050 dispense supplemental medication decision step
1052 dispense supplemental medication step 1054 termination step
1056 termination step
1060 inform prescription counselor step
1070 counselor determines need for patient plan decision step
1072 determine appropriate patient treatment plan step
1074 proceed with appropriate patient treatment plan step
1076 approval to dispense primary medication decision step
1078 dispense medication from primary tray step
1079 termination step
1080 dispense medication from secondary tray step
1082 termination step
1090 dispense medication from primary tray step
1092 termination step

What is claimed is:

1. A secure medication dispensing system comprising:
a multi-tray medication dispensing apparatus and software for operating the multi-tray medication dispensing apparatus, the multi-tray medication dispensing apparatus comprising:
a. a microprocessor;
b. memory in signal communication with the microprocessor;
c. software comprising a set of instructions that are executed by the microprocessor, the software being stored in the memory;
d. a wireless transceiver in signal communication with the microprocessor;
e. a first tray, the first tray comprising a plurality of first tray medication compartments containing primary medication, the first tray being arranged to dispense the primary medication from each first tray medication compartment into a medication dispensing location;
f. a second tray, the second tray comprising a plurality of second tray medication compartments containing secondary supplemental medication, the second tray being arranged to dispense the secondary medication from each second tray medication compartment into the medication dispensing location;
g. at least one closure, wherein the at least one closure provides access to and a secure seal to each of the first tray and the second tray;
h. a user identification system in signal communication with the microprocessor,
i. a first tray operating control mechanism, wherein the first tray operating control mechanism positions the first tray respective to the dispensing location, the first tray operating control mechanism being controlled by the software;
j. a second tray operating control mechanism, wherein the second tray operating control mechanism positions the second tray respective to the dispensing location, the second tray operating control mechanism being controlled by the software;
k. a sensor in signal communication with the microprocessor, the sensor being arranged to detect when medication has been dispensed; and
l. A housing carrying the microprocessor, the memory, the sensor mechanism, the first tray, the second tray, and at least one medication dispensing mechanism,
the software comprising steps of:
requesting dispensing of the primary medication from the first tray;
initiating a request for information from the user as a result of the request for dispensing of the primary medication from the first tray, wherein the information requested is to determine an appropriateness of the primary medication for the user;
entry of information for authorizing dispensing of the primary medication from the first tray, wherein the entry of information is provided by the user,
the entered information is considered to determine:
(a) if dispensing the primary medication from the first tray is appropriate based upon the information entered by the user,
(b) if dispensing the supplemental medication from the second tray is appropriate based upon the information entered by the user, or
(c) if providing an alternative action to dispensing any medication is appropriate based upon the information entered by the user;
wherein, in a condition where the entered information determines the condition to be appropriate to dispense primary medication from the first tray, the multi-tray medication dispensing apparatus dispenses primary medication from the first tray,
wherein, in a condition where the entered information determines the condition to be appropriate to dispense supplemental medication from the second tray, the multi-tray medication dispensing apparatus dispenses supplemental medication from the second tray, and
wherein, in a condition where the entered information determines the condition to be appropriate to provide an alternative action to dispensing any medication, the system initiates an alternative action.

2. The secure medication dispensing system as recited in claim 1, wherein the first tray is provided in a form of a rotatable carousel and the second tray is provided in a form of a rotatable carousel,
wherein the arrangement to dispense the primary medication from the first tray is accomplished by rotating the first tray, and
wherein the arrangement to dispense the secondary medication from the second tray is accomplished by rotating the second tray.

3. The secure medication dispensing system as recited in claim 1, further comprising at least one medication dispensing mechanism, the at least one medication dispensing mechanism being arranged to dispense medication from at least one of the first tray and the second tray, the medication being dispensed into the medication dispensing location.

4. The secure medication dispensing system as recited in claim 1, further comprising at least one blister pack, the at least one blister pack being located in at least one of the first tray and the second tray.

5. The secure medication dispensing system as recited in claim 4, further comprising a punch lever arranged to excise medication from the at least one blister pack via a combination of a radial motion of the punch lever in combination with a rotational motion of the respective one of the first tray and the second tray.

6. The secure medication dispensing system as recited in claim 1, wherein the primary medication stored in the first tray medication compartments of the first tray is classified as a class II drug.

7. The secure medication dispensing system as recited in claim 6, wherein the primary medication stored in the first tray medication compartments of the first tray is classified as a class II drug,
wherein the multi-tray medication dispensing apparatus dispenses the class II drug only after verification that the user of the class II drug meets predetermined criteria for administration of the class II drug.

8. The secure medication dispensing system as recited in claim 6, further comprising a medication reclamation safe, wherein the medication reclamation safe is configured to collect medication from the medication dispensing location when it is determined to collect the medication.

9. The secure medication dispensing system as recited in claim 1, further comprising a medication reclamation safe, wherein the medication reclamation safe is configured to collect medication from the medication dispensing location when it is determined to collect the medication.

10. The secure medication dispensing system as recited in claim 1, the medication dispensing location further comprising a medication staging location and a medication dispensing member, wherein the medication dispensing member is configured to dispense the medication from the medication staging location when it is determined to dispense the staged medication.

11. The secure medication dispensing system as recited in claim 1, wherein the primary medication stored in the first tray medication compartments of the first tray is a class II drug and the supplemental medication stored in the second tray medication compartments of the second tray is a non-addictive drug excluded from class II classification category.

12. The secure medication dispensing system as recited in claim 1, further comprising a panic button, wherein the panic button interacts with the multi-tray medication dispensing apparatus,
    upon actuation of the panic button, the system prompts entry of the information for authorizing dispensing of medication from the first tray.

13. The secure medication dispensing system as recited in claim 1, the software further comprising a step of dispensing medication from at least one second tray medication compartment of the plurality of second tray medication compartments independent of whether the first tray dispenses medication.

14. The secure medication dispensing system as recited in claim 1, further comprising a tamper proof dual lock mechanism which secures each of a first rotary cover sealing the first tray in a closed position and a second rotary cover sealing the second tray in a closed position.

15. The secure medication dispensing system as recited in claim 1, wherein the first tray and the second tray are provided in a linear assembly,
    wherein the arrangement to dispense the primary medication from the first tray is accomplished by accessing one compartment of the first tray, and
    wherein the arrangement to dispense the secondary medication from the second tray is accomplished by accessing one compartment of the second tray.

16. The secure medication dispensing system as recited in claim 1, further comprising at least one of:
    (a) an optical, non-contact sensor and programming for detection of one of a user's hand or a container into which the dispenser releases medication, and
    (b) a biometric sensing mechanism to authenticate an authorized user prior to execution of a step of dispensing medication.

17. The secure medication dispensing system as recited in claim 1, further comprising a biometric sensing mechanism to identify an authorized user prior to execution of a step of dispensing pills.

18. The secure medication dispensing system as recited in claim 1, further comprising a Global Positioning System (GPS) receiver, wherein the system reports a location of the multi-tray medication dispensing apparatus obtained using the Global Positioning System (GPS) receiver to the remote party.

19. The secure medication dispensing system as recited in claim 1, the multi-tray medication dispensing apparatus further comprising:
    m. a display in signal communication with the microprocessor;
    n. a microphone in signal communication with the microprocessor; and
    o. a speaker in signal communication with the microprocessor,
        wherein the housing additionally carries the display, the microphone, and the speaker,
        the software further comprising a step of:
        interacting with a user via an interactive artificial intelligence virtual assistant, wherein the interactive artificial intelligence virtual assistant communicates with the user via the display, the speaker, and the microphone.

20. The secure medication dispensing system as recited in claim 1, the multi-tray medication dispensing apparatus further comprising a cavity storing a suspected overdose counteracting medication.

21. The secure medication dispensing system as recited in claim 1, the multi-tray medication dispensing apparatus further comprising steps of:
    utilizing a dispensing schedule to identify when medication is to be dispensed; and
    monitoring the dispensing schedule,
    wherein in a condition where medication is not dispensed from the multi-tray medication dispensing apparatus within the scheduled dispense time period, notifying a remote party associated with at least one of operation of the multi-tray medication dispensing apparatus and care of the user,
    wherein the dispensing of the primary medication or the secondary medication is determined based upon at least one of:
    (a) a predetermined medication dispensing schedule, and
    (b) a real time authorization.

* * * * *